(12) United States Patent
Crew et al.

(10) Patent No.: US 10,071,164 B2
(45) Date of Patent: Sep. 11, 2018

(54) ESTROGEN-RELATED RECEPTOR ALPHA BASED PROTAC COMPOUNDS AND ASSOCIATED METHODS OF USE

(71) Applicants: Yale University, New Haven, CT (US); Arvinas, Inc., New Haven, CT (US)

(72) Inventors: Andrew Crew, Guilford, CT (US); Craig Crews, New Haven, CT (US); Hanqing Dong, Madison, CT (US); Eunhwa Ko, New Haven, CT (US); Jing Wang, Milford, CT (US)

(73) Assignees: Yale University, New Haven, CT (US); Arvinas, Inc., New Haven, CT (US)

( * ) Notice: Subject to any disclaimer, the term of this patent is extended or adjusted under 35 U.S.C. 154(b) by 0 days.

(21) Appl. No.: 14/822,309

(22) Filed: Aug. 10, 2015

(65) Prior Publication Data
US 2016/0045607 A1 Feb. 18, 2016

Related U.S. Application Data

(60) Provisional application No. 62/036,000, filed on Aug. 11, 2014.

(51) Int. Cl.
| | | |
|---|---|---|
| *C07K 5/062* | (2006.01) |
| *C07K 5/097* | (2006.01) |
| *A61K 45/06* | (2006.01) |
| *A61K 31/427* | (2006.01) |
| *A61K 31/426* | (2006.01) |
| *A61K 38/00* | (2006.01) |
| *A61K 47/48* | (2006.01) |

(52) U.S. Cl.
CPC .......... *A61K 47/481* (2013.01); *A61K 31/426* (2013.01); *A61K 31/427* (2013.01); *A61K 45/06* (2013.01); *A61K 47/48061* (2013.01); *C07K 5/06026* (2013.01); *C07K 5/06034* (2013.01); *C07K 5/06052* (2013.01); *C07K 5/0821* (2013.01); *A61K 38/00* (2013.01)

(58) Field of Classification Search
CPC combination set(s) only.
See application file for complete search history.

(56) References Cited

U.S. PATENT DOCUMENTS

| | | |
|---|---|---|
| 4,522,811 A | 6/1985 | Eppstein et al. |
| 5,681,858 A | 10/1997 | Stevens et al. |
| 6,306,663 B1 | 10/2001 | Kenten et al. |
| 6,559,280 B2 | 5/2003 | Kenten et al. |
| 7,041,298 B2 | 5/2006 | Deshaies et al. |
| 7,074,620 B2 | 7/2006 | Kenten et al. |
| 7,208,157 B2 | 4/2007 | Sakamoto et al. |
| 7,273,920 B2 | 9/2007 | Kenten et al. |
| 7,683,160 B2 | 3/2010 | Eckhardt et al. |
| 9,500,653 B2 | 11/2016 | Crews et al. |
| 9,632,089 B2 | 4/2017 | Crews et al. |
| 2006/0128632 A1 | 6/2006 | Sharma et al. |
| 2010/0048517 A1 | 2/2010 | Hu et al. |
| 2012/0270800 A1 | 10/2012 | Verdine et al. |
| 2014/0302523 A1 | 10/2014 | Crews et al. |
| 2014/0356322 A1 | 12/2014 | Crews et al. |
| 2015/0291562 A1 | 10/2015 | Crew et al. |
| 2015/0344473 A1 | 12/2015 | Du et al. |
| 2016/0022642 A1 | 1/2016 | Crews et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |

FOREIGN PATENT DOCUMENTS

| | | |
|---|---|---|
| EP | 0805147 A1 | 11/1997 |
| WO | 0022110 A2 | 4/2000 |
| WO | 0050445 A1 | 8/2000 |

(Continued)

OTHER PUBLICATIONS

Chemical Abstract Service (CAS) STN Registry Database No. 871986-52-6 [entered STN: Jan 16, 2006].*
Bondenson et al. "Catalytic in vivo protein knockdown by small-molecule PROTACs" Nat. Chem. Biol. 2015, 11, 611-617 (Year: 2015).*
PCT International Search Report and Written Opinion for PCT/US2013/021136 dated Jun. 27, 2013.
Aghajanyy, et al., "Chemical genetics screen for enhancers of rapamycin identifies a specific inhibitor of an SCF family E3 ubiquitin ligase", Nature Biotechnology 28(7), Jun. 27, 2010, 738-742.
Boitano, et al., "Aryl Hydrocarbon Receptor Antagonists Promote the Expansion of Human Hematopoietic Stem Cells", Science 329, Sep. 10, 2010, 1345-1348.

(Continued)

*Primary Examiner* — Amanda L Aguirre
(74) *Attorney, Agent, or Firm* — Saul Ewing Arnstein & Lehr LLP; Kathryn Doyle; Domingos J. Silva

(57) ABSTRACT

The present invention relates to bifunctional compounds, which find utility as modulators of targeted ubiquitination, especially inhibitors of a variety of polypeptides and other proteins which are degraded and/or otherwise inhibited by bifunctional compounds according to the present invention. In particular, the present invention is directed to compounds, which contain on one end a VHL ligand which binds to the ubiquitin ligase and on the other end a moiety which binds a target protein such that the target protein is placed in proximity to the ubiquitin ligase to effect degradation (and inhibition) of that protein. The present invention exhibits a broad range of pharmacological activities associated with compounds according to the present invention, consistent with the degradation/inhibition of targeted polypeptides.

9 Claims, 16 Drawing Sheets

(56) References Cited

FOREIGN PATENT DOCUMENTS

| WO | 0066119 | A1 | 11/2000 | | |
|---|---|---|---|---|---|
| WO | 0175145 | A2 | 10/2001 | | |
| WO | 0222577 | A2 | 3/2002 | | |
| WO | 02100845 | A1 | 12/2002 | | |
| WO | 2006069063 | A1 | 6/2006 | | |
| WO | 2006113942 | A2 | 10/2006 | | |
| WO | 2007106670 | A2 | 9/2007 | | |
| WO | 2008011392 | A8 | 7/2008 | | |
| WO | 2008109727 | A1 | 9/2008 | | |
| WO | 2008109731 | A2 | 9/2008 | | |
| WO | 2008134679 | A1 | 11/2008 | | |
| WO | 2009015254 | A1 | 1/2009 | | |
| WO | 2010107485 | A1 | 9/2010 | | |
| WO | 2010141805 | A1 | 12/2010 | | |
| WO | 2011008260 | A1 | 1/2011 | | |
| WO | 2011143660 | A2 | 11/2011 | | |
| WO | 2011160016 | A2 | 12/2011 | | |
| WO | 2012003281 | A2 | 1/2012 | | |
| WO | 2012009649 | A1 | 1/2012 | | |
| WO | 2012040527 | A2 | 3/2012 | | |
| WO | 2012054110 | A2 | 4/2012 | | |
| WO | 2012078559 | A2 | 6/2012 | | |
| WO | 2012142498 | A2 | 10/2012 | | |
| WO | 2013106643 | A2 | 7/2013 | | |
| WO | 2013106646 | A2 | 7/2013 | | |
| WO | 2013170147 | A1 | 11/2013 | | |
| WO | 2014011712 | A1 | 1/2014 | | |
| WO | 2014025759 | A1 | 2/2014 | | |
| WO | 2014047024 | A1 | 3/2014 | | |
| WO | 2014055461 | A1 | 4/2014 | | |
| WO | 2014108452 | A1 | 7/2014 | | |
| WO | 2015000867 | A1 | 1/2015 | | |
| WO | 2015000868 | A1 | 1/2015 | | |
| WO | 2015006524 | A1 | 1/2015 | | |
| WO | 2016146985 | A1 | 9/2016 | | |
| WO | WO-2016172134 | A2 | * | 10/2016 | ........... C07D 401/14 |
| WO | 2016197114 | A1 | 12/2016 | | |
| WO | 2017011590 | A1 | 1/2017 | | |
| WO | 2017030814 | A1 | 2/2017 | | |
| WO | 2017079267 | A1 | 5/2017 | | |

OTHER PUBLICATIONS

Bondeson, et al., "Catalytic in vivo protein knockdown by small-molecule PROTACs", Nat Chem Biol. 1(8), Aug. 2015, 611-617.
Brough, et al., "4,5-Diarylisoxazole HSP90 Chaperone Inhibitors: Potential Therapeutic Agents for the Treatment of Cancer", J Med Chem. 51(2), Jan. 24, 2008, 196-218.
Buckley, et al., "Small-molecule inhibitors of the interaction between the E3 ligase VHL and HIF1α", Angew Chem Int Ed Engl.51(46), Oct. 12, 2012, 11463-11467.
Buckley, et al., "Targeting the von Hippel-Lindau E3 ubiquitin ligase using small molecules to disrupt the VHL/HIF-1α interaction", Journal of the American Chemical Society 134(10), Feb. 27, 2012, 4465-4468.
Chang, et al., "Structural basis for G9a-like protein lysine methyltransferase inhibition by BIX-01294", Nat Struct Mol Biol. 16(3), Mar. 2009, 312-317.
Chung, et al., "Discovery and Characterization of Small Molecule Inhibitors of the BET Family Bromodomains", J Med Chem. 54(11), Jun. 9, 2011, 3827-3838.
Cyrus, et al., "Jostling for position: optimizing linker location in the design of estrogen receptor-targeting PROTACs", ChemMedChem. 5(7), Jul. 5, 2010, 979-985.
Dawson, et al., "Inhibition of BET recruitment to chromatin as an effective treatment for MLL-fusion leukaemia", Nature 478, Oct. 2, 2011, 529-533.
Filippakopoulos, et al., "Selective inhibition of BET bromodomains", Nature 468, Dec. 23, 2010, 1067-1073.
Finnin, et al., "Structures of a histone deacetylase homologue bound to the TSA and SAHA inhibitors", Nature 401, Sep. 9, 1999, 188-193.
Hewings, et al., "3,5-Dimethylisoxazoles Act As Acetyllysine-mimetic Bromodomain", J Med Chem. 54(19), Oct. 13, 2011, 6761-6770.
Hon, et al., "Structureal basis for the recognition of hydroxyproline in HIf-1a by pVHL", Nature 417, Jun. 27, 2002, 975-978 (Abstract).
Jiang, et al., "Synthesis of 7alpha-substituted derivatives of 17beta-estradiol", Steroids 71(5), May 2006, 334-342 (Abstract).
Lee, et al., "Targeted Degradation of the Aryl Hydrocarbon Receptor by the PROTAC Approach: A Useful Chemical Genetic Tool", ChemBioChem. 8(17), Nov. 23, 2007, 2058-2062.
Liu, et al., "Discovery of a 2,4-diamino-7-aminoalkoxyquinazoline as a potent and selective inhibitor of histone lysine methyltransferase G9a", J Med Chem. 52(24), Dec. 24, 2009, 7950-7953.
Llinàs-Brunet, et al., "Discovery of a potent and selective noncovalent linear inhibitor of the hepatitis C virus NS3 protease (BI 201335)", J Med Chem. 53(17), Sep. 9, 2010, 6466-6476.
Lountos, et al., "Structural Characterization of Inhibitor Complexes with Checkpoint Kinase 2 (Chk2), a Drug Target for Cancer Therapy", J Struct Biol.176(3), Dec. 2011, 292-301.
Mehellou, et al., "Twenty-six years of anti-HIV drug discovery: where do we stand and where do we go?", J Med Chem. 53(2), Jan. 28, 2010, 521-538.
Millan, et al., "Design and Synthesis of Inhaled p38 Inhibitors for the Treatment of Chronic Obstructive Pulmonary Disease", J Med Chem.54(22), Nov. 24, 2011, 7797-7814.
Min, et al., "Structue of an HIV-1-alpha—pVHL complex: hydroxyproline recognition in signaling", Science 296, Jun. 27, 2002, 1886-1889.
Nicodeme, et al., "Suppression of inflammation by a synthetic histone mimic", Nature 468, Dec. 23, 2010, 1119-1123.
Patch, et al., "Identification of diaryl ether-based ligands for estrogen-related receptor α as potential antidiabetic agents", J Med Chem. 54(3), Feb. 10, 2011, 788-808.
Prakash, et al., "Stereoselective Nucleophilic Trifluoromethylation of N-(tert-Butylsulfinyl)imines by Using Trimethyl (trifluoromethyl)silane", Angew Chem Int Ed Engl. 40(3), Feb. 2, 2001, 589-590 (Abstract).
Rodriguez-Gonzalez, et al., "Targeting steroid hormone receptors for ubiquitination and degradation in breast and prostate cancer", Oncogene. 27(57), Dec. 4, 2008, 7201-7211.
Rusch, et al., "Identification of acyl protein thioesterases 1 and 2 as the cellular targets of the Ras-signaling modulators palmostatin B and M", Angew Chem Int Ed Engl.50(42), Oct. 10, 2011, 9838-9842.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1 -Cullin-F box complex for ubiquitination and degradation", Proc Natl Acad Sci U S A.98(15), Jul. 17, 2001, 8554-8559.
Sargent, et al., "Synthesis of the cyclophane tetramethoxyturriane: a derivative of the phenolic cyclophanes of Grevillea striata R. Br.", J. Chem. Soc., Perkin Trans. 1, 1990, 129-132 (Abstract).
Schenkel, et al., "Discovery of Potent and Highly Selective Thienopyridine Janus Kinase 2 Inhibitors", J Med Chem.54(24), Dec. 22, 2011, 8440-8450.
Schneekloth, et al., "Chemical Genetic Control of Protein Levels: Selective in Vivo Targeted Degradation", J Am Chem Soc. 126(12), Mar. 31, 2004, 3748-3754.
Smith, et al., "Targeted Intracellular Protein Degradation Induced by a Small Molecule: En Route to Ghemical Proteomics", Bioorg Med Chem Lett. 18(22), Nov. 15, 2008, 5904-5908.
Valle, et al., "Tricyclic Series of Heat Shock Protein 90 (HSP90) Inhibitors Part I: Discovery of Tricyclic Imidazo[4,5-c]Pyridines as Potent Inhibitors of the HSP90 Molecular Chaperone", J Med Chem. 54(20), Oct. 27, 2011, 7206-7219.
Van Eis, et al., "2,6-Naphthyridines as potent and selective inhibitors of the novel protein kinase C isozymes", Bioorg Med Chem Lett.21(24), Dec. 15, 2011, 7367-7372.
Van Molle, et al., "Dissecting fragment-based lead discovery at the von Hippel-Lindau protein:hypoxia inducible factor 1α protein-protein interface", Chem Biol. 19(10), Oct. 26, 2012, 1300-1312.

(56) References Cited

OTHER PUBLICATIONS

Vassilev, et al., "In vivo activation of the p53 pathway by small-molecule antagonists of MDM2", Science 303, Feb. 6, 2004, 844-848.
Wright, et al., "Structure-Activity Relationships in Purine-Based Inhibitor Binding to HSP90 Isoforms", Chem Biol. 11(6), Jun. 2004, 775-785.
Ahn, et al., HIF-1alpha peptide derivatives with modifications at the hydroxyproline residue as activators of HIF-1alpha, Bioorg Med Chem Lett. 19(15), 2009, 4403-4405.
Buckley, et al., HaloPROTACS: Use of Small Molecule PROTACs to Induce Degradation of HaloTag Fusion Proteins, ACS Chem BioL10(8), 2015, 1831-1837.
Cyrus, et al., Impact of linker length on the activity of PROTACs, Mol Biosyst. 7(2), 2011, 359-364.
Galdeano, et al., Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities, J Med Chem. 57(20), 2014, 8657-8663.
Lu, et al., Hijacking the E3 Ubiquitin Ligase Cereblon to Efficiently Target BRD4, Chem Biol. 22(6), 2015, 755-763.
Puppala, et al., Development of an aryl hydrocarbon receptor antagonist using the proteolysis-targeting chimeric molecules approach: a potential tool for chemoprevention, Mol Pharmacol. 73(4), 2008, 1064-1071.
Raina, et al., PROTAC-induced BET protein degradation as a therapy for castration-resistant prostate cancer, Proc Natl Acad Sci U S A. 113(26), 2016, 7124-7129.
Winter, et al., Drug Development. Phthalimide conjugation as a strategy for in vivo target protein degradation, Science. 348(6241), 2015, 1376-1381.
Zengerle, et al., Selective Small Molecule Induced Degradation of the BET Bromodomain Protein BRD4, ACS Chem Biol. 10(8), 2015, 1770-1777.
Zhou, et al., Discovery of a Small-Molecule Degrader of Bromodomain and Extra-Terminal (BET) Proteins with Picomolar Cellular Potencies and Capable of Achieving Tumor Regression, J Med Chem. 61(2), 2018, 462-481.

* cited by examiner

HaloTag™ Protein

HaloTag™ Protein:
- Binds to chloro-alkanes irreversibly

Chloro-alkane Ligand
- PEG based connector
- Small molecule VHL ligand

- (R)-
- (S)-

(S)-isomer inactive (R)-isomer inactive
$DC_{50}$ = 13 nM
$DC_{90}$ = 100 nM
$D_{max}$ >90%

$DC_{50}$ = 13 nM, 90% degradation observed at 100 nM

ESTROGEN-RELATED RECEPTOR ALPHA BASED PROTAC COMPOUNDS AND ASSOCIATED METHODS OF USE

CROSS REFERENCE TO RELATED APPLICATIONS

This application claims priority under 35 U.S.C. § 119(e) to U.S. Provisional Application No. 62/036,000, filed Aug. 11, 2014, which application is incorporated herein by reference in its entirety.

STATEMENT REGARDING FEDERALLY SPONSORED RESEARCH

This invention was made with Government support under contract AI084140 awarded by the National Institutes of Health. The Government has certain rights in the invention.

BACKGROUND OF THE INVENTION

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which over 600 are known in humans) confer substrate specificity for ubiquitination, and therefore are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands that bind to these ligases. For example, since the discovery of nutlins, the first small molecule E3 ligase inhibitors, additional compounds have been reported that target E3 ligases but the field remains underdeveloped.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. A small molecule ligands of Von Hippel Lindau (VHL) to the substrate recognition subunit of the E3 ligase, VCB (an important target in cancer, chronic anemia and ischemia) was generated, and crystal structures thereof confirmed that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a not completely elucidated mechanism, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. This ubiquitin ligase complex is thus important for limb outgrowth in embryos. In the absence of cereblon, DDB1 forms a complex with DDB2 that functions as a DNA damage-binding protein. Increased expression of cereblon has been linked to an increase in efficacy of imide drugs in the treatment of multiple myeloma.

Receptor interacting serine/threonine-protein kinase 2 (RIPK2) functions as an important mediator of innate immune signaling. Once activated, RIPK2 associates with NOD1 and NOD2 to recruit other kinases (TAK1, IKKα, IKKβ, IKKγ) involved in NF-κB and MAPK activation. Dysregulation of RIPK2-dependent signaling is associated with autoinflammatory diseases including Blau syndrome and early-onset sarcoidosis.

An ongoing need exists in the art for effective treatments for disease, especially hyperplasias and cancers, such as multiple myeloma. However, non-specific effects, and the inability to target and modulate certain classes of proteins altogether, such as transcription factors, remain as obstacles to the development of effective agents (e.g., anti-cancer agents). As such, small molecule therapeutic agents that demonstrate substrate specificity and, at the same time, are "tunable" such that a wide range of protein classes can be targetted and modulated with specificity would be very useful as a therapeutic. The present invention addresses this need.

BRIEF SUMMARY OF THE INVENTION

The present invention relates to bifunctional compounds that are useful as modulators of targeted ubiquitination, especially inhibitors of a variety of polypeptides and other proteins, which are consequently degraded and/or otherwise inhibited. In one aspect, the present invention is directed to compounds that contain on one end a VHL ligand, which binds to the VHL E3 ubiquitin ligase (defined as a ubiquitin ligand binding moiety or ULM group) and on the other end a moiety that binds a target protein (defined as a protein/polypeptide targeting moiety or PTM group), such that the target protein/polypeptide is placed in proximity to the ubiquitin ligase to effect degradation (and inhibition) of that protein. The present invention exhibits a broad range of pharmacological activities associated with compounds according to the present invention, consistent with the degradation/inhibition of targeted polypeptides.

The present disclosure further provides bifunctional compounds that function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited. An exemplary advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer.

In an additional aspect, the disclosure provides bifunctional or PROTAC compounds, which comprise an E3 Ubiquitin Ligase binding moiety (i.e., a ligand for an E3 Ubquitin Ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In certain embodiments, the PTM is an estrogen-related receptor alpha (ERRα), androgen receptor (AR), and/or RIPK2 binding moiety. In other embodiments, the ULM is a VHL, cereblon, mouse double minute 2 (MDM2), and/or inhibitor of apoptosis protein (IAP) E3 ligase binding moiety. For example, the structure of the bifunctional compound can be depicted as PTM-ULM.

The respective positions of the PTM and ULM moieties, as well as their number as illustrated herein, is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as PTM-L-ULM, where PTM is a protein/polypeptide targeting moiety (e.g., ERRα, AR, or RIPK2 binding moiety), L is a linker, and ULM is a VHL, cereblon, MDM2, or IAP E3 ligase binding moiety binding moiety.

In certain embodiments, the compounds as described herein comprise multiple ULMs, multiple PTMs, multiple chemical linkers, or any combinations thereof.

In another aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions that are modulated through the degraded protein. In certain embodiments, the therapeutic compositions as described herein may be used to effectuate the degradation of proteins of interest for the treatment or amelioration of a disease, e.g., cancer. In yet another aspect, the present invention provides a method of ubiquitinating/degrading a target protein in a cell. In certain embodiments, the method comprises administering a bifunctional compound as described herein comprising an ULM and a PTM, in certain embodiments linked through a linker moiety, as otherwise described herein, wherein the ULM is coupled to the PTM and wherein the ULM recognizes a ubiquitin pathway protein (e.g., an ubiquitin ligase, in certain embodiments an E3 ubiquitin ligase) and the PTM recognizes the target protein such that degradation of the target protein occurs when the target protein (e.g., ERRα, AR, or RIPK2) is placed in proximity to the ubiquitin ligase, thus resulting in degradation/inhibition of the effects of the target protein and the control of protein levels. In other embodiments, the target protein is ERRα. The control of protein levels afforded by the present invention provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present invention.

The invention provides a compound of chemical structure ULM-L-PTM, the compound comprising a small molecule ubiquitin ligase binding moiety (ULM), a protein targeting moiety (PTM), and a linker (L), wherein ULM comprises a group substituted with a hydroxyl group or a functional group that can be metabolized in a subject to a hydroxyl group; L is a bond or a chemical linker; PTM is capable of binding to Estrogen Related Receptor alpha (ERRα), wherein, upon binding of the EERα to the compound, the ERRα is ubiquitinated by an ubiquitin ligase; ULM is chemically linked to L; and L is chemically linked to PTM; or a pharmaceutically acceptable salt, enantiomer, stereoisomer, solvate, polymorph or prodrug thereof.

In certain embodiments, the compound is L is $-A_1 \ldots A_q-$; wherein $A_1$ to $A_q$ are each independently selected from the group consisting of a bond, $CR^{L1}R^{L2}$, O, S, S=O, S(=O)$_2$, $NR^{L3}$, S(=O)$_2NR^{L3}$, S(=O)$NR^{L3}$, C(=O)$NR^{L3}$, $NR^{L3}$C(=O)$NR^{L4}$, $NR^{L3}$S(=O)$_2NR^{L4}$, C(=O), $CR^{L1}$=$CR^{L2}$, C≡C, $SiR^{L1}R^{L2}$, P(=O)$R^{L1}$, P(=O)$OR^{L1}$, $NR^{L3}$C(=N—CN)$NR^{L4}$, $NR^{L3}$C(=N—CN), $NR^{L3}$C(=C—NO$_2$)$NR^{L4}$, $C_{3-11}$ cycloalkyl optionally substituted with 0-6 substituents selected from the group consisting of $R^{L1}$ and $R^{L2}$, $C_{3-11}$ heterocyclyl optionally substituted with 0-6 substituents selected from the group consisting of $R^{L1}$ and $R^{L2}$, aryl optionally substituted with 0-6 substituents selected from the group consisting of $R^{L1}$ and $R^{L2}$, and heteroaryl optionally substituted with 0-6 substituents selected from the group consisting of $R^{L1}$ and $R^{L2}$, wherein: $R^{L1}$ and $R^{L2}$ each independently can be linked to other A groups to form a cycloalkyl or heterocyclyl moeity that can be further optionally substituted with 0-4 $R^{L5}$ groups; $R^{L1}$, $R^{L2}$, $R^{L3}$, $R^{L4}$ and $R^{L5}$ are each independently selected from the group consisting of H, halo, $C_{1-8}$ alkyl, O($C_{1-8}$ alkyl), S($C_{1-8}$ alkyl), NH($C_{1-8}$ alkyl), N($C_{1-8}$ alkyl)$_2$, $C_{3-11}$ cycloalkyl, aryl, heteroaryl, $C_{3-11}$ heterocyclyl, O($C_{1-8}$ cycloalkyl), S($C_{1-8}$ cycloalkyl), NH($C_{1-8}$ cycloalkyl), N($C_{1-8}$ cycloalkyl)$_2$, N($C_{1-8}$ cycloalkyl)($C_{1-8}$ alkyl), OH, NH$_2$, SH, SO$_2$($C_{1-8}$ alkyl), P(=O)(O$C_{1-8}$ alkyl)($C_{1-8}$ alkyl), P(=O)(O$C_{1-8}$ alkyl)$_2$, C≡C—($C_{1-8}$ alkyl), C≡CH, CH=CH($C_{1-8}$ alkyl), C($C_{1-8}$ alkyl)=CH($C_{1-8}$ alkyl), C($C_{1-8}$ alkyl)=C($C_{1-8}$ alkyl)$_2$, Si(OH)$_3$, Si($C_{1-8}$ alkyl)$_3$, Si(OH)($C_{1-8}$ alkyl)$_2$, C(=O)($C_{1-8}$ alkyl), CO$_2$H, halogen, CN, CF$_3$, CHF$_2$, CH$_2$F, NO$_2$, SF$_5$, SO$_2$NH($C_{1-8}$ alkyl), SO$_2$N($C_{1-8}$ alkyl)$_2$, S(=O)NH($C_{1-8}$ alkyl), S(=O)N($C_{1-8}$alkyl)$_2$, C(=O)NH($C_{1-8}$ alkyl), C(=O)N($C_{1-8}$ alkyl)$_2$, N($C_{1-8}$ alkyl)C(=O)NH($C_{1-8}$ alkyl), N($C_{1-8}$ alkyl)C(=O)N($C_{1-8}$ alkyl)$_2$, NHC(=O)NH ($C_{1-8}$ alkyl), NHC(=O)N($C_{1-8}$ alkyl)$_2$, NHC(=O)NH$_2$, N($C_{1-8}$ alkyl)SO$_2$NH($C_{1-8}$ alkyl), N($C_{1-8}$ alkyl)SO$_2$N($C_{1-8}$ alkyl)$_2$, NHSO$_2$NH($C_{1-8}$ alkyl), NHSO$_2$N($C_{1-8}$ alkyl)$_2$, and NHSO$_2$NH$_2$; and q is an integer greater than or equal to 1.

In certain embodiments, the compound comprises at least one selected from the group consisting of multiple ULMs, multiple PTMs, and multiple Ls.

In certain embodiments, PTM is selected from the group consisting of

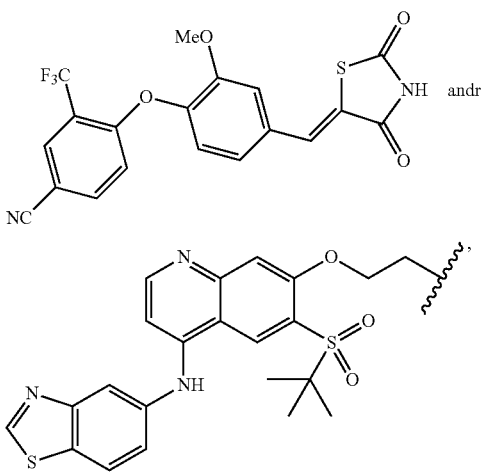 andr or a pharmaceutically acceptable salt, enantiomer, stereoisomer, solvate, polymorph or prodrug thereof.

In certain embodiments, ULM comprises ULM-a:

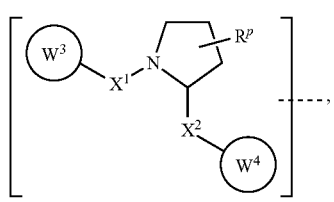 ULM-a wherein the dashed line indicates the attachment of at least one PTM, another ULM (ULM'), or a chemical linker moiety coupling at least one PTM or a ULM' to the other end of the linker; $X^1$, $X^2$ are each independently selected from the group consisting of a bond, O, $NR^{Y3}$, $CR^{Y3}R^{Y4}$, C=O, C=S, SO, and $SO_2$; $R^{Y3}$ and $R^{Y4}$ are each independently selected from the group consisting of H, $C_{1-6}$ alkyl, wherein the alkyl group is linear or branched, and the alkyl group is further optionally substituted by 1 or more substituents independently selected from the group consisting of halo and $C_{1-6}$ alkoxy; the pyrrolidine ring is optionally substituted by 1-3 $R^P$ groups, wherein each $R^P$ is independently selected from the group consisting of H, halo, hydroxy, and $C_{1-3}$ alkyl; $W^3$ is selected from the group consisting of an optionally substituted -T-N($R^{1a}R^{1b}$), -T-aryl, optionally substituted -T-Heteroaryl, optionally substituted -T-Heterocycle, optionally substituted —$NR^1$-T-aryl, optionally substituted —$NR^1$-T-heteroaryl, and optionally substituted —$NR^1$-T-heterocycle, wherein T is covalently bonded to $X^1$; each $R^1$, $R^{1a}$, $R^{1b}$ is independently selected from the group consisting of H, $C_1$-$C_6$ alkyl, $R^{Y3}$C=O, $R^{Y3}$C=S, $R^{Y3}$S=O, $R^{Y3}SO_2$, N($R^{Y3}R^{Y4}$)C=O, N($R^{Y3}R^{Y4}$)C=S, N($R^{Y3}R^{Y4}$)S=O, and N($R^{Y3}R^{Y4}$)$SO_2$, wherein the alkyl group is linear or branched, and the alkyl group is further optionally substituted by 1 or more substituents independently selected from the group consisting of halo and $C_{1-6}$ alkoxy; T is an optionally substituted —$(CH_2)_n$— group, wherein each one of the methylene groups may be optionally substituted with 1-2 substituents selected from the group consisting of halo, $C_1$-$C_6$ alkyl and the sidechain of an amino acid, wherein the alkyl group is linear or branched, and the alkyl group is further optionally substituted by 1 or more substituents independently selected from the group consisting of halo and hydroxy; and n is an integer ranging from 0 to 6; or a pharmaceutically acceptable salt, stereoisomer, solvate, polymorph or prodrug thereof.

In certain embodiments, ULM has the structure:

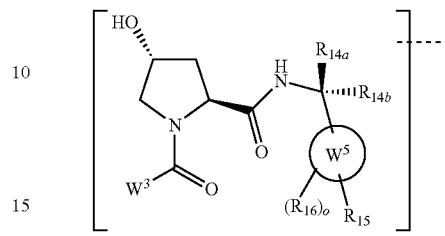

wherein $W^3$ is selected from the group consisting of optionally substituted aryl, optionally substituted heteroaryl, and

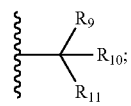

$R_9$ and $R_{10}$ are each independently selected from the group consisting of hydrogen, optionally substituted alkyl, optionally substituted cycloalkyl, optionally substituted hydroxyalkyl, optionally substituted heteroaryl, and haloalkyl; or $R_9$, $R_{10}$ and the carbon atom to which they are attached form an optionally substituted cycloalkyl; $R_{11}$ is selected from the group consisting of optionally substituted heterocyclic, optionally substituted alkoxy, optionally substituted heteroaryl, optionally substituted aryl,

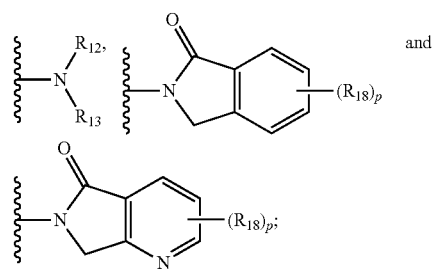 and $R_{12}$ is selected from the group consisting of H and optionally substituted alkyl; $R_{13}$ is selected from the group consisting of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, and optionally substituted aralkyl; $R_{14a}$ and $R_{14b}$ are each independently selected from the group consisting of H, haloalkyl, and optionally substituted alkyl; $W^5$ is selected from the group consisting of phenyl and a 5-10 membered heteroaryl, $R_{15}$ is selected from the group consisting of H, halogen, CN, OH, $NO_2$, $NR_{14a}R_{14b}$, $OR_{14a}$, C(=O)$NR_{14a}R_{14b}$, $NR_{14a}$C(=O)$R_{14b}$, S(=O)$_2NR_{14a}R_{14b}$, $NR_{14a}$S(=O)$_2R_{14b}$, optionally substituted alkyl, optionally substituted haloalkyl, optionally substituted haloalkoxy; aryl, heteroaryl, cycloalkyl, and cycloheteroalkyl; each $R_{16}$ is independently selected from the group consisting of halo, optionally substituted alkyl, optionally substituted haloalkyl, hydroxy, and optionally substituted haloalkoxy; o is 0, 1, 2, 3, or 4; each $R_{18}$ is independently selected from the group consisting of halo, optionally substituted alkoxy, cyano, optionally substituted alkyl, haloalkyl, haloalkoxy and a linker; and p is 0, 1, 2, 3, or 4 or a pharmaceutically acceptable salt, stereoisomer, solvate, polymorph or prodrug thereof.

In certain embodiments, ULM comprises:

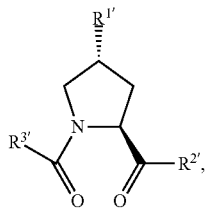

wherein $R^{1'}$ is —OH; $R^{2'}$ is a —NH—CH$_2$-Aryl-HET; $R^{3'}$ is selected from the group consisting of optionally substituted alkyl, —(CH)$R^{CR3'}$—NH—C(=O)—$R^{3P1}$ and —(CH)$R^{CR3'}$—$R^{3P2}$; $R^{CR3'}$ is optionally substituted C$_1$-C$_4$ alkyl; $R^{3P1}$ is selected from the group consisting of optionally substituted C$_1$-C$_6$ alkyl, optionally substituted oxetane, —(CH$_2$)$_n$OCH$_3$ wherein n is 1 or 2, optionally substituted phenyl, and morpholino linked to the carbonyl at the 2- or 3-position; $R^{3P2}$ is selected from the group consisting of

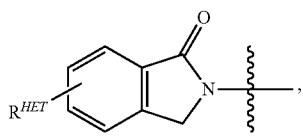

and optionally substituted aryl; HET is selected from the group consisting of optionally substituted thiazole, oxazole, isoxazole and isothiazole; $R^{HET}$ is selected from the group consisting of H, halo, CN, optionally substituted C$_1$-C$_6$ alkyl, optionally substituted C$_1$-C$_6$ alkoxy, and optionally substituted aryl; and the ULM group is covalently bonded to a linker group to which is attached a PTM group, or a pharmaceutically acceptable salt, stereoisomer, solvate or polymorph thereof.

In certain embodiments, ULM is selected from the group consisting of:

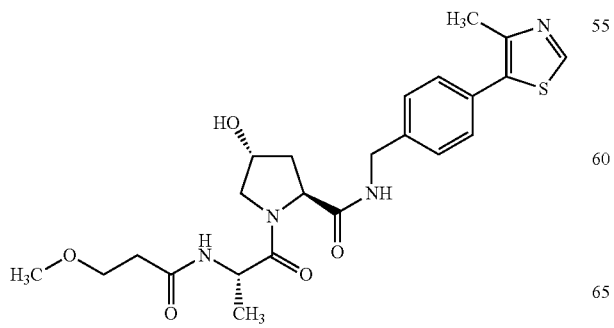

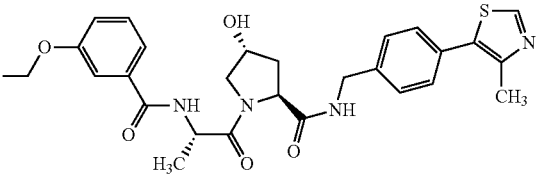

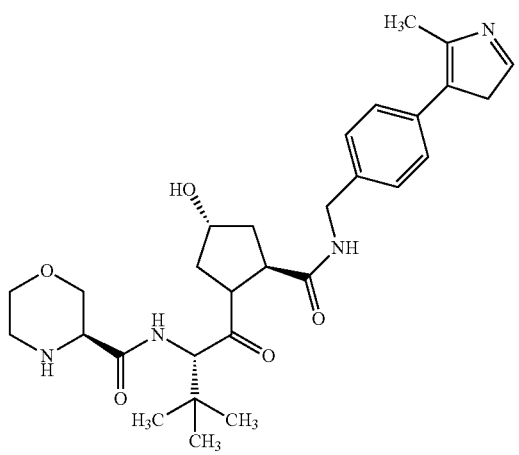

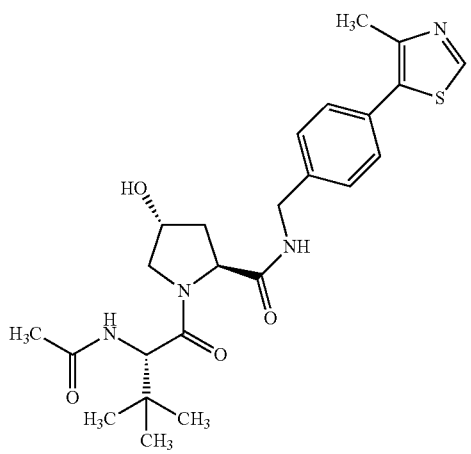

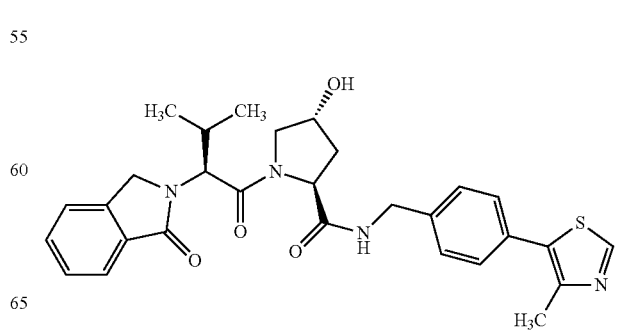

-continued

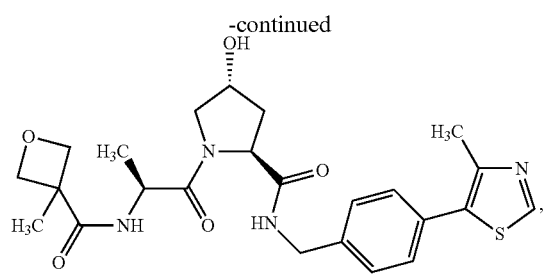

-continued

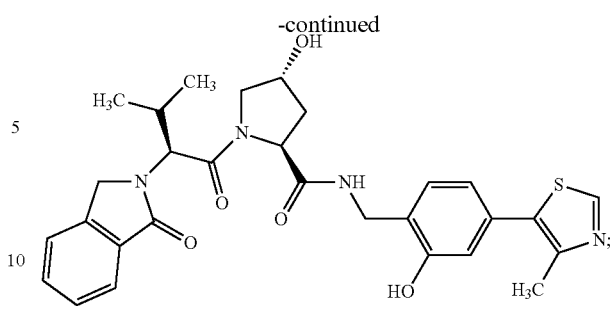

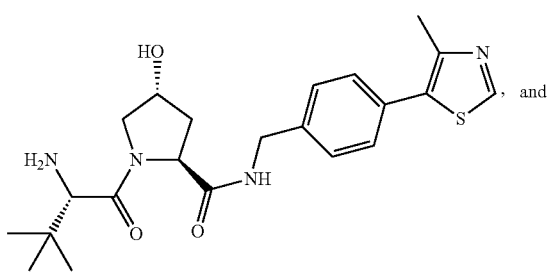
and wherein the ULM group is covalently bonded to the L group to which is attached the PTM group, or a pharmaceutically acceptable salt, stereoisomer, solvate, polymorph or prodrug thereof.

In certain embodiments, L is a polyethyleneglycol optionally substituted with aryl or phenyl, and having from 1 to 100 ethylene glycol units. In other embodiments, L is a polyethylene group optionally substituted with aryl or phenyl, and having from 1 to 10 ethylene glycol units.

In certain embodiments, the compound is selected from the group consisting of:

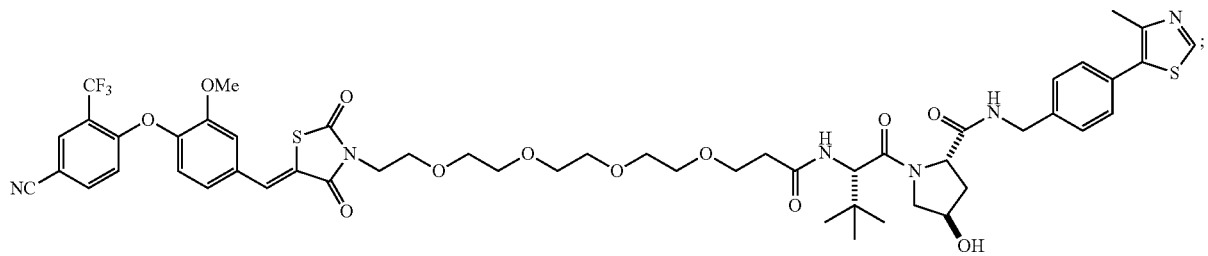

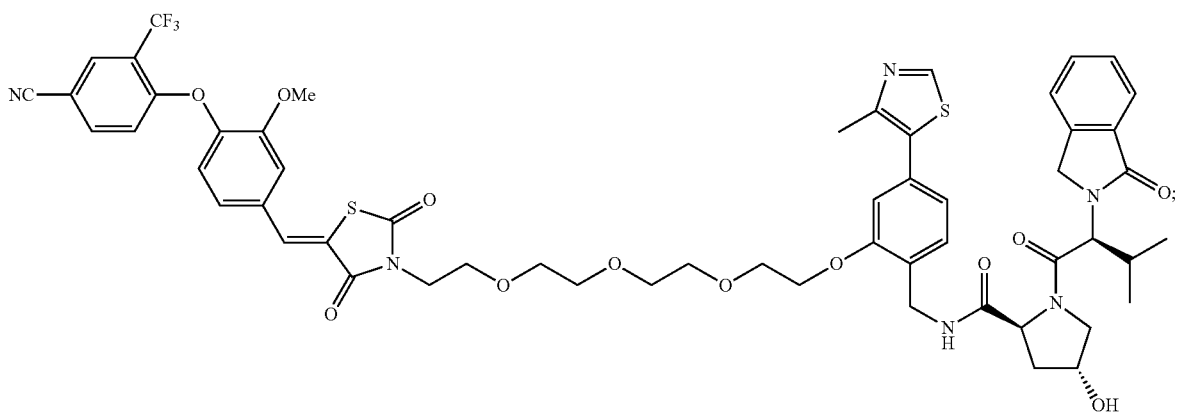

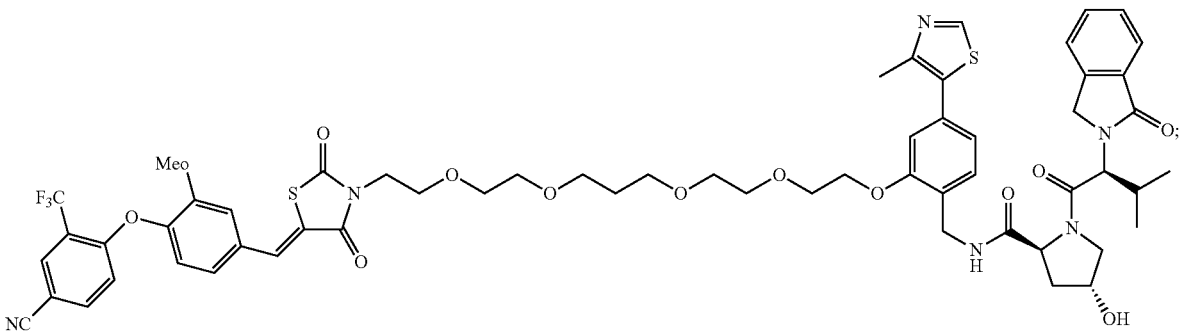

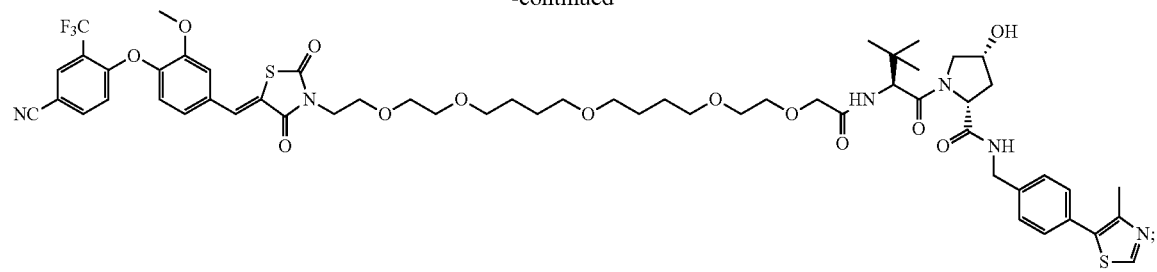
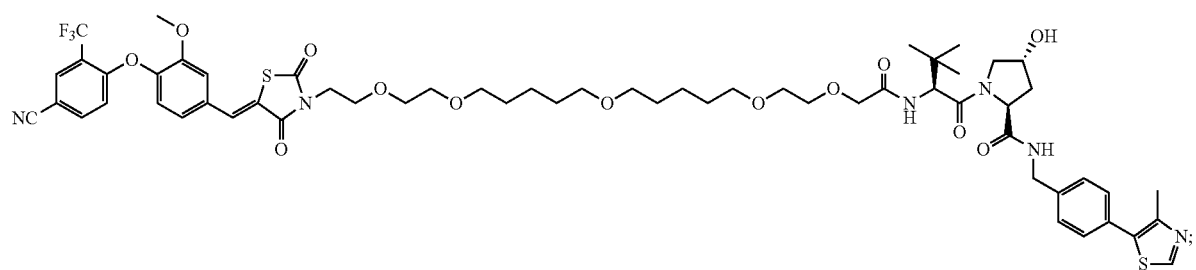
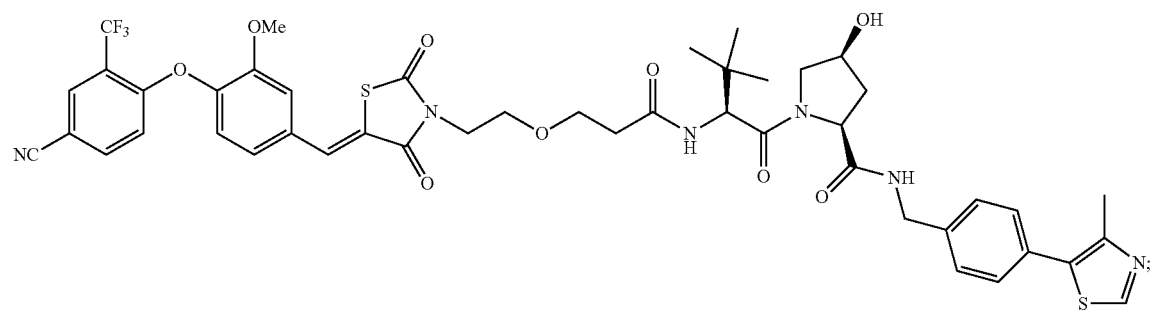
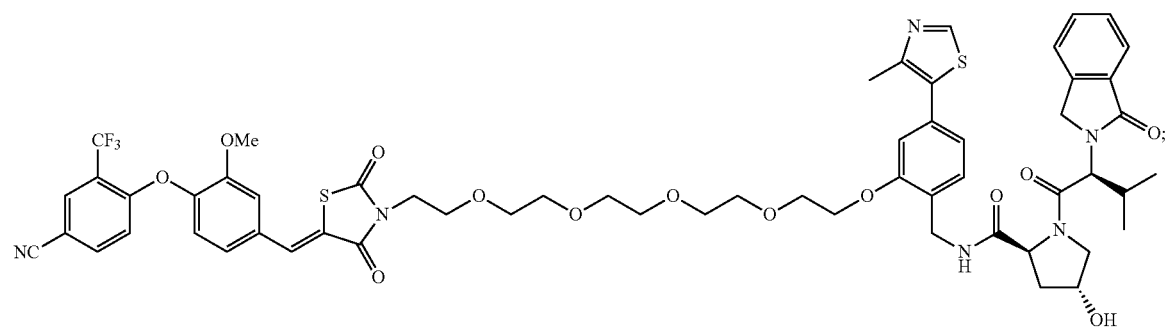
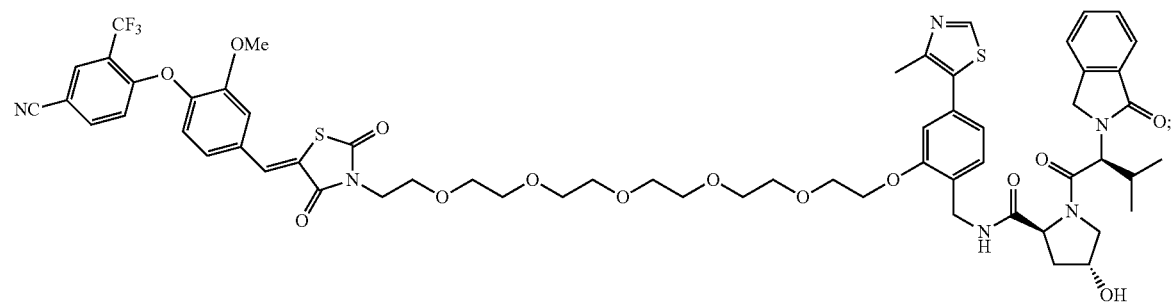

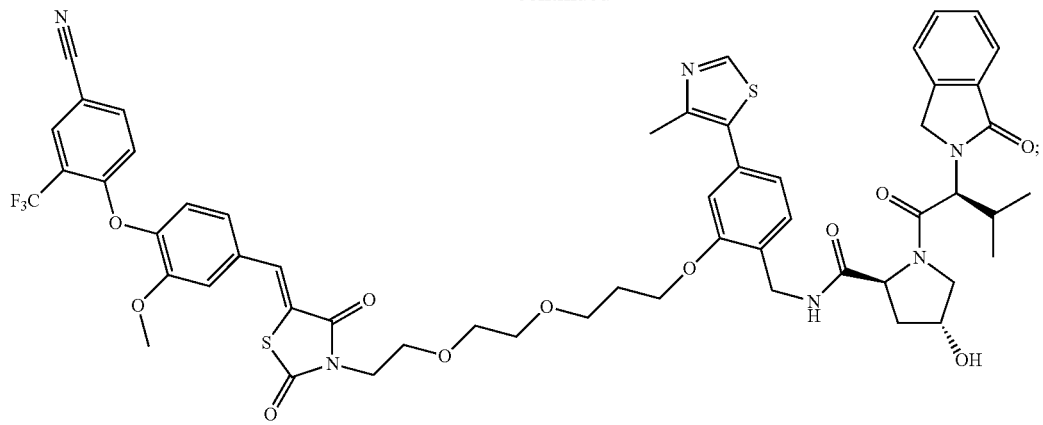
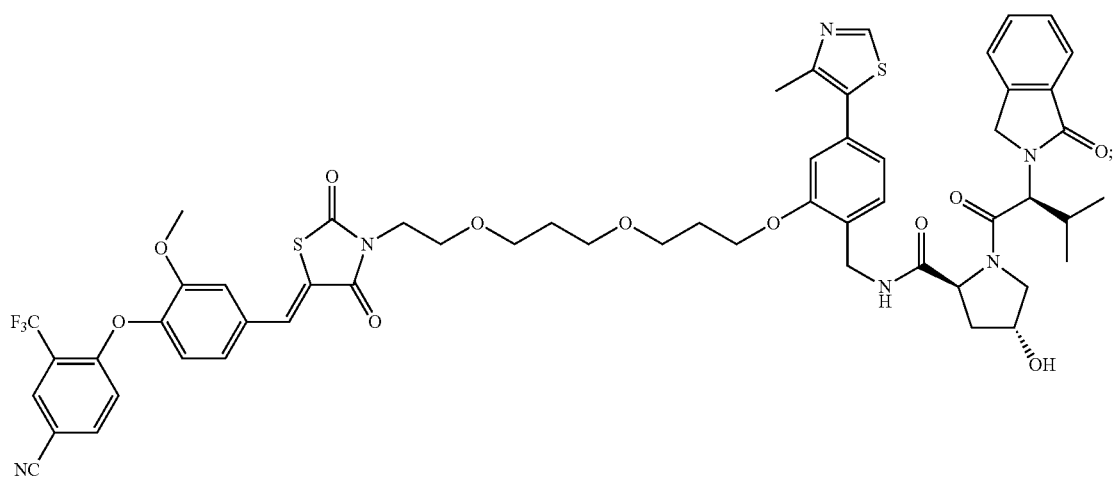
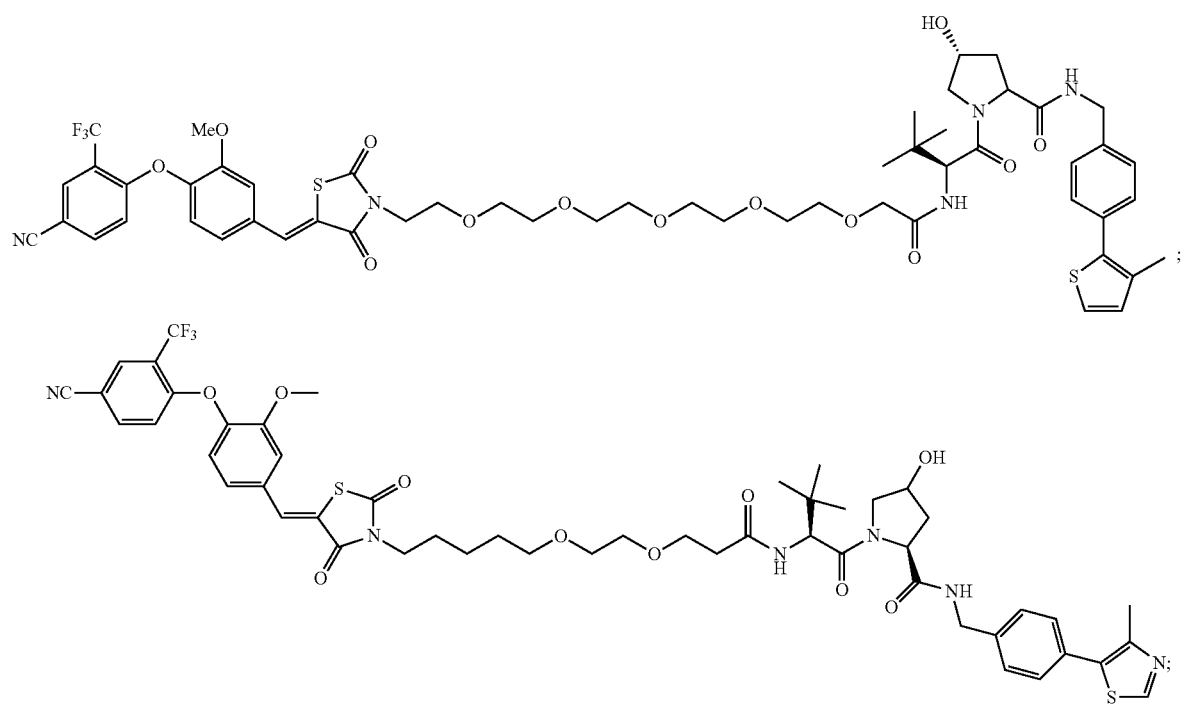

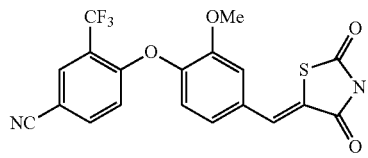 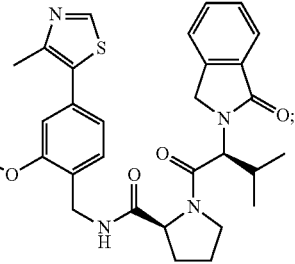
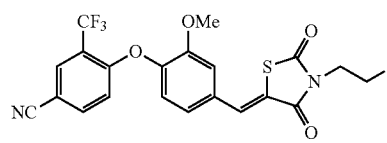 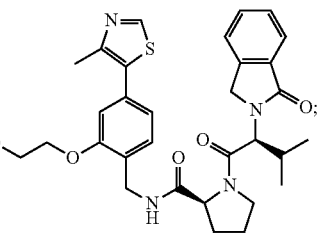
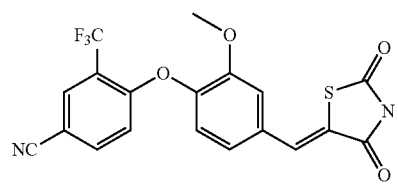 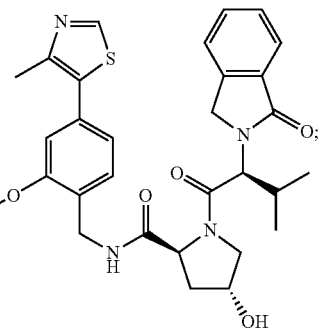
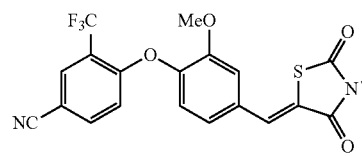 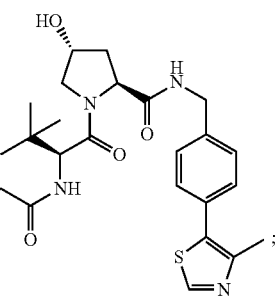
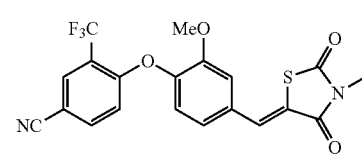 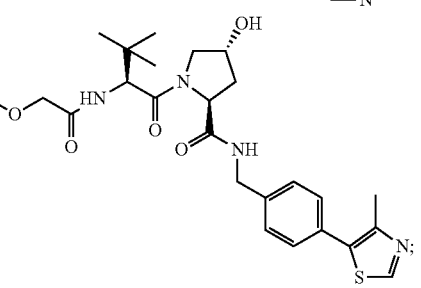
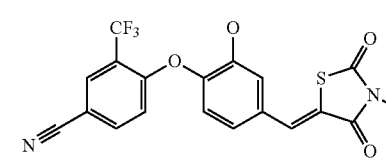 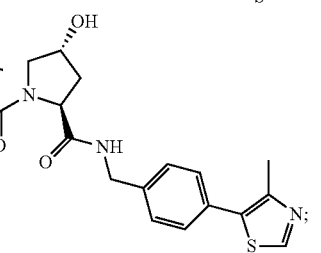

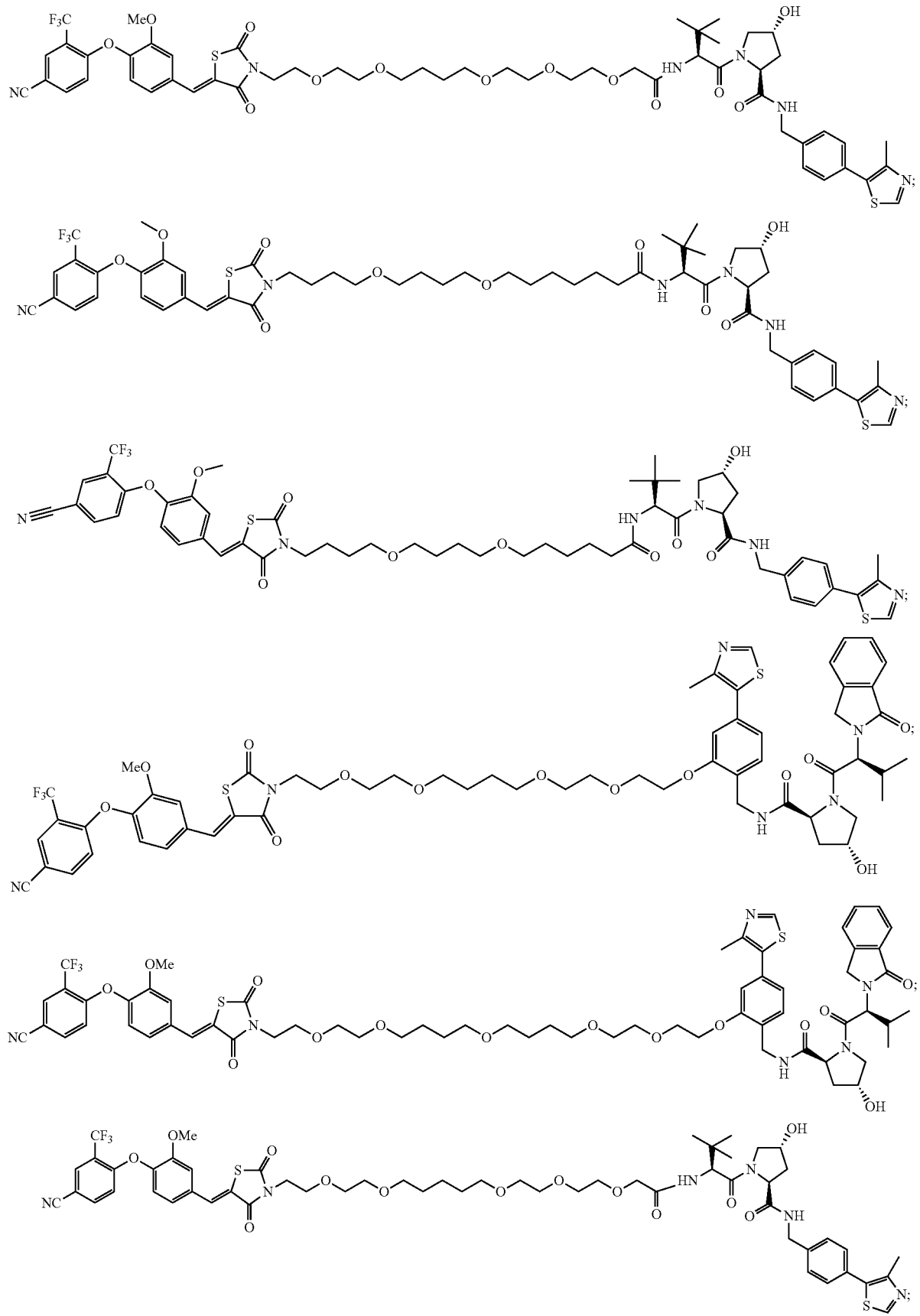

-continued
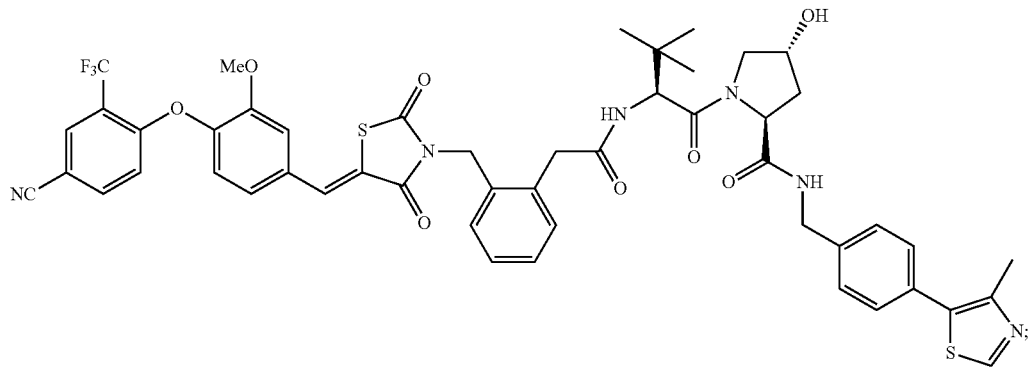
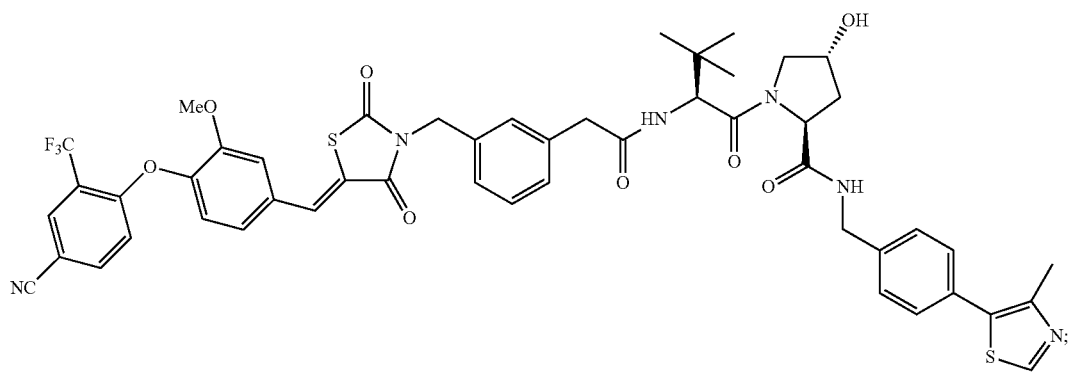
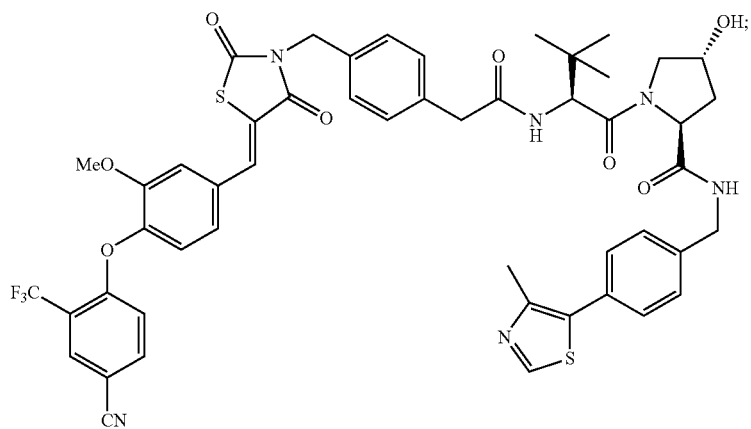
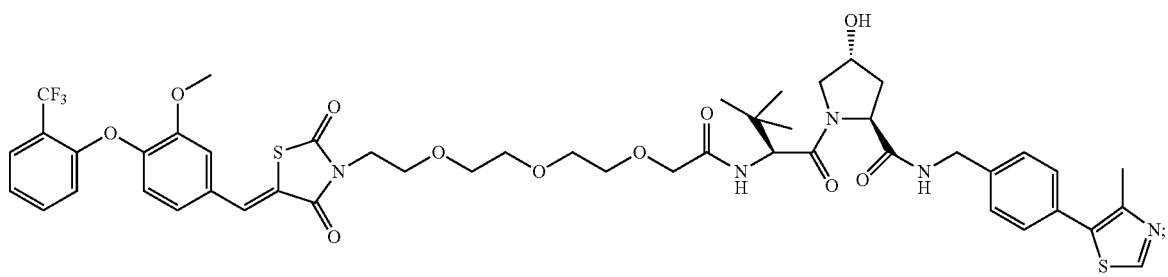

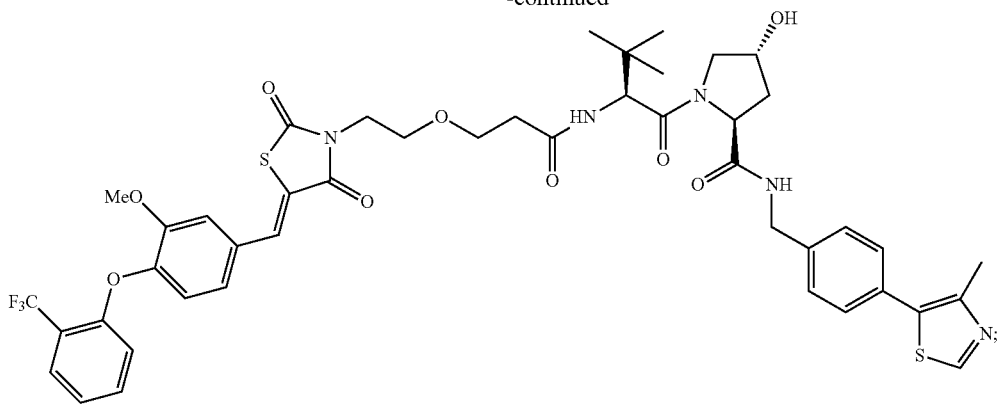

or a pharmaceutically acceptable salt, enantiomer, diasteromer, solvate, polymorph or prodrug thereof.

The invention further provides a pharmaceutical composition comprising an effective amount of at least one compound of the invention, further comprising a pharmaceutically acceptable carrier, additive or excipient, and optionally further comprising an additional bioactive agent. In certain embodiments, the additional bioactive agent is an anticancer agent.

The invention further provides a method for regulating protein activity of a target protein in a subject in need thereof, the method comprising administering to the subject a therapeutically effective amount of at least one compound of the invention. In certain embodiments, the target protein comprises estrogen related receptor alpha (ERR-α).

The invention further provides a method of treating a disease state or condition in a subject in need thereof, wherein dysregulated activity of a protein is responsible for the disease state or condition, the method comprising administering to the subject an effective amount of at least one compound of the invention, wherein the compound modulates the amount or activity of the protein in the subject. In certain embodiments, the disease state or condition comprises cancer. In other embodiments, the cancer is selected from the group consisting of squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. In yet other embodiments, the cancer is selected from the group consisting of T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL, Philadelphia chromosome positive CML, prostate cancer, Kennedy's Disease, breast cancer, Lymphoma, diabetes, diabetes mellitus type I, diabetes mellitus type II, obesity, colorectal cancer, head & neck cancer, immune system disorders, leukemia, stem cell growth, stem cell transplantation, wound healing, atherosclerosis, hepatocellular carcinoma, endometrial cancer, McCune-Albright Syndrome, adenocarcinoma, acute lymphoblastic leukemia, multiple myeloma myeloproliferative diseases, large B-cell lymphoma, and B cell Lymphoma.

The invention further provides a method of degrading a target protein in a cell, the method comprising contacting the cell with an effective amount of at least one compound of the invention, wherein the compound effectuates the degradation of the target protein in the cell.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which:

FIG. 3A: (A) n=2 and n=4. FIG. 3B: n=3. FIG. 3C: comparison of n=0, (PROTAC5), n=1 (PROTAC6), n=2 (PROTAC7), n=3 (PROTAC3), and n=5 (PROTAC4).

FIG. 5 depicts the lack of effect of

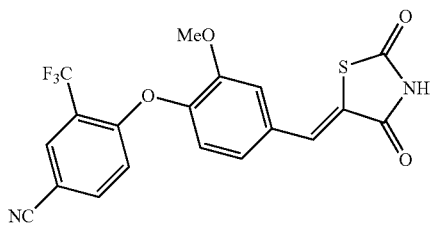 [SMILES: COc1cc(/C=C2\SC(=O)NC2=O)ccc1Oc1ccc(C#N)cc1C(F)(F)F]

on the degradation of estrogen related receptor alpha (ERRα).

Figure 6:
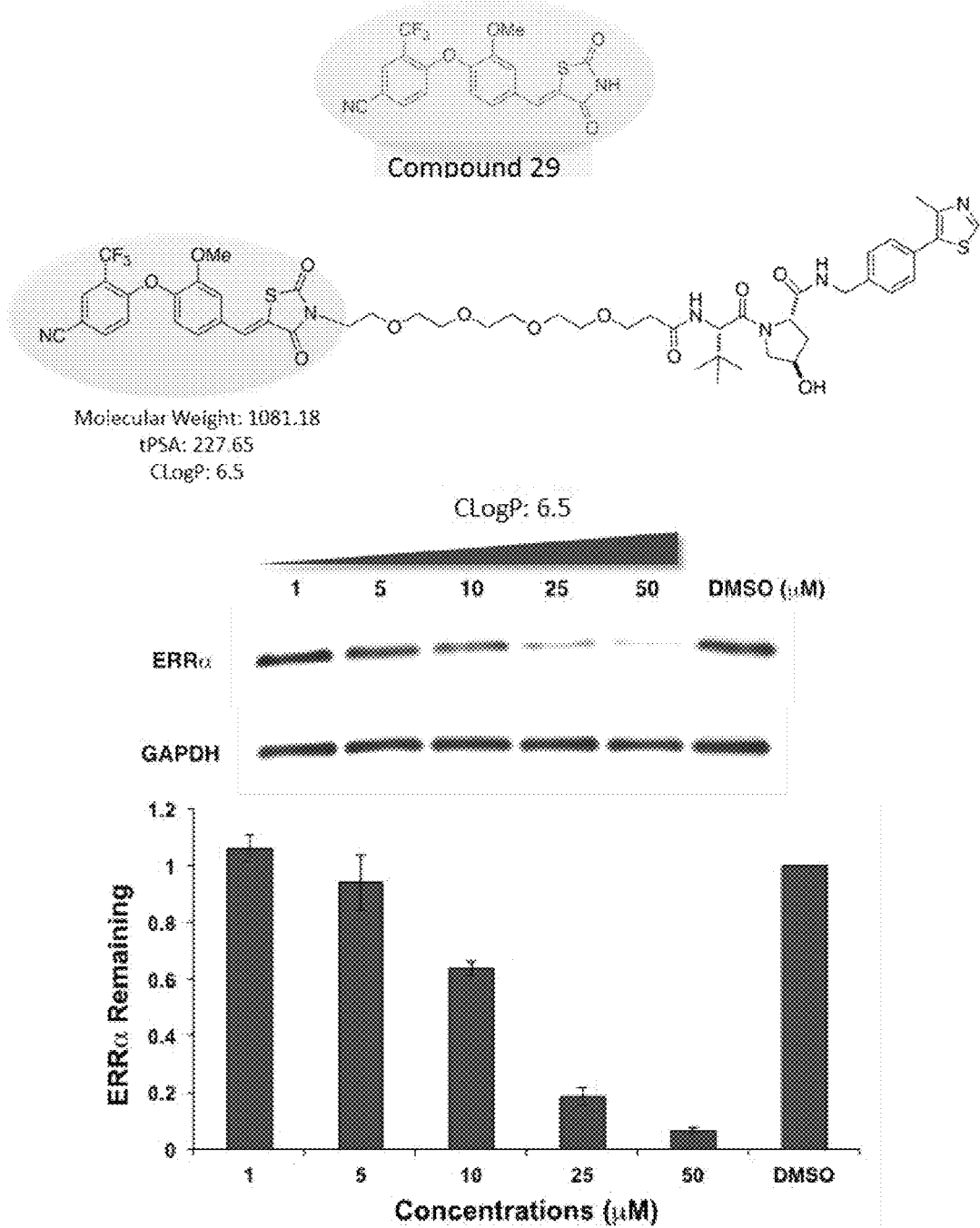

FIG. 6 depicts the PROTAC-mediated ERRα degradation employing

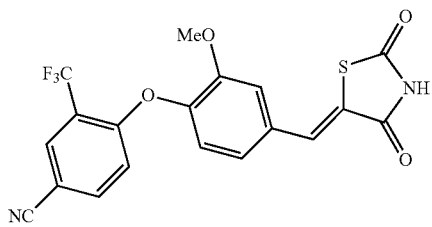 [SMILES: COc1cc(/C=C2\SC(=O)NC2=O)ccc1Oc1ccc(C#N)cc1C(F)(F)F]

as the ERRα ligand.

Figure 7:
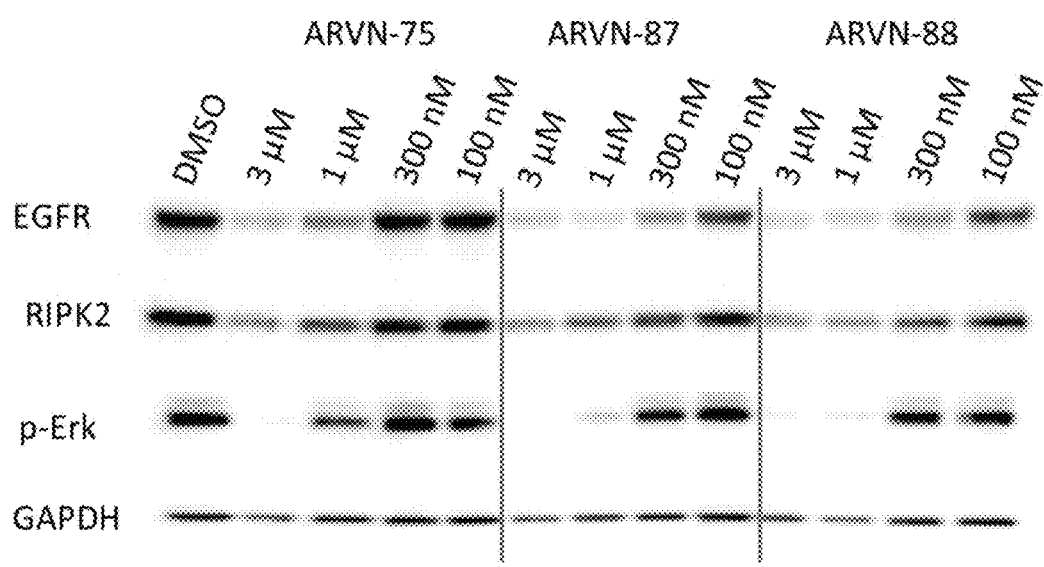

FIG. 7 depicts the PROTAC-mediated EGFR and RIPK2 receptor degradation, illustrating the finding that PROTACs work on cytosolic and receptor kinases.

Figure 8A:
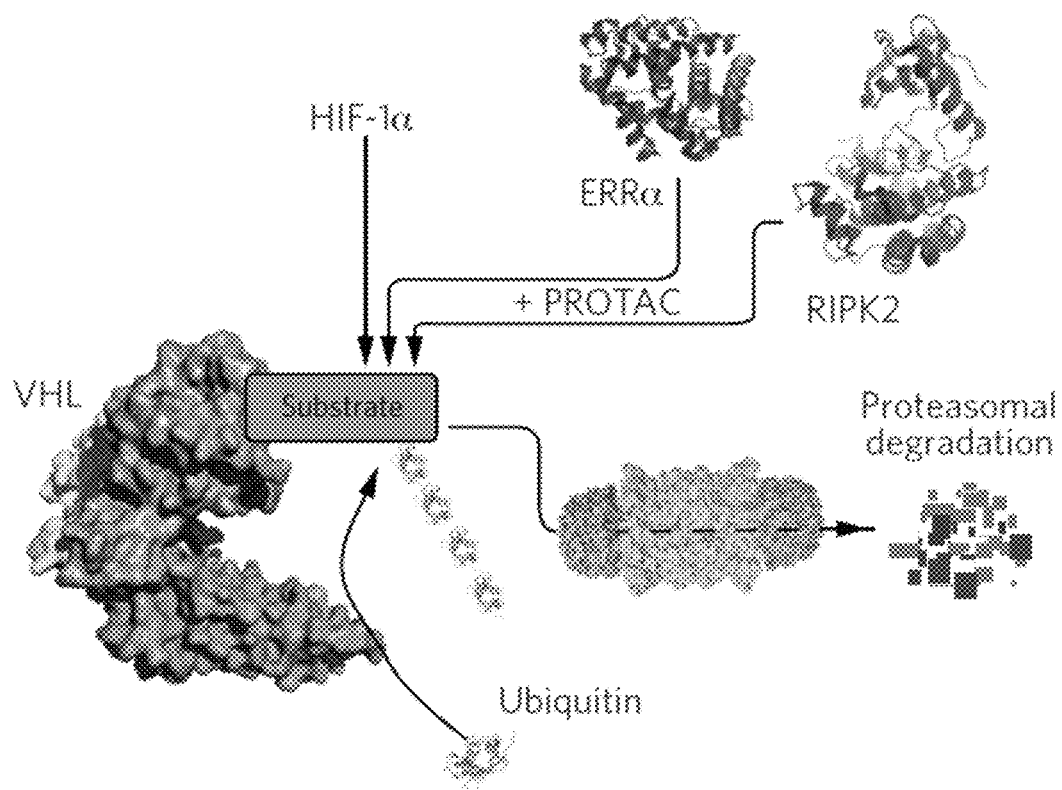
Figure 8B:
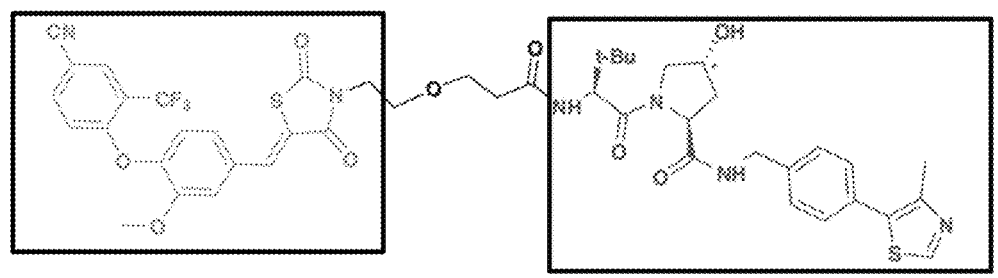
Figure 8C:
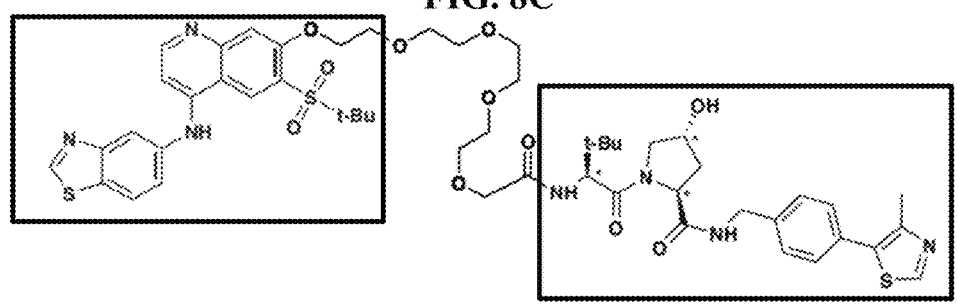

FIG. 8A depicts the proposed model of PROTAC-induced degradation. FIG. 8B depicts the structure of PROTAC_ERRα (1) with the ERRα ligand shown in orange (left box) and the modular VHL ligand in blue (right box), with asterisks indicating stereocenter(s) whose inversion (in PROTAC_ERRα_epi) abolishes VHL binding. FIG. 8C depicts the structure of PROTAC_RIPK2 (3) with the RIPK2 ligand shown in green (left box) and the modular VHL ligand in blue (right box).

Figure 9A:
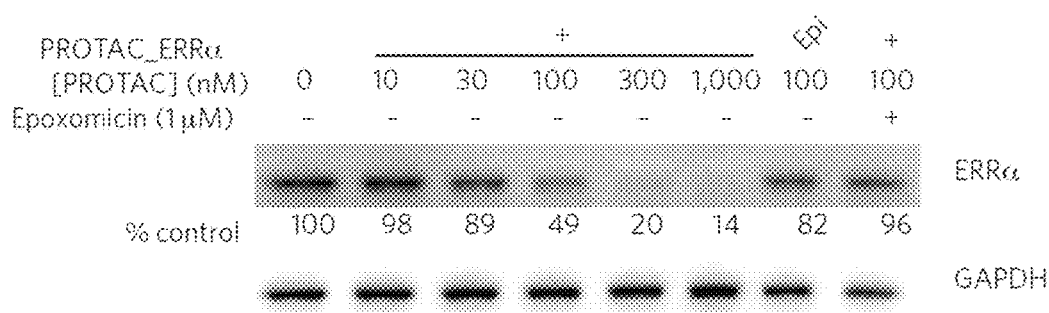
Figure 9B:
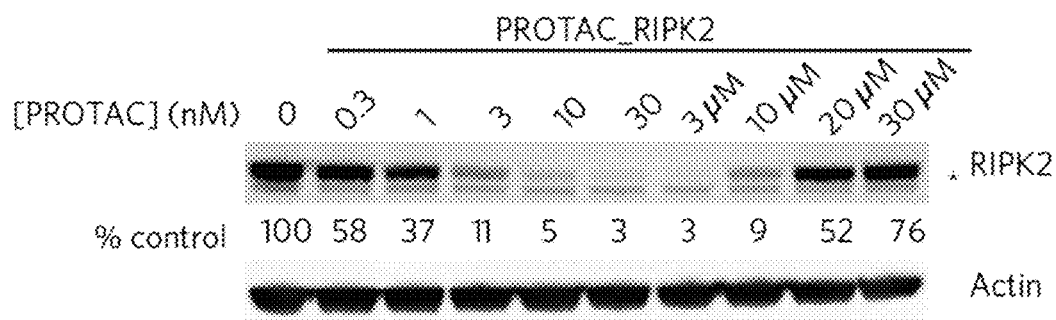
Figure 9C:
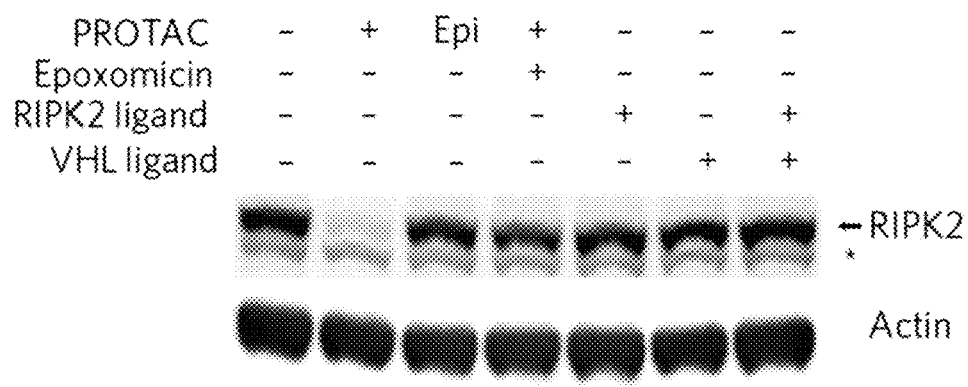
Figure 9D:
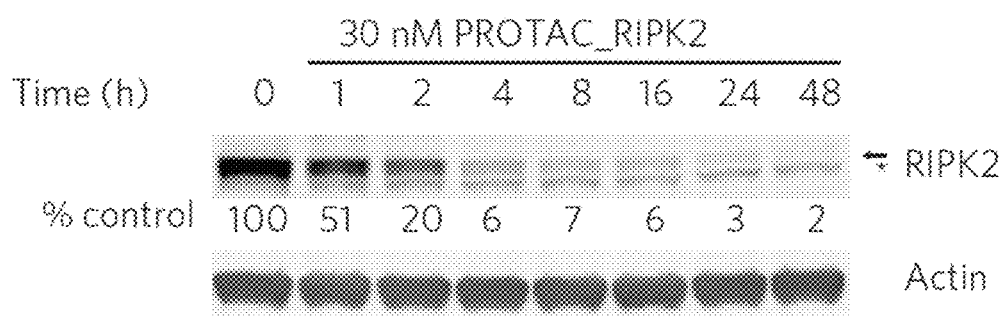
Figure 9E:
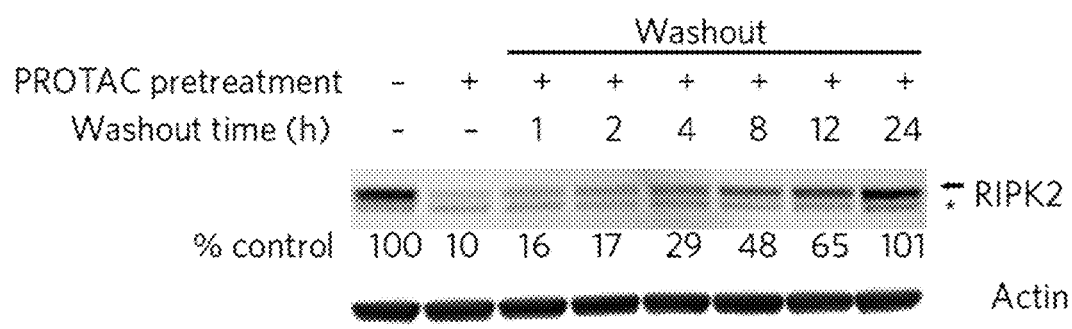

FIGS. 9A-9E depict the ability of PROTACs to down-regulate protein levels. FIG. 9A depicts downregulation of protein levels of ERRα. FIG. 9B depicts downregulation of protein levels of RIPK2; an observed amelioration of efficacy at higher concentrations ('hook effect') is consistent with a ternary complex-mediated mechanism. FIG. 9C illustrates that the ability of PROTACs to downregulate RIPK2 is dependent on the proteasome and the presence of the linkage between both targeting ligands. FIG. 9D depicts dowregulation of protein levels of RIPK2 by PROTAC_RIPK2. FIG. 9E: FIG. 9E depicts ability of PROTACs to downregulate proteins reversibly) protein levels reversibly.

Figure 10A:
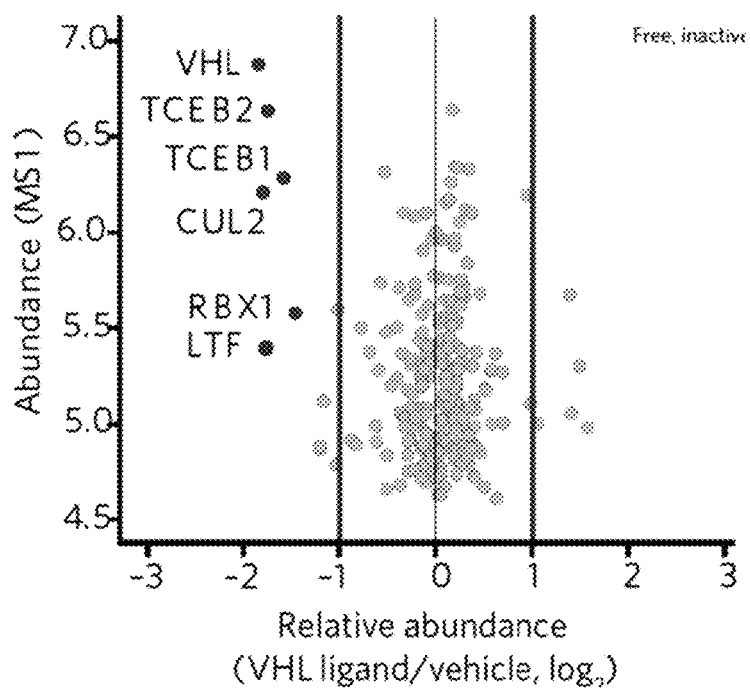
Figure 10B:
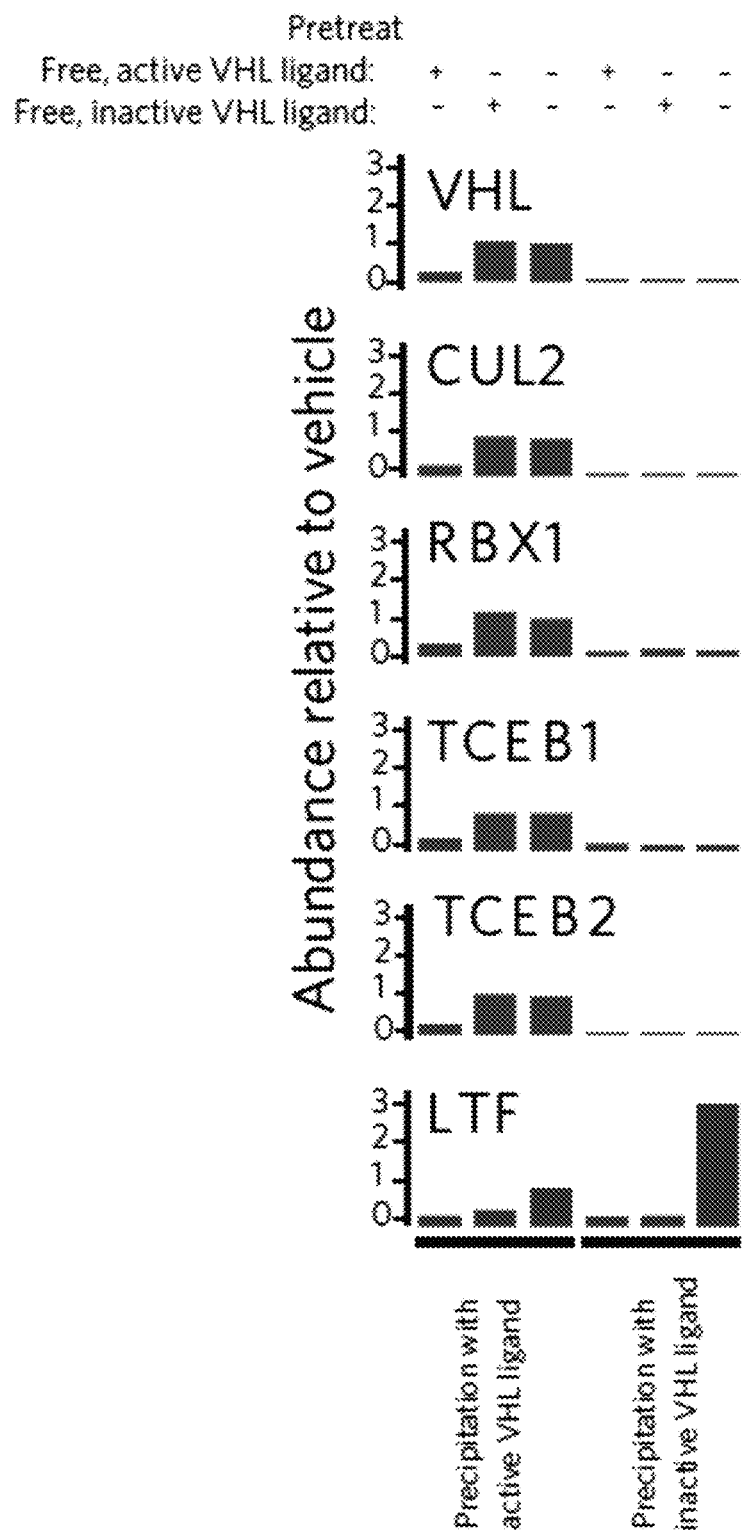
Figure 10C:
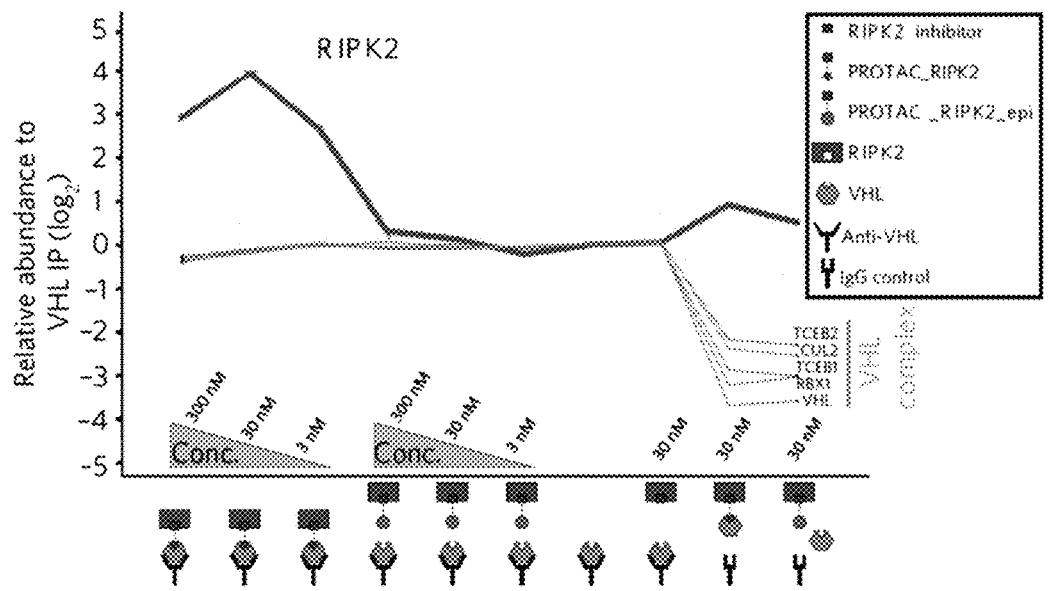
Figure 10D:
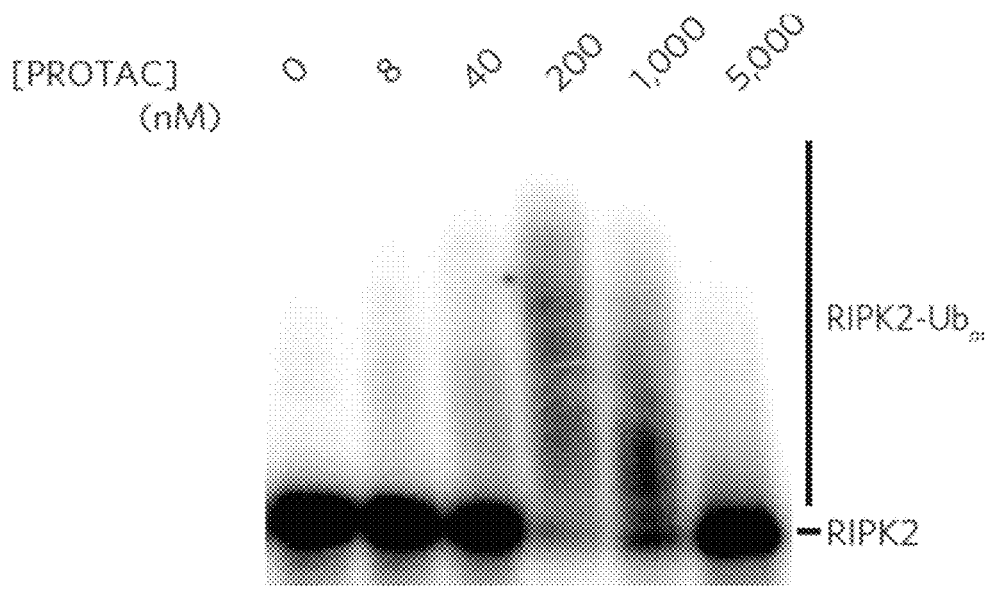
Figure 10E:
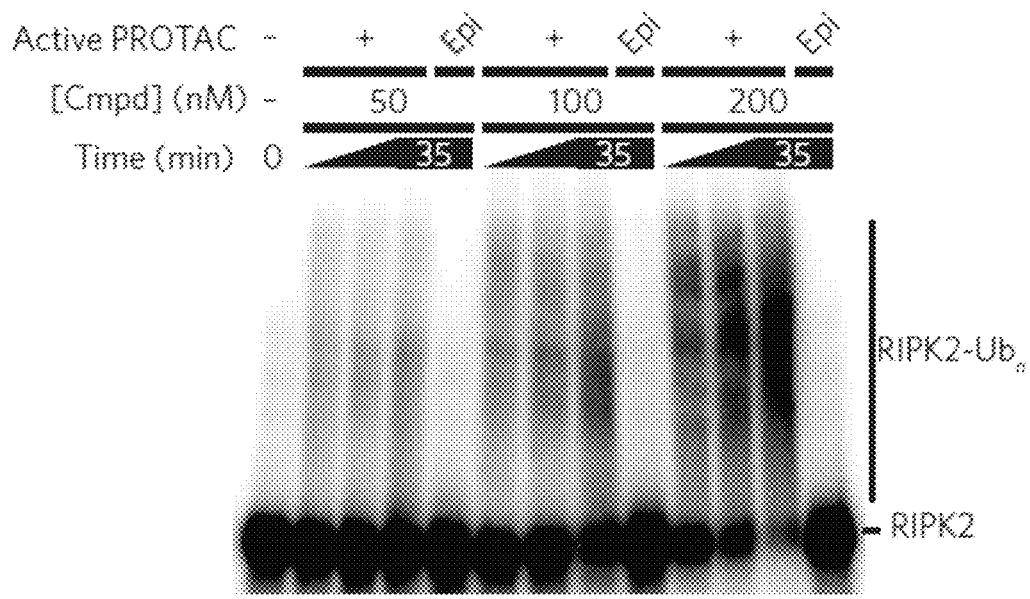
Figure 10F:
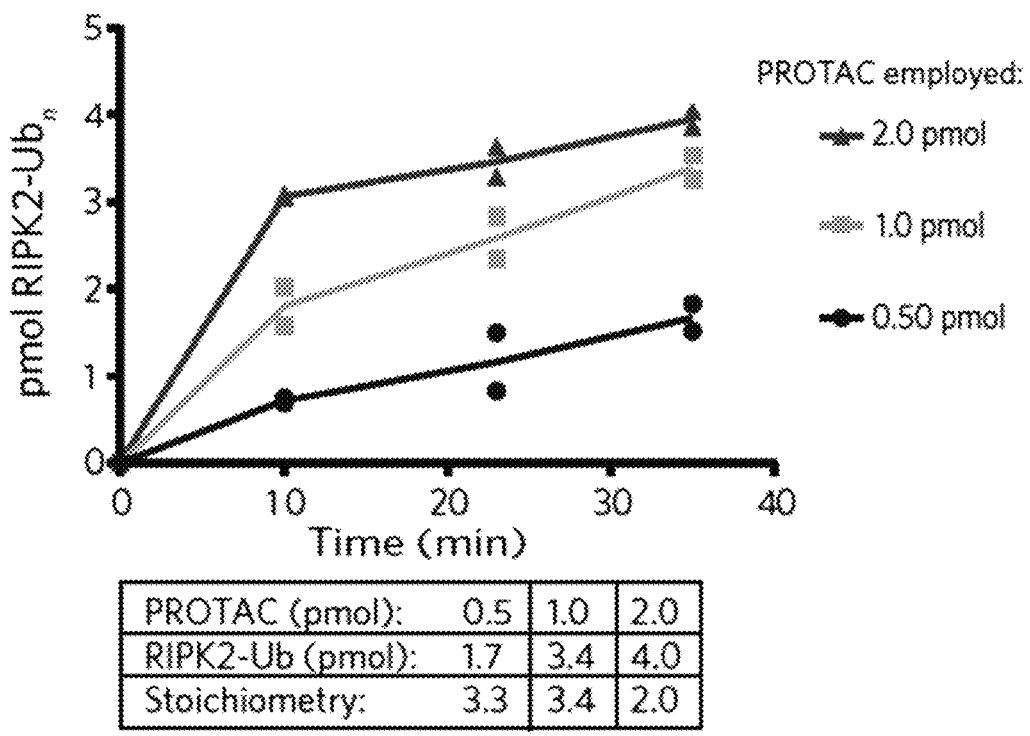

FIG. 10A depicts the selectivity of the VHL ligand for VHL and associated proteins. FIG. 10B the binding selectivity of the VHL ligand to the VHL complex. FIG. 10C depicts the co-immunoprecipitation of VHL and RIPK2 by PROTAC_RIPK2. FIG. 10D depicts the in vitro RIPK2 ubiquitination by PROTAC_RIPK2. FIG. 10E depicts the increase in the rate of ubiquitination with increasing PROTAC concentration. FIG. 10F depicts the ability of PROTACs to induce super-stoichiometric ubiquitination of RIPK2.

Figure 11A:
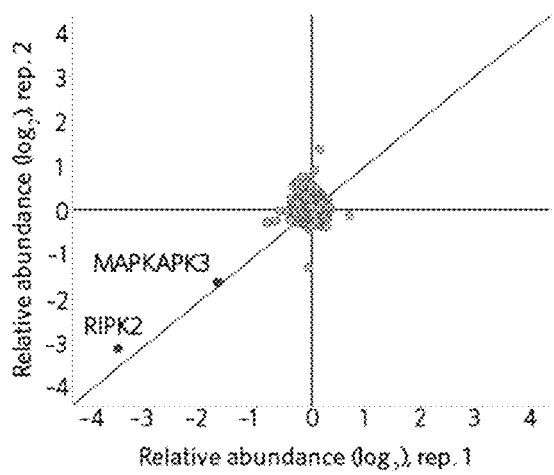
Figure 11B:
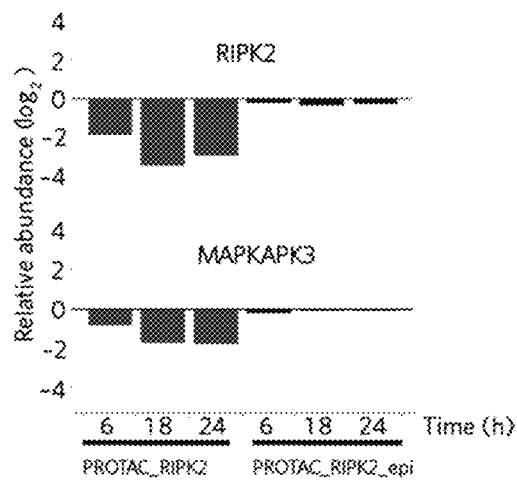
Figure 11C:
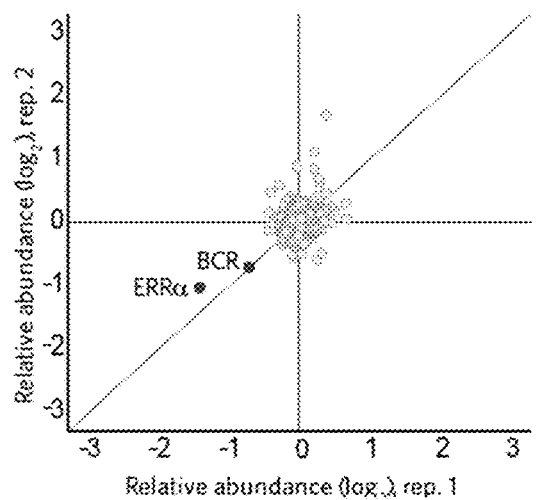
Figure 11D:
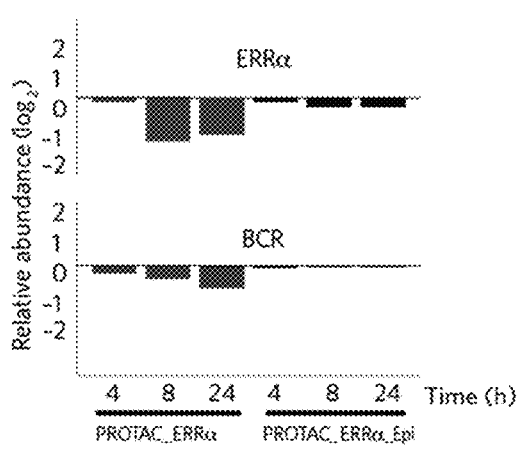

FIG. 11A depicts the selectivity of PROTAC_RIPK2 for RIPK2 degradation. FIG. 11B depicts the quantified levels of RIPK2 and MAPKAPK3 in THP-1 cells treated with either PROTAC_RIPK2 or PROTAC_RIPK2_epi. FIG. 11C depicts quantified protein levels from MCF-7 cells treated for 24 h with 500 nM PROTAC_ERRα. FIG. 11D depicts quantified levels of ERRα and BCR from MCF-7 cells treated for the indicated times with 500 nM PROTAC_ERRα.

Figure 12A:
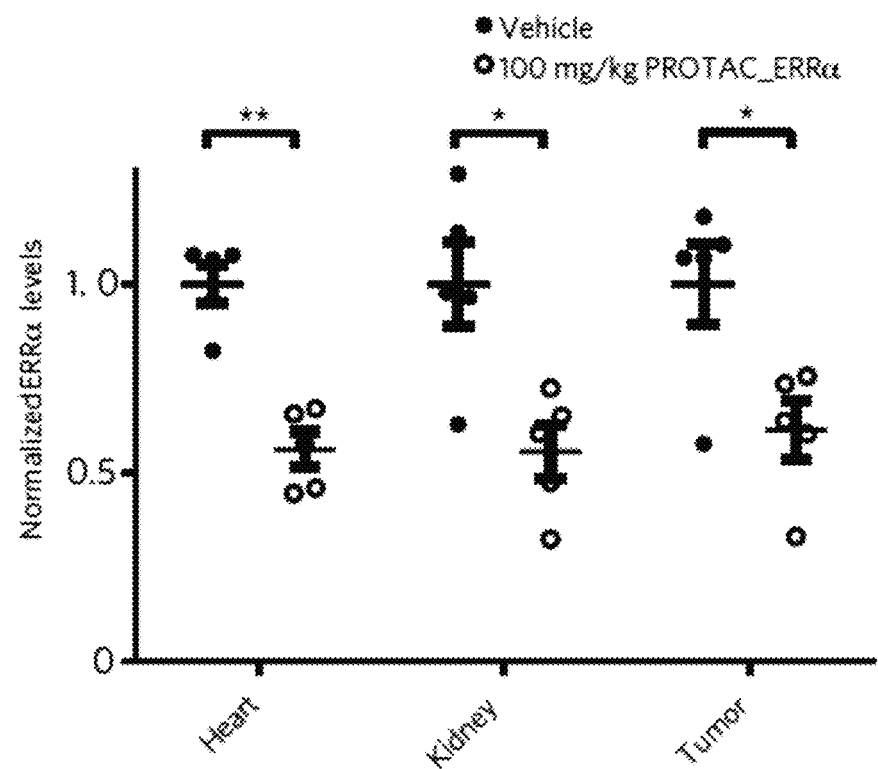
Figure 12B:
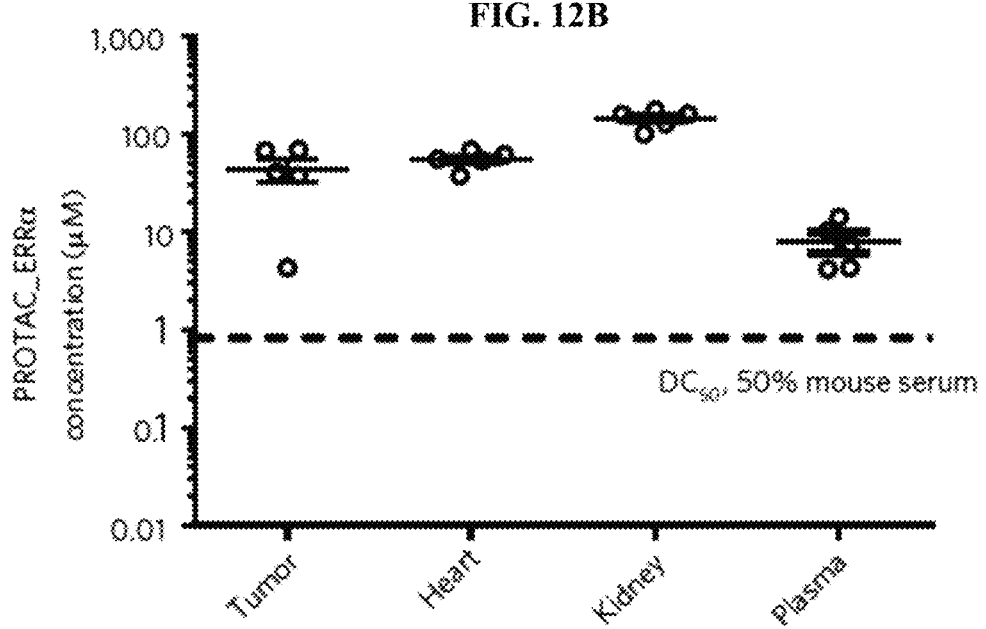

FIG. 12A depicts efficacy data for mice (n=5) injected with either vehicle or 100 mg/kg PROTAC_ERRα (3 times per day, intraperitoneally). FIG. 12B depicts analysis of tissues and plasma from (A) for levels of PROTAC_ERRα by LC/MS.

Figure 13:
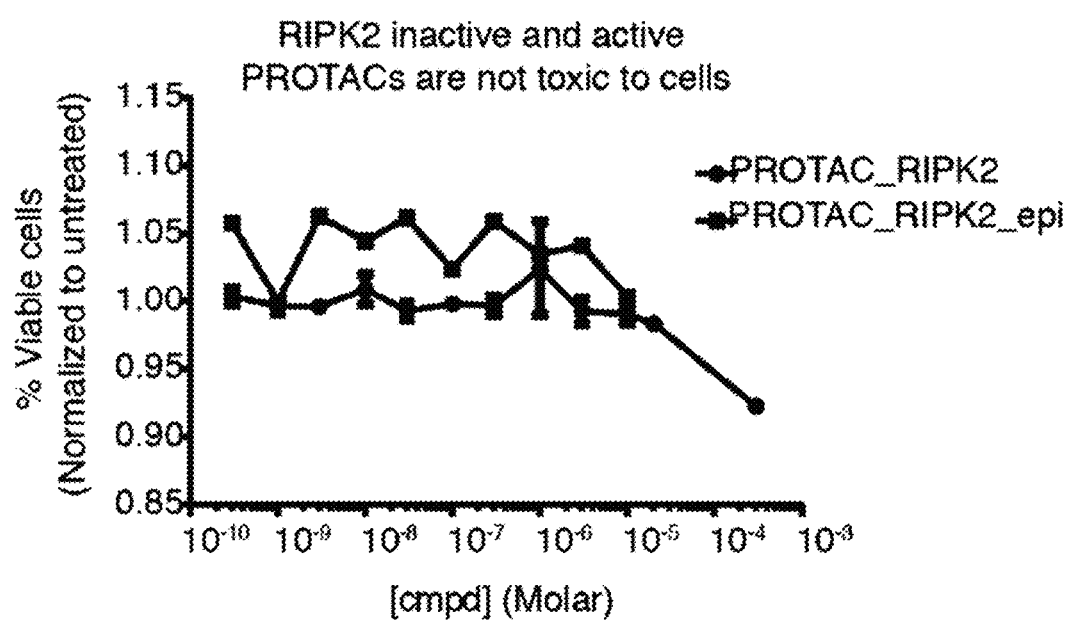

FIG. 13 is a cell viability graph illustrating that PROTAC_RIPK2 is not toxic to cells. THP-1 cells were treated with the indicated concentration sof PROTAC_RIPK2 or PROTAC_RIPK2_epi for 16 hours, followed by a Trypan Blue assay to determine cell viability. Error bars represent mean and S.D.

DETAILED DESCRIPTION OF THE INVENTION

The present description relates to the discovery that an ubiquitin pathway protein ubiquitinates any target protein, once the ubiquitin pathway protein and the target protein are placed in proximity by a chimeric construct that binds the ubiquitin pathway protein (e.g., VHL, cereblon, MDM2 or IAP E3 ligase) and the target protein (e.g., estrogen related receptor alpha (α) or RIPK2). Accordingly, the present invention provides a composition that results in the ubiquitination of a chosen target protein. The present invention also provides a library of compositions and the use thereof.

Definitions

The following terms are used to describe the present invention. In instances where a term is not specifically defined herein, that term is given an art-recognized meaning by those of ordinary skill applying that term in context to its use in describing the present invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder.

When the bond  is shown, both a double bond and single bond are represented within the context of the compound shown.

As used herein, the term "PROTAC" refers to proteolysis targeting chimeras.

The terms "patient" and "subject" are used interchangeably throughout the specification to describe an animal, in certain embodiments a human or a domesticated animal, to whom treatment, including prophylactic treatment, with the compositions according to the present invention is provided. For treatment of those infections, conditions or disease states that are specific for a specific animal such as a human patient, the term patient refers to that specific animal, including a domesticated animal such as a dog or cat or a farm animal such as a horse, cow, sheep, and so forth. In certain embodiments, in the present invention, the term patient refers to a human patient unless otherwise stated or implied from the context of the use of the term.

The term "effective" is used to describe an amount of a compound, composition or component that, when used within the context of its intended use, effects an intended result. The term effective subsumes all other effective amount or effective concentration terms, which are otherwise described or used in the present application.

The term "VCB E3 Ubiquitin Ligase", "Hippel-Lindau E3 Ubiquitin Ligase" or "Ubiquitin Ligase" is used to describe a target enzyme(s) binding site of ubiquitin ligase moieties in the bifunctional (chimeric) compounds according to the present invention. VCB E3 is a protein that, in combination with an E2 ubiquitin-conjugating enzyme, causes the attachment of ubiquitin to a lysine on a target protein; the E3 ubiquitin ligase targets specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first, a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further, different lysines on ubiquitin can be targeted by an E3 to make chains. The most common lysine is Lys48 on the ubiquitin chain, which is used to make polyubiquitin, which is recognized by the proteasome.

The term "protein target moiety" or PTM is used to describe a small molecule that binds to a target protein or other protein or polypeptide of interest and places/presents that protein or polypeptide in proximity to an ubiquitin ligase, such that degradation of the protein or polypeptide by ubiquitin ligase may occur. Non-limiting examples of small molecule target protein binding moieties include estrogen-related receptor alpha (ERRα) binders, RIPK2 binders, AR binders, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein.

The term "target protein" is used to describe a protein or polypeptide, which is a target for binding to a compound according to the present invention and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to ULM groups through linker groups L.

Target proteins that may be bound to the protein target moiety and degraded by the ligase to which the ubiquitin ligase binding moiety is bound include structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others.

More specifically, a number of drug targets for human therapeutics represent protein targets to which protein target moiety may be bound and incorporated into compounds according to the present invention. These include proteins which may be used to restore function in numerous polygenic diseases, including for example ERRα, AR, RIPK2, B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

Haloalkane dehalogenase enzymes are another target of specific compounds according to the present invention. Compounds according to the present invention that contain chloroalkane peptide binding moieties ($C_1$-$C_{12}$ often about $C_2$-$C_{10}$ alkyl halo groups) may be used to inhibit and/or degrade haloalkane dehalogenase enzymes used in fusion proteins or related dioagnostic proteins as described in PCT/US 2012/063401, filed Dec. 6, 2011 and published as WO 2012/078559 on Jun. 14, 2012, the contents of which are incorporated by reference herein.

These various protein targets (e.g., estrogen related receptor alpha (ERRα), AR, or RIPK2) may be used in screens that identify compound moieties that bind to the protein; and by incorporation of the moiety into compounds according to the present invention, the level of activity of the protein may be altered for therapeutic end result.

The term "disease state or condition" is used to describe any disease state or condition wherein protein dysregulation (i.e., the amount of protein expressed in a patient is elevated) occurs and where degradation of one or more proteins (e.g., estrogen related receptor alpha (ERRα), AR, or RIPK2) in a patient may provide beneficial therapy or relief of symptoms to a patient in need thereof. In certain instances, the disease state or condition may be cured.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome, Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis, aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia, Angiokeratoma Corporis Diffusum, Angiomatosis retinae (von Hippel-Lindau disease), Apert syndrome, Arachnodactyly (Marfan syndrome), Stickler syndrome, Arthrochalasis multiplex congenital (Ehlers-Danlos syndrome#arthrochalasia type), ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria, Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita), SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymuller syndrome, Wolf-Hirschhom syndrome, Wolff Periodic disease, Weissenbacher-Zweymuller syndrome and Xeroderma pigmentosum, among others.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers that may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Exemplary bioactive agents for use herein include those agents that have pharmacological activity similar to that for which the present compounds are used or administered and include for example, anti-cancer agents, antiviral agents, especially including anti-HIV agents and anti-HCV agents, antimicrobial agents, antifungal agents, and so forth.

The term "additional anti-cancer agent" is used to describe an anti-cancer agent that be combined with compounds according to the present invention to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR, KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifamib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deooxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "pharmaceutically acceptable salt" is used throughout the specification to describe, where applicable, a salt form of one or more of the compounds described herein that are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly exemplary as neutralization salts of the phosphates according to the present invention.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The term "independently" is used herein to indicate that the variable, which is independently applied, varies independently from application to application.

The term "hydrocarbyl" shall mean a compound that contains carbon and hydrogen and that may be fully saturated, partially unsaturated or aromatic and includes aryl groups, alkyl groups, alkenyl groups and alkynyl groups.

The term "alkyl" shall mean within its context a linear, branch-chained or cyclic fully saturated hydrocarbon radical or alkyl group, in certain embodiments a $C_1$-$C_{10}$, more in certain embodiments a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, compounds according to the present invention which may be used to covalently bind to dehalogenase enzymes. These compounds generally contain a side chain (often linked through a polyethylene glycol group) which terminates in an alkyl group which has a halogen substituent (often chlorine or bromine) on its distil end which results in covalent binding of the compound containing such a moiety to the protein.

The term "unsubstituted" shall mean substituted only with hydrogen atoms. A range of carbon atoms which includes $C_0$ means that carbon is absent and is replaced with H. Thus, a range of carbon atoms that is $C_0$-$C_6$ includes carbons atoms of 1, 2, 3, 4, 5 and 6 and for $C_0$, H stands in place of carbon. The term "substituted" or "optionally substituted" shall mean independently (i.e., where more than substituent occurs, each substituent is independent of another substituent) one or more substituents (independently up to five substitutents, in certain embodiments up to three substituents, often 1 or 2 substituents on a moiety in a compound according to the present invention and may include substituents which themselves may be further substituted) at a carbon (or nitrogen) position anywhere on a molecule within context, and includes as substituents hydroxyl, thiol, carboxyl, cyano (C≡N), nitro (NO$_2$), halogen (in certain embodiments, 1, 2 or 3 halogens, especially on an alkyl, especially a methyl group such as a trifluoromethyl), an alkyl group (in certain embodiments, $C_1$-$C_{10}$, more in certain embodiments, $C_1$-$C_6$), aryl (especially phenyl and substituted phenyl for example benzyl or benzoyl), alkoxy group (in certain embodiments, $C_1$-$C_6$ alkyl or aryl, including phenyl and substituted phenyl), thioether ($C_1$-$C_6$ alkyl or aryl), acyl (in certain embodiments, $C_1$-$C_6$ acyl), ester or thioester (in certain embodiments, $C_1$-$C_6$ alkyl or aryl) including alkylene ester (such that attachment is on the alkylene group, rather than at the ester function which is in certain embodiments substituted with a $C_1$-$C_6$ alkyl or aryl group), in certain embodiments, $C_1$-$C_6$ alkyl or aryl, halogen (in certain embodiments, F or Cl), amine (including a five- or six-membered cyclic alkylene amine, further including a $C_1$-$C_6$ alkyl amine or a $C_1$-$C_6$ dialkyl amine which alkyl groups may be substituted with 1-2 hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, in certain embodiments chlorine substituent), hydrazine, amido, which is in certain embodiments substituted with 1-2 $C_1$-$C_6$ alkyl groups (including a carboxamide which is optionally substituted with 1-2 $C_1$-$C_6$ alkyl groups), alkanol (in certain embodiments, $C_1$-$C_6$ alkyl or aryl), or alkanoic acid (in certain embodiments, $C_1$-$C_6$ alkyl or aryl). Substituents according to the present invention may include, for example —SiR$_1$R$_2$R$_3$ groups where each of R$_1$ and R$_2$ is as otherwise described herein and R$_3$ is H or a $C_1$-$C_6$ alkyl group, in certain embodiments R$_1$, R$_2$, R$_3$ in this context is a $C_1$-$C_3$ alkyl group (including an isopropyl or t-butyl group). Each of the above-described groups may be linked directly to the substituted moiety or alternatively, the substituent may be linked to the substituted moiety (in certain embodiments in the case of an aryl or heteroaryl moiety) through an optionally substituted —(CH$_2$)$_m$— or alternatively an optionally substituted —(OCH$_2$)$_m$—, —(OCH$_2$CH$_2$)$_m$— or —(CH$_2$CH$_2$O)$_m$— group, which may be substituted with any one or more of the above-described substituents. Alkylene groups —(CH$_2$)$_m$— or —(CH$_2$)$_n$— groups or other chains such as ethylene glycol chains, as identified above, may be substituted anywhere on the chain. Exemplary substitutents on alkylene groups include halogen or $C_1$-$C_6$ (in certain embodiments $C_1$-$C_3$) alkyl groups, which may be optionally substituted with 1-2 hydroxyl groups, 1-2 ether groups (O—$C_1$-$C_6$ groups), up to three halo groups (in certain embodiments F), or a sidechain of an amino acid as otherwise described herein and optionally substituted amide (in certain embodiments carboxamide substituted as described above) or urethane groups (often with 1-2 $C_0$-$C_6$ alkyl substitutents, which group(s) may be further substituted). In certain embodiments, the alkylene group (often a single methylene group) is substituted with 1-2 optionally substituted $C_1$-$C_6$ alkyl groups, in certain embodiments $C_1$-$C_4$ alkyl group, most often methyl or O-methyl groups or a sidechain of an amino acid as otherwise described herein. In the present invention, a moiety in a molecule may be optionally substituted with up to five substituents, in certain embodiments up to three substituents. Most often, in the present invention moieties which are substituted are substituted with 1-2 substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—NR$_1$R$_2$ or —N(R$_1$)—C(O)—O—R$_1$, nitro, cyano and amine (especially including a $C_1$-$C_6$ alkylene-NR$_1$R$_2$, a mono- or di-$C_1$-$C_6$ alkyl substituted amines which may be optionally substituted with 1-2 hydroxyl groups). Each of these groups contain unless otherwise indicated, within context, between 1 and 6 carbon atoms. In certain embodiments, specific substituents include for example, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, $C_1$-$C_6$ alkyl, —(CH$_2$)$_n$O—(C$_1$-$C_6$ alkyl), —(CH$_2$)$_n$C(O)—(C$_1$-$C_6$ alkyl), —(CH$_2$)$_n$OC(O)—(C$_1$-$C_6$ alkyl), —(CH$_2$)$_n$C(O)O—(C$_1$-$C_6$ alkyl), —(CH$_2$)$_n$NHC(O)—R$_1$, —(CH$_2$)$_n$C(O)—NR$_1$R$_2$, —(O(CH$_2$)$_n$OH, —(CH$_2$O)$_n$COOH, $C_1$-$C_6$ alkyl, —(OCH$_2$)$_n$O—(C$_1$-$C_6$ alkyl), —(CH$_2$O)$_n$C(O)—(C$_1$-$C_6$ alkyl), —(OCH$_2$)$_n$NHC(O)—R$_1$, —(CH$_2$O)$_n$C(O)—NR$_1$R$_2$, —S(O)$_2$—R$_S$, —S(O)—R$_S$ (R$_S$ is $C_1$-$C_6$ alkyl or a —(CH$_2$)$_m$—NR$_1$R$_2$ group), NO$_2$, CN or halogen (F, Cl, Br, I, in certain embodiments F or Cl), depending on the context of the use of the substituent. $R_1$ and $R_2$ are each, within context, H or a $C_1$-$C_6$ alkyl group (which may be optionally substituted with 1-2 hydroxyl groups or up to three halogen groups, in certain embodiments fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, in certain embodiments with optionally substituted $C_1$-$C_6$ alkyl groups (methyl, ethyl or hydroxymethyl or hydroxyethyl as examples, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, in certain embodiments no more than 3 substituents and in certain embodiments with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, and so forth) and can be bound to the compound according to the present invention at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (monocyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, and so forth, among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising two or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" refers to a cyclic group which contains at least one heteroatom, i.e., O, N or S, and may be aromatic (heteroaryl) or non-aromatic. Thus, the heteroaryl moieties are subsumed under the definition of heterocycle, depending on the context of its use. Exemplary heteroaryl groups are described hereinabove. Exemplary non-aromatic heterocyclic groups for use in the present invention include, for example, pyrrolidinyl, pyrrolinyl, piperidinyl, piperazinyl, N-methylpiperazinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide, among others, as described herein.

The terms "treat", "treating", and "treatment", and so forth, as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present invention are set forth hereinabove.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. In certain exemplary aspects of the present invention, one or more of the present compounds described above, are coadministered in combination with at least one additional bioactive agent, especially including an anticancer agent. In particularly exemplary aspects of the invention, the coadministration of compounds results in synergistic therapeutic, including anticancer therapy.

Description

In one aspect, the present invention provides a composition useful for regulating protein activity. The composition comprises a ubiquitin pathway protein binding moiety (in certain embodiments for a VHL, cereblon, MDM2, or IAP E3 ligase) according to a defined chemical structure and a protein targeting moiety that are linked together, in certain embodiments through a linker, wherein the ubiquitin pathway protein binding moiety recognizes an ubiquitin pathway protein and the targeting moiety recognizes a target protein [e.g., estrogen related receptor alpha (ERRα), or RIPK2] and wherein the ubiquitin pathway protein binding moiety is coupled to the targeting moiety.

In another aspect, the present invention provides a library of compounds. The library comprises more than one compound wherein each composition has a formula of A-B, wherein A is a ubiquitin pathway protein binding moiety (in certain embodiments, VHL, cereblon, MDM2, or IAP E3 ligase) and B is a protein binding member of a molecular library (e.g., ERRα, or RIPK2), wherein A is coupled (in certain embodiments, through a linker moiety) to B, and wherein the ubiquitin pathway protein binding moiety recognizes an ubiquitin pathway protein, in particular, an E3 ubiquitin ligase. In certain embodiments, the library contains a specific ubiquitination recognition peptide of VHL for an E3 ubiquitin ligase (ubiquitin pathway protein binding moiety as otherwise disclosed herein) with random target protein binding elements (e.g., a chemical compound library).

As such, the target protein is not determined in advance and the method can be used to determine the activity of a putative protein binding element and its pharmacological value as a target upon degradation by ubiquitin ligase.

In still another aspect, the present invention provides a method of screening a library of the present invention to identify a compound containing a targeting moiety, which recognizes a target protein [e.g., estrogen related receptor alpha (ERRα), or RIPK2] associated with a predetermined function of a cell. The method comprises incubating a cell with a pool of entities from the library; monitoring the predetermined function of the cell; identifying a pool of entities that change the predetermined function of the cell; incubating the cell with a composition from the identified pool of entities; monitoring the predetermined function of the cell; and identifying a composition that changes the predetermined function of the cell, wherein the identified composition contains a targeting moiety which recognizes a target protein associated with the predetermined function.

In yet other aspect, the present invention provides a method of screening a library of the present invention to identify a composition containing a targeting moiety, which recognizes a target protein [e.g., estrogen related receptor alpha (ERRα), or RIPK2] associated with a predetermined function of a cell. The method comprises incubating a cell with each composition from the library; monitoring the predetermined function of the cell; identifying a composition that changes the predetermined function of the cell; wherein the identified composition contains a targeting moiety, which recognizes a target protein associated with the predetermined function.

In still another aspect, the present invention provides a method of identifying a target protein [e.g., estrogen related receptor alpha (ERRα), or RIPK2] associated with a predetermined function of a cell. The method comprises incubating a cell with a composition from the library of the present invention; monitoring the predetermined function of the cell; identifying a composition that changes the predetermined function of the cell; identifying a target protein that binds to the identified composition, wherein the target protein is associated with the predetermined function of the cell.

In yet another aspect, the present invention provides a method of identifying a target protein [e.g., estrogen related receptor alpha (ERRα), AR, or RIPK2] associated with a predetermined function of a cell. The method comprises incubating a cell with a pool of entities from the library of the present invention; monitoring the predetermined function of the cell; identifying a pool of entities that change the predetermined function of the cell; incubating the cell with a composition from the identified pool of entities; monitoring the predetermined function of the cell; identifying a composition that changes the predetermined function of the cell; and identifying a target protein that binds to the identified composition, wherein the target protein is associated with the predetermined function of the cell.

In yet another aspect, the present invention provides a method of ubiquitinating/degrading a target protein [e.g., estrogen related receptor alpha (ERRα), or RIPK2] in a cell. The method comprises administering a bifunctional composition comprising an ubiquitin pathway protein binding moiety and a targeting moiety, in certain embodiments linked through a linker moiety, as otherwise described herein, wherein the ubiquitin pathway protein binding moiety is coupled to the targeting moiety and wherein the ubiquitin pathway protein binding moiety recognizes a ubiquitin pathway protein (e.g., VHL, cereblon, MDM2, or IAP E3 ligase) and the targeting moiety recognizes the target protein [e.g., estrogen related receptor alpha (ERRα), or RIPK2] such that degradation of the target protein occurs when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cells of a patient.

In still another aspect, the present invention is directed to a method of treating a patient in need for a disease state or condition modulated through a protein [e.g., estrogen related receptor alpha (ERRα), or RIPK2] where the degradation of that protein produces a therapeutic effect in that patient, the method comprising administering to a patient in need an effective amount of a compound according to the present invention, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In certain embodiments, the present invention is directed to a compound according to the structure L-ULM, where L is a linker group, and ULM is a ubiquitin ligase binding moiety, wherein said linker group is optionally further linked to a PTM group.

In other embodiments, the present invention is directed to a compound comprising a PTM group (e.g., derivatized

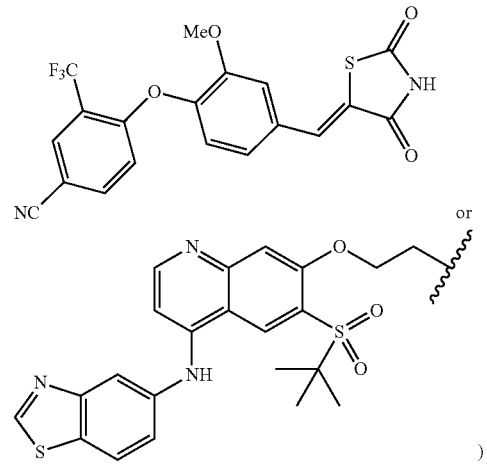

according to the general structure: ULM-L-PTM, wherein: ULM is an ubiquitin ligase binding moiety (in certain embodiments a ligand), which binds an ubiquitin ligase [in certain embodiments an E3 ubiquitin ligase (e.g., VHL)]; PTM is a chemical moiety (protein targeting moiety) (e.g., derivatized

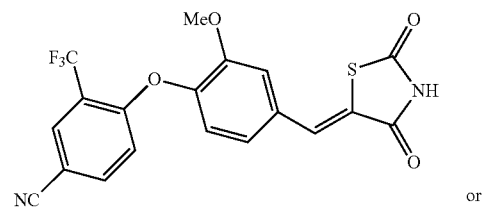

-continued

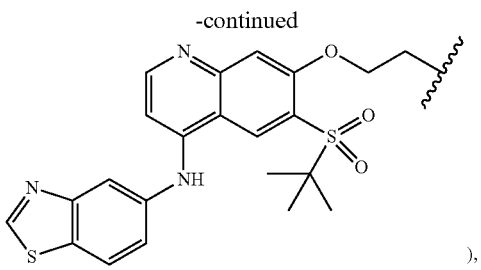

), which binds to a target protein (e.g., estrogen related receptor alpha (ERRα) or RIPK2, respectively) or polypeptide, which is ubiquitinated by an ubiquitin ligase and is chemically linked directly to the ULM group or through a linker moiety L, or PTM is alternatively a ULM' group that is also an ubiquitin ligase binding moiety, which may be the same or different than the ULM group and is linked directly to the ULM group directly or through the linker moiety; and L is a linker moiety that may be present or absent and chemically (covalently) links ULM to PTM, or a pharmaceutically acceptable salt, enantiomer, stereoisomer, solvate or polymorph thereof.

In certain embodiments, the compounds as described herein can be chemically linked or coupled via a chemical linker (L). In certain embodiments, the linker group L is a group comprising one or more covalently connected structural units of A (e.g., -$A_1$ . . . $A_q$-), wherein $A_1$ is a group coupled to at least one of a ULM, a PTM, or a combination thereof. In certain embodiments, $A_1$ links a ULM, a PTM, or a combination thereof directly to another ULM, PTM, or combination thereof. In other embodiments, $A_1$ links a ULM, a PTM, or a combination thereof indirectly to another ULM, PTM, or combination thereof through $A_q$.

In certain embodiments, $A_1$ to $A_q$ are, each independently, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$ $C_{3-11}$cycloalkyl optionally substituted with 0-6 $R^{L1}$ and/or $R^{L2}$ groups, $C_{3-11}$heterocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently, can be linked to other A groups to form cycloalkyl and/or heterocyclyl moiety which can be further substituted with 0-4 $R^{L5}$ groups; wherein $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, SON($C_{1-8}$alkyl$)_2$, $CONHC_{1-8}$alkyl, $CON(C_{1-8}$alkyl$)_2$, $N(C_{1-8}$alkyl)$CONH(C_{1-8}$alkyl), $N(C_{1-8}$alkyl)$CON(C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl) $SO_2N(C_{1-8}$alkyl$)_2$, NH $SO_2NH(C_{1-8}$alkyl), NH $SO_2N(C_{1-8}$alkyl$)_2$, NH $SO_2NH_2$.

In certain embodiments, q is an integer greater than or equal to 0. In certain embodiments, q is an integer greater than or equal to 1.

In certain embodiments, e.g., where q is greater than 2, $A_q$ is a group that is connected to a ULM or ULM' moiety, and $A_1$ and $A_q$ are connected via structural units of A (number of such structural units of A: q-2).

In certain embodiments, e.g., where q is 2, $A_q$ is a group that is connected to $A_1$ and to a ULM or ULM' moiety.

In certain embodiments, e.g., where q is 1, the structure of the linker group L is -$A_1$-, and $A_1$ is a group which is connected to a ULM or ULM' moiety and a PTM moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, the linker (L) is selected from the group consisting of:

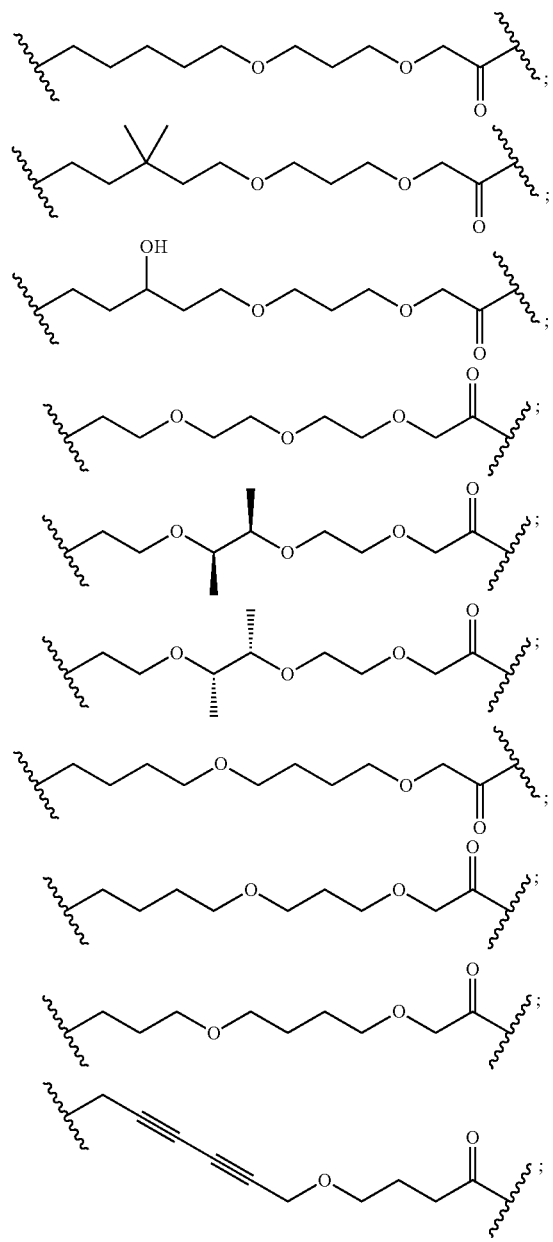

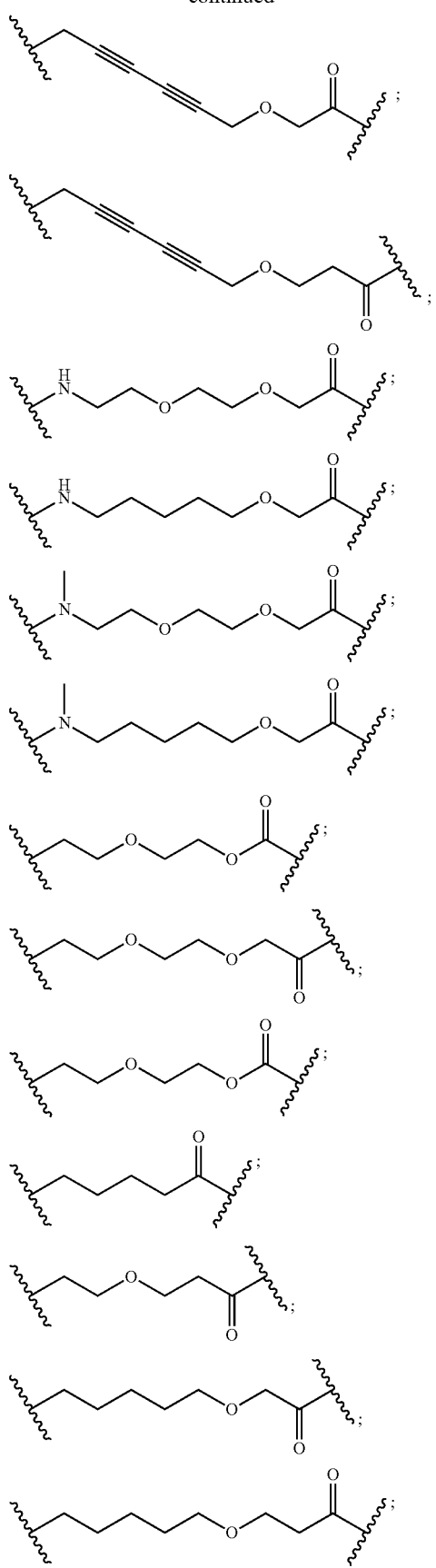
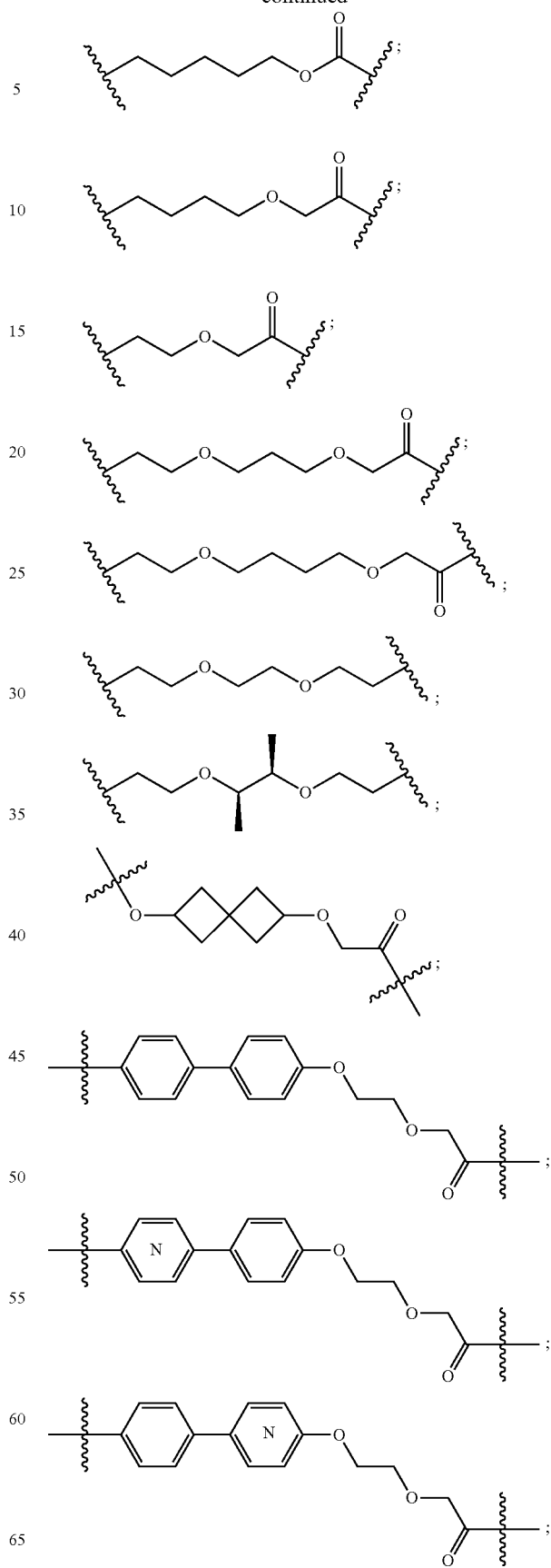

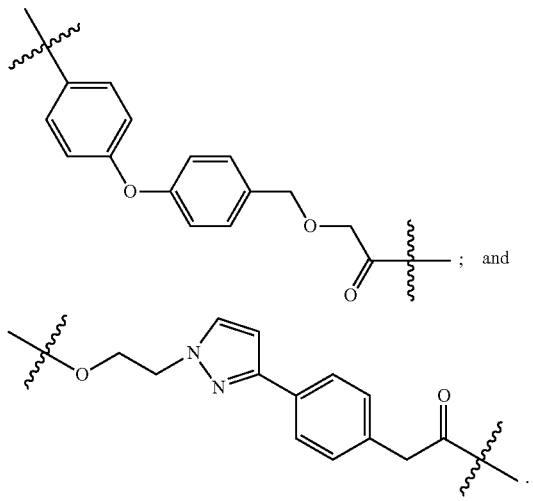

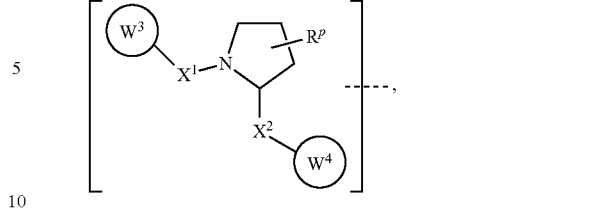

ULM-a

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In certain embodiments, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

The ULM group and PTM group may be covalently linked to the linker group through any group which is appropriate and stable to the chemistry of the linker. In exemplary aspects of the present invention, the linker is independently covalently bonded to the ULM group and the PTM group in certain embodiments through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. In certain aspects where the PTM group is a ULM group, the target protein for degradation may be the ubiquitin ligase itself. In certain exemplary aspects, the linker may be linked to an optionally substituted alkyl, alkylene, alkene or alkyne group, an aryl group or a heterocyclic group on the ULM and/or PTM groups.

In certain embodiments of the compounds as described herein, the ULM comprises a chemical structure selected from the group ULM-a:

wherein a dashed line indicates the attachment of at least one PTM, another ULM or VLM (i.e., ULM' or VLM'), or a chemical linker moiety coupling at least one PTM, a ULM' or VLM' to the other end of the linker;

$X^1$, $X^2$ are each independently a bond, O, $NR^{Y3}$, $CR^{Y3}R^{Y4}$, C=O, C=S, S=O, or $SO_2$;

$R^{Y3}$, $R^{Y4}$ are each independently H, or $C_{1-6}$ alkyl (linear, branched, optionally substituted by 1 or more halo, $C_{1-6}$ alkoxyl), optionally substituted by 1-3 $R^P$ groups in the pyrrolidine moiety, wherein each $R^P$ is independently H, halo, —OH, or $C_{1-3}$alkyl;

$W^3$ is an optionally substituted -T-$N(R^{1a}R^{1b})$, -T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle, where T is covalently bonded to $X^1$;

each $R^1$, $R^{1a}$, $R^{1b}$ is independently H, or a $C_1$-$C_6$ alkyl group (linear, branched, optionally substituted by 1 or more halo, —OH), $R^{Y3}$C=O, $R^{Y3}$C=S, $R^{Y3}$SO, $R^{Y3}SO_2$, $N(R^{Y3}R^{Y4})$C=O, $N(R^{Y3}R^{Y4})$C=S, $N(R^{Y3}R^{Y4})$SO, or $N(R^{Y3}R^{Y4})SO_2$;

T is an optionally substituted —$(CH_2)_n$— group, wherein each one of the methylene groups may be optionally substituted with 1-2 substituents, in certain embodiments selected from halogen, a $C_1$-$C_6$ alkyl group (linear, branched, optionally substituted by 1 or more halogen, —OH) or the sidechain of an amino acid as otherwise described herein, in certain embodiments methyl, which may be optionally substituted; and n is 0 to 6, in certain embodiments 0, 1, 2, or 3, in certain embodiments 0.

Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted; and $W^4$ is an optionally substituted —$NR^1$-T-Aryl, an optionally substituted —$NR^1$-T-Heteroaryl group or an optionally substituted —$NR^1$-T-Heterocycle, where —$NR^1$ is covalently bonded to $X^2$; $R^1$ is H or $CH_3$, in certain embodiments H, and T is an optionally substituted —$(CH_2)_n$— group, wherein each one of the methylene groups may be optionally substituted with 1-2 substituents, in certain embodiments selected from halogen, an amino acid sidechain as otherwise described herein or a $C_1$-$C_6$ alkyl group (linear, branched, optionally substituted by 1 or more halo, —OH), in certain embodiments 1-2 methyl groups, which may be optionally substituted; and n is 0 to 6, often 0, 1, 2 or 3, in certain embodiments 0 or 1.

Alternatively, T may also be a —$(CH_2O)_n$— group, a —$(OCH_2)_n$— group, a —$(CH_2CH_2O)_n$— group, a —$(OCH_2CH_2)_n$— group, all of which groups are optionally substituted.

In any of the embodiments described herein, $W^3$ and/or $W^4$ can be attached to a linker moiety as described herein.

In certain embodiments, aryl groups for $W^3$ include optionally substituted phenyl or naphthyl groups, in certain embodiments phenyl groups, wherein the phenyl or naphthyl group is optionally substituted with a linker group to which is attached a PTM group (including a ULM' group) and/or a halogen (in certain embodiments F or Cl), an amine, mono-alkyl- or dialkyl amine (in certain embodiments, dimethyl-amine), an amido group (in certain embodiments a —(CH$_2$)$_m$—NR$_1$C(O)R$_2$ group where m, R$_1$ and R$_2$ are the same as for R$^1$), a halogen (often F or Cl), OH, CH$_3$, CF$_3$, OMe, OCF$_3$, NO$_2$, CN or a S(O)$_2$R$_S$ group (R$_S$ is a C$_1$-C$_6$ alkyl group, an optionally substituted aryl, heteroaryl or heterocycle group or a —(CH$_2$)$_m$NR$_1$R$_2$ group), each of which may be substituted in ortho-, meta- and/or para-positions of the phenyl ring, in certain embodiments para-), or an aryl (in certain embodiments phenyl), heteroaryl or heterocycle. In certain embodiments said substituent phenyl group is an optionally substituted phenyl group (i.e., the substituent phenyl group itself is in certain embodiments substituted with at least one of F, Cl, OH, SH, COOH, CH$_3$, CF$_3$, OMe, OCF$_3$, NO$_2$, CN or a linker group to which is attached a PTM group (including a ULM' group), wherein the substitution occurs in ortho-, meta- and/or para-positions of the phenyl ring, in certain embodiments para-), a naphthyl group, which may be optionally substituted including as described above, an optionally substituted heteroaryl (in certain embodiments an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(in certain embodiments, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally substituted with a linker group to which is attached a PTM group (including a ULM' group).

In certain embodiments, heteroaryl groups for W$^3$ include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (in certain embodiments methyl substituted), an optionally substituted diazole, an optionally substituted triazole, a tetrazole, an optionally substituted benzofuran, an optionally substituted thiophene, an optionally substituted thiazole (in certain embodiments, methyl and/or thiol substituted), an optionally substituted isothiazole, an optionally substituted triazole (in certain embodiments, a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3, or 4-pyridine) or a group according to the chemical structure:

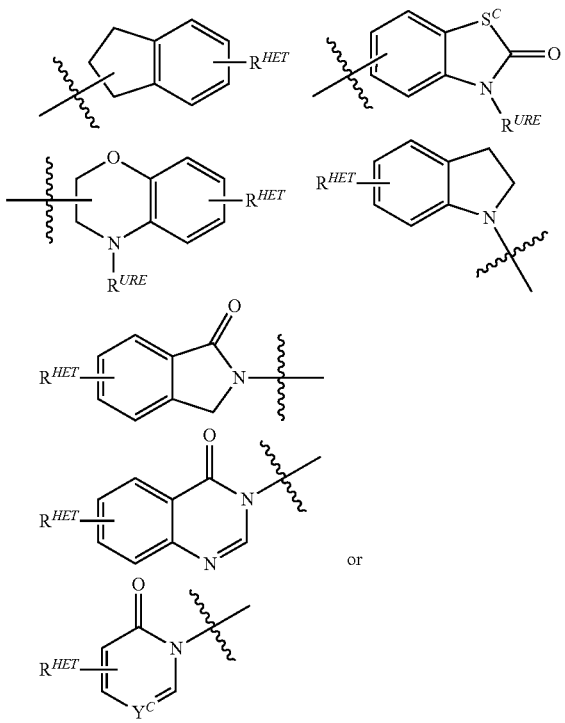

where S$^c$ is CHR$^{SS}$ NR$^{URE}$, or O;

R$^{HET}$ is H, CN, NO$_2$, halo (in certain embodiments Cl or F), optionally substituted C$_1$-C$_6$ alkyl (in certain embodiments substituted with 1-2 hydroxyl groups or up to three halo groups (e.g. CF$_3$), optionally substituted O(C$_1$-C$_6$ alkyl) (in certain embodiments substituted with 1-2 hydroxyl groups or up to three halo groups) or an optionally substituted acetylenic group —C≡C—R$_a$ where R$_a$ is H or a C$_1$-C$_6$ alkyl group (in certain embodiments C$_1$-C$_3$ alkyl);

R$^{SS}$ is H, CN, NO$_2$, halo (in certain embodiments F or Cl), optionally substituted C$_1$-C$_6$ alkyl (in certain embodiments substituted with 1-2 hydroxyl groups or up to three halo groups), optionally substituted O—(C$_1$-C$_6$ alkyl) (in certain embodiments substituted with 1-2 hydroxyl groups or up to three halo groups) or an optionally substituted —C(O)(C$_1$-C$_6$ alkyl) (in certain embodiments substituted with 1-2 hydroxyl groups or up to three halo groups);

R$^{URE}$ is H, a C$_1$-C$_6$ alkyl (in certain embodiments H or C$_1$-C$_3$ alkyl) or a —C(O)(C$_1$-C$_6$ alkyl), each of which groups is optionally substituted with 1-2 hydroxyl groups or up to three halogen, in certain embodiments fluorine groups, or an optionally substituted heterocycle, for example piperidine, morpholine, pyrrolidine, tetrahydrofuran, tetrahydrothiophene, piperidine, piperazine, each of which is optionally substituted; and Y$^C$ is N or C—R$^{YC}$, where R$^{YC}$ is H, OH, CN, NO$_2$, halo (in certain embodiments Cl or F), optionally substituted C$_1$-C$_6$ alkyl (in certain embodiments substituted with 1-2 hydroxyl groups or up to three halo groups (e.g. CF$_3$), optionally substituted O(C$_1$-C$_6$ alkyl) (in certain embodiments substituted with 1-2 hydroxyl groups or up to three halo groups) or an optionally substituted acetylenic group —C≡C—R$_a$ where R$_a$ is H or a C$_1$-C$_6$ alkyl group (in certain embodiments C$_1$-C$_3$ alkyl). Each of said heteroaryl groups may be optionally substituted with a linker group to which is attached a PTM group (including a ULM' group).

In additional embodiments, heterocycle groups for $W^3$ include morpholine, tetrahydroquinoline, piperidine, piperazine, pyrrollidine, tetrahydrofuran, tetrahydrothiophene, oxane and thiane, each of which groups may be optionally substituted or a group according to the chemical structure:

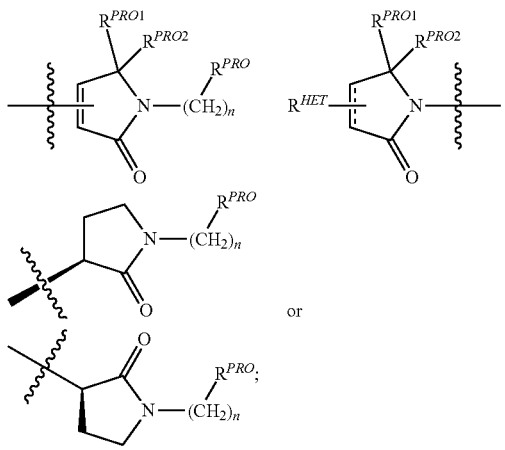

where $R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinolone, benzofuran, indole, indolizine, azaindolizine (each in certain embodiments substituted with a $C_1$-$C_3$ alkyl group, in certain embodiments methyl or a halo group, in certain embodiments F or Cl);

$R^{PRO1}$ and $R^{PRO2}$ are each independently H, an optionally substituted $C_1$-$C_3$ alkyl group or together form a keto group, and each n is 0, 1, 2, 3, 4, 5, or 6 (in certain embodiments 0 or 1), wherein each of said Heterocycle groups may be optionally substituted with a linker group to which is attached a PTM group (including a ULM' group) or a pharmaceutically acceptable salt, stereoisomer, solvate or polymorph thereof.

In certain embodiments, $W^3$ substituents for use in the present invention also include specifically (and without limitation to the specific compound disclosed) the $W^3$ substituents that are found in the identified compounds disclosed herein (which includes the specific compounds which are disclosed in the present specification, and the figures which are attached hereto). Each of these $W^3$ substituents may be used in conjunction with any number of $W^4$ substituents, which are also disclosed herein.

In certain embodiments, aryl groups for $W^4$ include optionally substituted phenyl or naphthyl groups, in certain embodiments phenyl groups, wherein the phenyl group is optionally substituted with a linker group to which is attached an PTMPTM group (including a ULM' group), a halogen (in certain embodiments F or Cl), an amine, mono-alkyl- or dialkyl amine (in certain embodiments, dimethylamine), F, Cl, OH, COOH, $C_1$-$C_6$ alkyl, in certain embodiments $CH_3$, $CF_3$, OMe, $OCF_3$, $NO_2$, or CN group (each of which may be substituted in ortho-, meta- and/or para-positions of the phenyl ring, in certain embodiments para-), an optionally substituted phenyl group (the phenyl group itself is in certain embodiments substituted with a linker group attached to a PTM group, including a ULM' group), and/or at least one of F, Cl, OH, COOH, $CH_3$, $CF_3$, OMe, $OCF_3$, $NO_2$, or CN group (in ortho-, meta- and/or para-positions of the phenyl ring, in certain embodiments para-), a naphthyl group, which may be optionally substituted, an optionally substituted heteroaryl, in certain embodiments an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (in certain embodiments, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

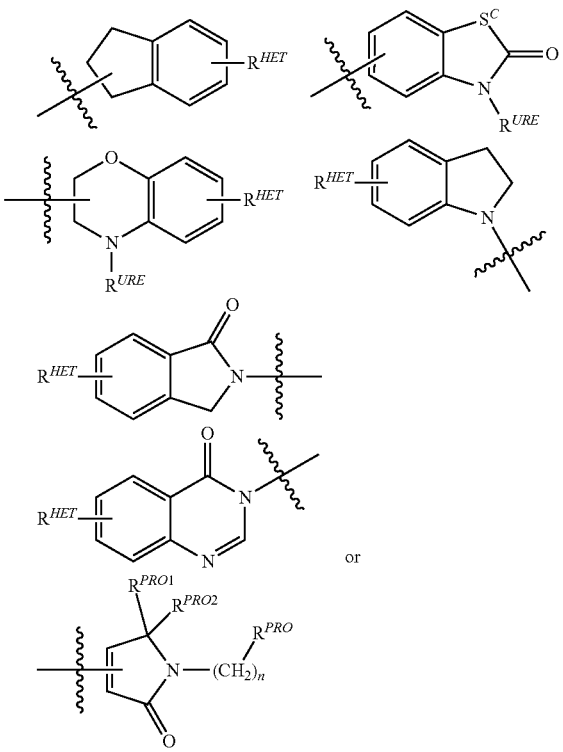

wherein $S^c$ is $CHR^{SS}$, $NR^{URE}$, or O;

$R^{HET}$ is H, CN, $NO_2$, halo (in certain embodiments Cl or F), optionally substituted $C_1$-$C_6$ alkyl (in certain embodiments substituted with 1-2 hydroxyl groups or up to three halo groups (e.g. $CF_3$), optionally substituted $O(C_1$-$C_6$ alkyl) (in certain embodiments substituted with 1-2 hydroxyl groups or up to three halo groups) or an optionally substituted acetylenic group —C≡C—$R_a$ where $R_a$ is H or a $C_1$-$C_6$ alkyl group (in certain embodiments $C_1$-$C_3$ alkyl);

$R^{SS}$ is H, CN, $NO_2$, halo (in certain embodiments F or Cl), optionally substituted $C_1$-$C_6$ alkyl (in certain embodiments substituted with 1-2 hydroxyl groups or up to three halo groups), optionally substituted O—($C_1$-$C_6$ alkyl) (in certain embodiments substituted with 1-2 hydroxyl groups or up to three halo groups) or an optionally substituted —C(O)($C_1$-$C_6$ alkyl) (in certain embodiments substituted with 1-2 hydroxyl groups or up to three halo groups);

$R^{URE}$ is H, a $C_1$-$C_6$ alkyl (in certain embodiments H or $C_1$-$C_3$ alkyl) or a —C(O)($C_1$-$C_6$ alkyl) each of which groups is optionally substituted with 1-2 hydroxyl groups or up to three halogen, in certain embodiments fluorine groups, or an optionally substituted phenyl group, an optionally substituted heteroaryl, or an optionally substituted heterocycle, in certain embodiments for example piperidine, morpholine, pyrrolidine, tetrahydrofuran);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine (each in certain embodiments substituted with a $C_1$-$C_3$ alkyl group, in certain embodiments methyl or a halo group, in certain embodiments F or Cl);

$R^{PRO1}$ and $R^{PRO2}$ are each independently H, an optionally substituted $C_1$-$C_3$ alkyl group or together form a keto group; and each n is independently 0, 1, 2, 3, 4, 5, or 6 (in certain embodiments 0 or 1), or an optionally substituted heterocycle, in certain embodiments tetrahydrofuran, tetrahydrothiene, piperidine, piperazine or morpholine (each of which groups when substituted, are in certain embodiments substituted with a methyl or halo (F, Br, Cl), each of which groups may be optionally substituted with a linker group to which is attached a PTM In certain exemplary aspects,

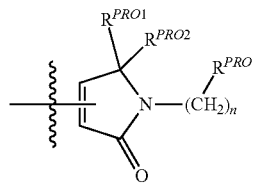

is a

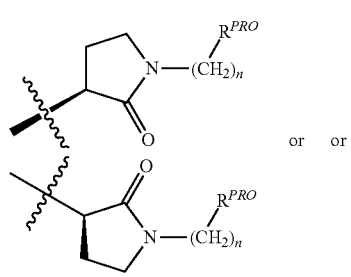

group, where $R^{PRO}$ and n are the same as above.

In certain embodiments, heteroaryl groups for $W^4$ include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3-, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

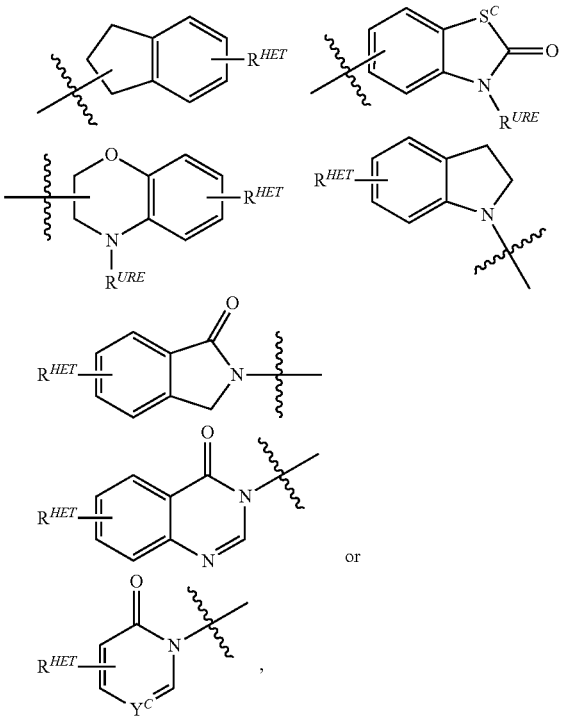

or where $S^c$ is $CHR^{SS}$, $NR^{URE}$, or O;

$R^{HET}$ is H, CN, $NO_2$, halo (in certain embodiments Cl or F), optionally substituted $C_1$-$C_6$ alkyl (in certain embodiments substituted with 1-2 hydroxyl groups or up to three halo groups (e.g. $CF_3$), optionally substituted O($C_1$-$C_6$ alkyl) (in certain embodiments substituted with 1-2 hydroxyl groups or up to three halo groups) or an optionally substituted acetylenic group —C≡C—$R_a$ where $R_a$ is H or a $C_1$-$C_6$ alkyl group (in certain embodiments $C_1$-$C_3$ alkyl);

$R^{SS}$ is H, CN, $NO_2$, halo (in certain embodiments F or Cl), optionally substituted $C_1$-$C_6$ alkyl (in certain embodiments substituted with 1-2 hydroxyl groups or up to three halo groups), optionally substituted O—($C_1$-$C_6$ alkyl) (in certain embodiments substituted with 1-2 hydroxyl groups or up to three halo groups) or an optionally substituted —C(O)($C_1$-$C_6$ alkyl) (in certain embodiments substituted with 1-2 hydroxyl groups or up to three halo groups);

$R^{URE}$ is H, a $C_1$-$C_6$ alkyl (in certain embodiments H or $C_1$-$C_3$ alkyl) or a —C(O)($C_1$-$C_6$ alkyl), each of which groups is optionally substituted with 1-2 hydroxyl groups or up to three halogen, in certain embodiments fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, NO$_2$, halo (in certain embodiments Cl or F), optionally substituted C$_1$-C$_6$ alkyl (in certain embodiments substituted with 1-2 hydroxyl groups or up to three halo groups (e.g. CF$_3$), optionally substituted O(C$_1$-C$_6$ alkyl) (in certain embodiments substituted with 1-2 hydroxyl groups or up to three halo groups) or an optionally substituted acetylenic group —C≡C—R$_a$ where R$_a$ is H or a C$_1$-C$_6$ alkyl group (in certain embodiments C$_1$-C$_3$ alkyl), each of which groups may be optionally substituted with a linker group to which is attached a PTM group (including a ULM' group).

In certain embodiments, heterocycle groups for W$^4$ include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

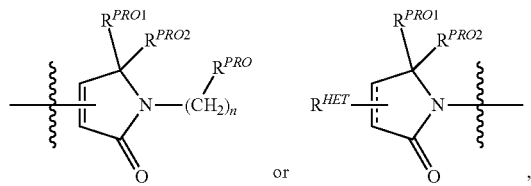

in certain embodiments,

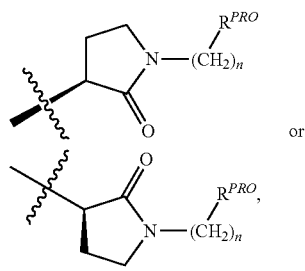

wherein $R^{PRO}$ is H, optionally substituted C$_1$-C$_6$ alkyl or an optionally substituted aryl, heteroaryl or heterocyclic group; $R^{PRO1}$ and $R^{PRO2}$ are each independently H, an optionally substituted C$_1$-C$_3$ alkyl group or together form a keto group; and each n is independently 0, 1, 2, 3, 4, 5, or 6 (often 0 or 1), each of which groups may be optionally substituted with a linker group to which is attached a PTM group (including a ULM' group). In additional embodiments, W$^4$ substituents for use in the present invention also include specifically (and without limitation to the specific compound disclosed) the W$^4$ substituents that are found in the identified compounds disclosed herein (which includes the specific compounds which are disclosed in the present specification, and the figures which are attached hereto). Each of these W$^4$ substituents may be used in conjunction with any number of W$^3$ substituents which are also disclosed herein.

In certain additional embodiments, ULM-a, is optionally substituted by 1-3 R$^P$ groups in the pyrrolidine moiety, wherein each R$^P$ is independently H, halo, —OH, C$_{1-3}$ alkyl.

In any of the embodiments described herein, the W$^3$, W$^4$ can independently be covalently coupled to a linker that is attached one or more PTM groups.

In certain embodiments, ULM is a group (derivatized or configured to be linked or coupled to an PTM via a linker (as indicated by the dashed line) according to the chemical structure:

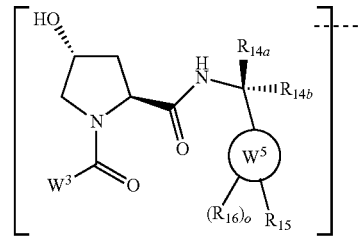

wherein W$^3$ is optionally substituted aryl, optionally substituted heteroaryl, or

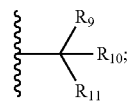

each R$_9$ and R$_{10}$ is independently hydrogen, optionally substituted alkyl, optionally substituted cycloalkyl, optionally substituted hydroxyalkyl, optionally substituted heteroaryl, or haloalkyl; or R$_9$, R$_{10}$, and the carbon atom to which they are attached form an optionally substituted cycloalkyl;

R$_{11}$ is optionally substituted heterocyclic, optionally substituted alkoxy, optionally substituted heteroaryl, optionally substituted aryl,

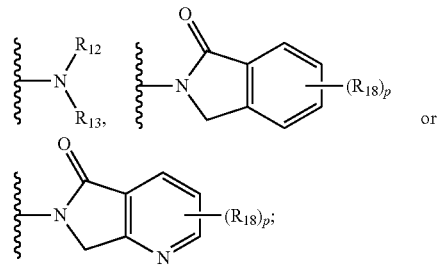

R$_{12}$ is H or optionally substituted alkyl;
R$_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;
R$_{14a}$ and R$_{14b}$ are each independently H, haloalkyl, or optionally substituted alkyl;
W$^5$ is a phenyl or a 5-10 membered heteroaryl;
R$_{15}$ is H, halogen, CN, OH, NO$_2$, NR$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14a}$SO$_2$R$_{14b}$, optionally substituted alkyl, optionally substituted haloalkyl, optionally substituted haloalkoxy; aryl, heteroaryl, cycloalkyl, or cycloheteroalkyl;
each R$_{16}$ is independently halo, optionally substituted alkyl, optionally substituted haloalkyl, hydroxy, or optionally substituted haloalkoxy;
p is 0, 1, 2, 3, or 4; and each $R_{1s}$ is independently halo, optionally substituted alkoxy, cyano, optionally substituted alkyl, haloalkyl, haloalkoxy or a linker.

In certain embodiments, $R_{15}$ is

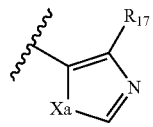

wherein $R_{17}$ is H, halo, optionally substituted $C_{3-6}$ cycloalkyl, optionally substituted $C_{1-6}$ alkyl, optionally substituted $C_{1-6}$ alkenyl, and $C_{1-6}$ haloalkyl; and Xa is S or O.

In certain embodiments, $R_{17}$ is selected from the group consisting of methyl, ethyl, isopropyl, and cyclopropyl.

In certain additional embodiments, $R_{15}$ is selected from the group consisting of:

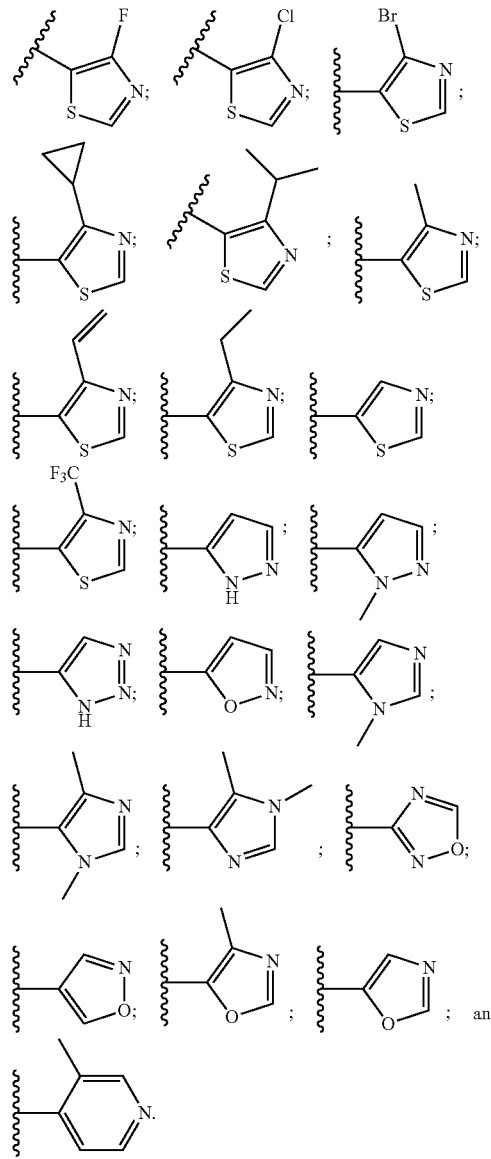

In certain embodiments, $R_{11}$ is selected from the group consisting of:

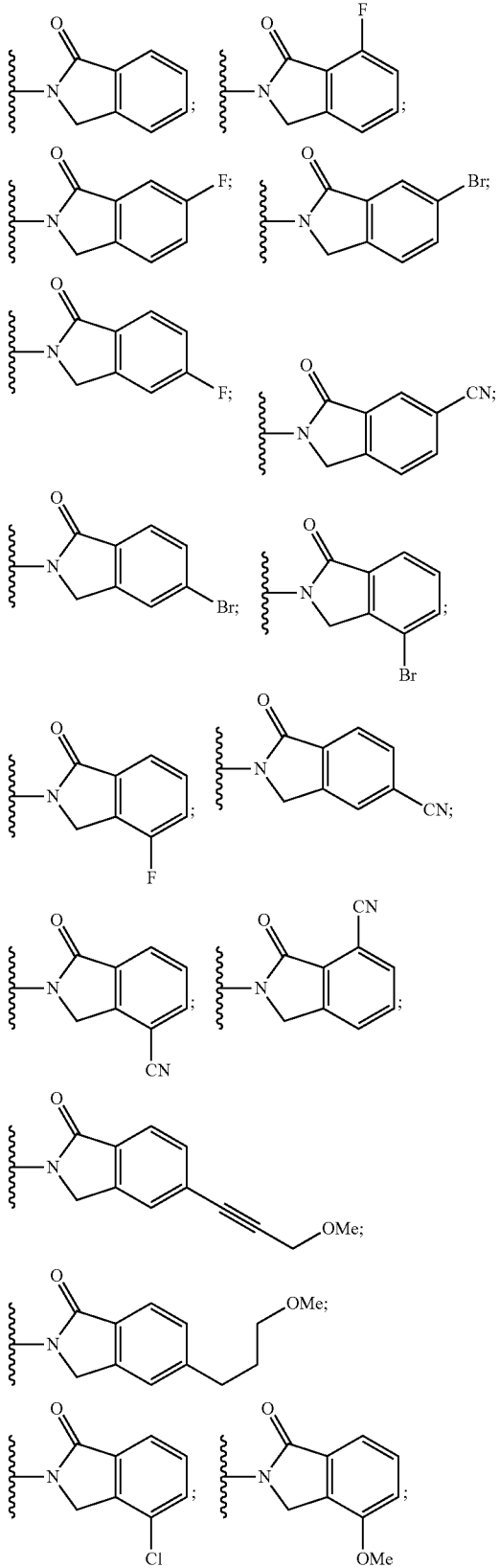

-continued

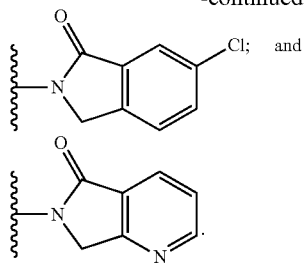

In certain embodiments, the ULM (derivatized or configured to be linked or coupled to an PTM via a linker (as indicated by the dashed line)) has the structure:

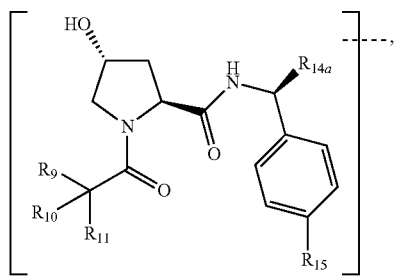

wherein:

$R_{14a}$ is methyl, ethyl, isopropyl, or cyclopropyl;

$R_9$ is H;

$R^{10}$ is isopropyl, tert-butyl, sec-butyl, cyclopentyl, or cyclohexyl;

$R^{11}$ is

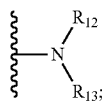

$R_{12}$ is H; and $R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl.

In certain embodiments, the ULM or VLM is selected from the group consisting of:

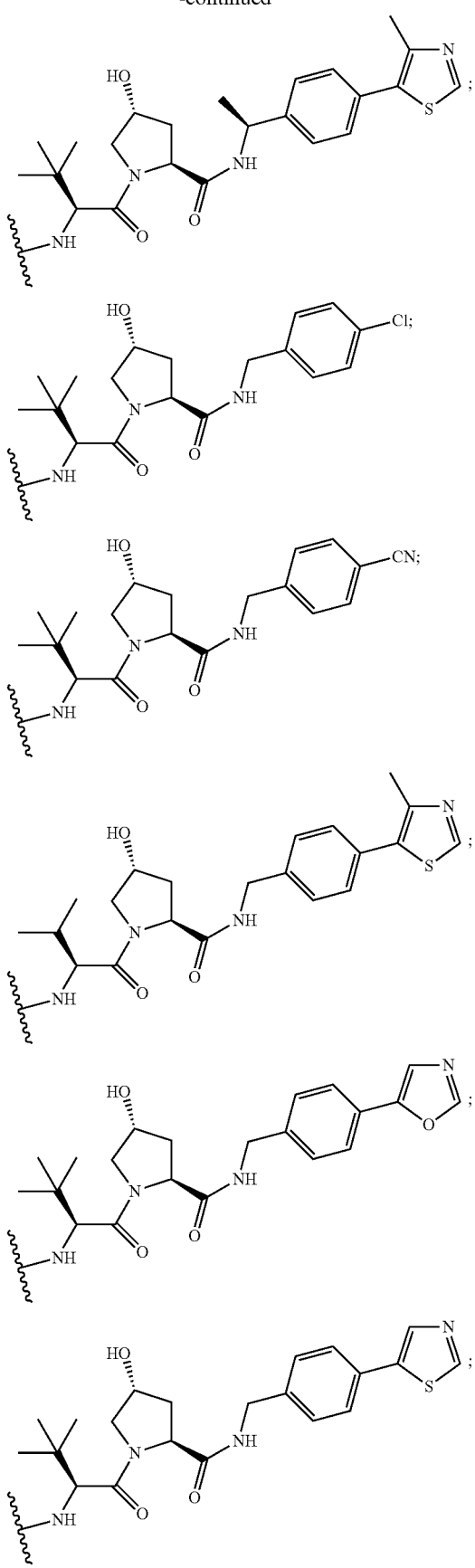

-continued

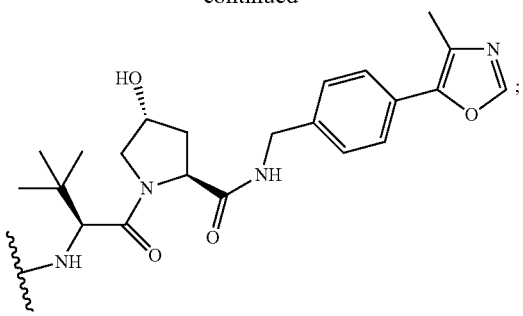

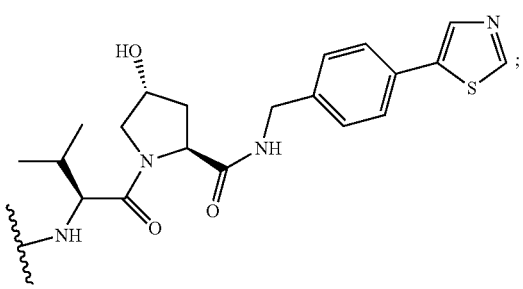

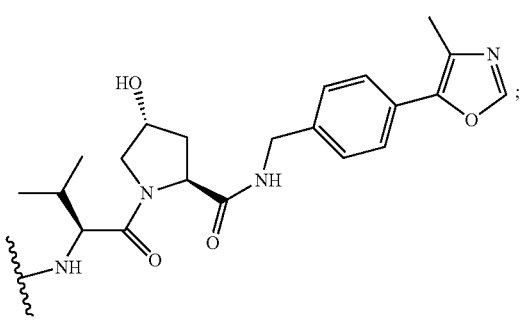

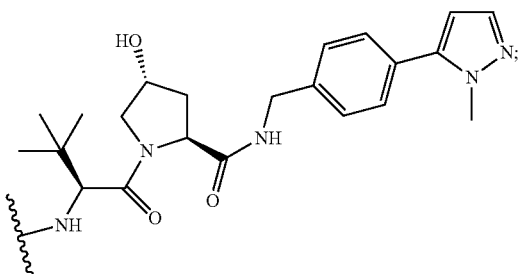

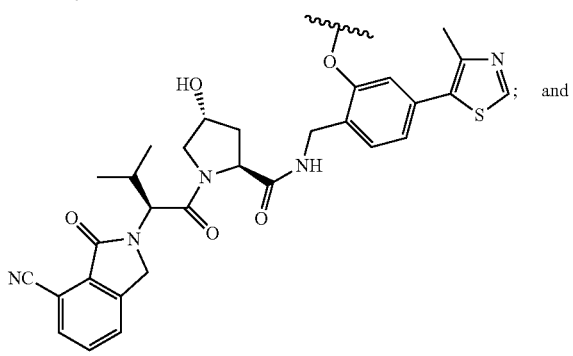

-continued

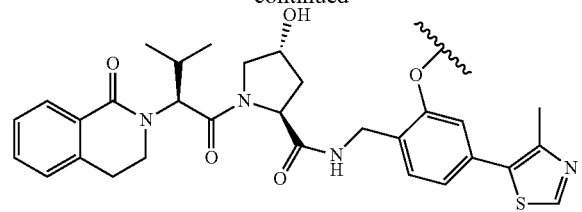

attached to the linker moiety at the position indicated.

In certain embodiments, the PTM comprises a structure selected from, but not limited to the structures shown below, where a dashed line indicates the attachment point of linker moiety:

(PTM-a)

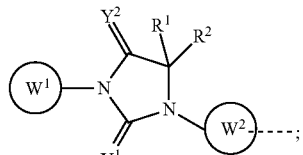

ABM-a (PTM-b)

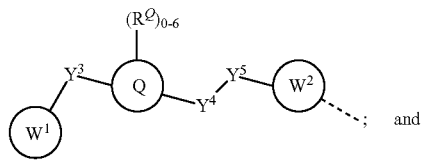

ABM-b (PTM-c)

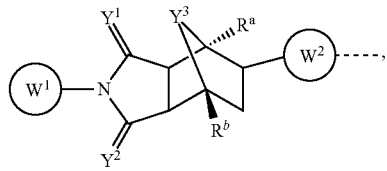

ABM-c wherein $W^1$ is aryl or heteroaryl, independently substituted by 1 or more halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl;

$Y^1$, $Y^2$ are each independently $NR^{Y1}$, O, S;

$Y^3$, $Y^4$, $Y^5$ are each independently a bond, O, $NR^{Y2}$, $CR^{Y1}R^{Y2}$, C=O, C=S, S=O, or $SO_2$;

Q is a 3-6 membered ring with 0-4 heteroatoms, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups, which are taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted by 1 or more halo, $C_{1-6}$ alkoxyl), or $R^1$ and $R^2$, taken together with the atom they are attached to, form a 3-8 membered ring system containing 0-2 heteroatoms;

$W^2$ is a bond, $C_{1-6}$ alkyl, or aryl, or heteroaryl, each optionally substituted by 1, 2 or 3 $R^{W2}$; and each $R^{W2}$ is independently H, halo, C₁₋₆ alkyl (optionally substituted by 1 or more F), or OC₁₋₃alkyl (optionally substituted by 1 or more —F).

In any of the embodiments described herein, the W² is covalently coupled to one or more ULM or VLM groups, or a linker to which is attached one or more ULM or VLM groups as described herein.

In certain embodiments, W¹ is

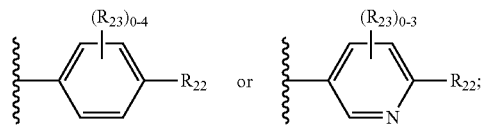

wherein each R₂₂ is independently halo, optionally substituted alkyl, haloalkyl, cyano, or nitro; and each R₂₃ is independently H, halo, optionally substituted alkyl, haloalkyl, cyano, or nitro.

In certain additional embodiments, W¹ is selected from the group consisting of:

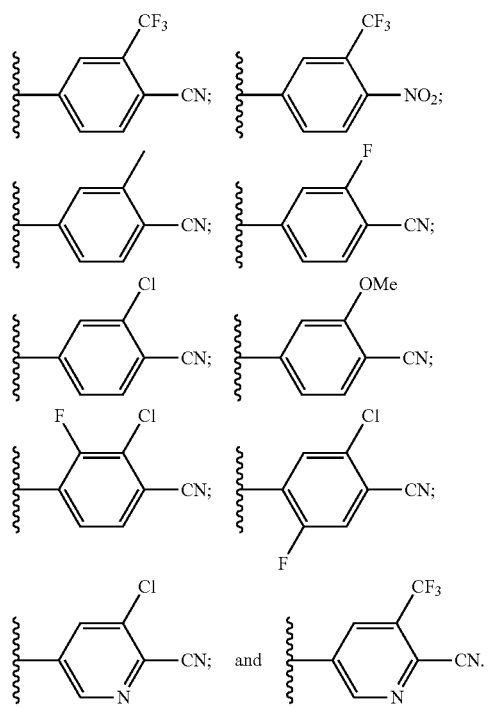

In certain embodiments, PTM is selected from the group consisting of:

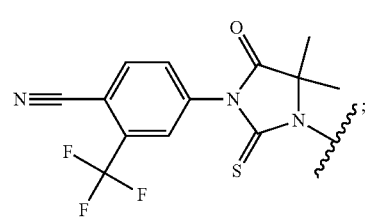

-continued

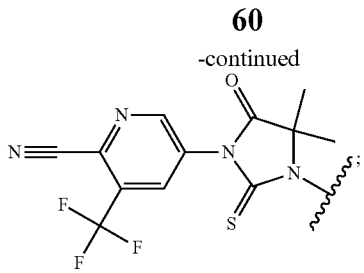

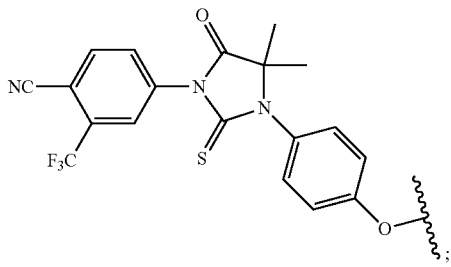

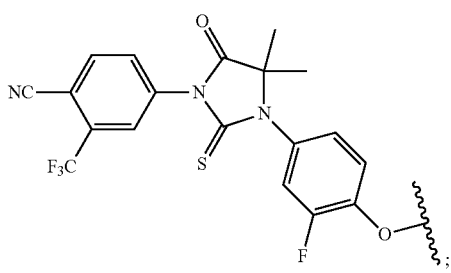

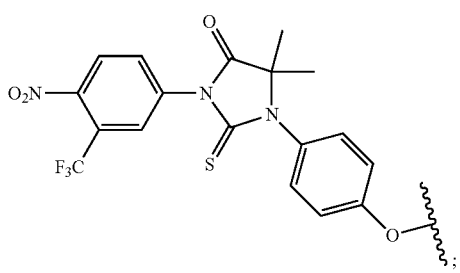

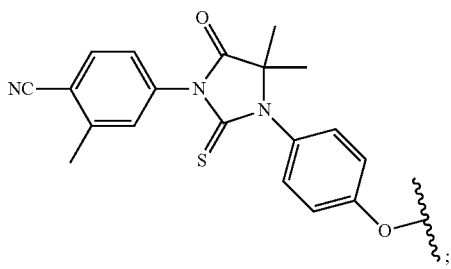

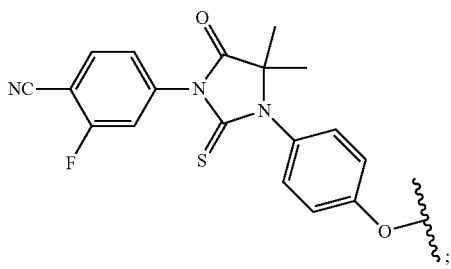

-continued
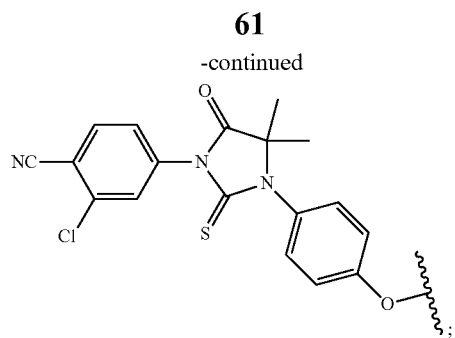
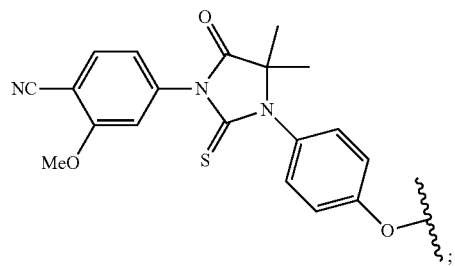
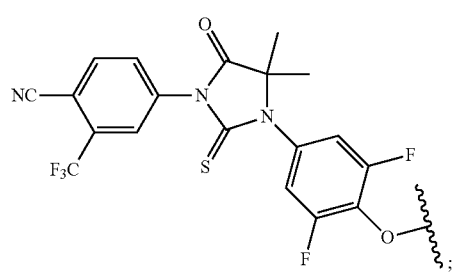
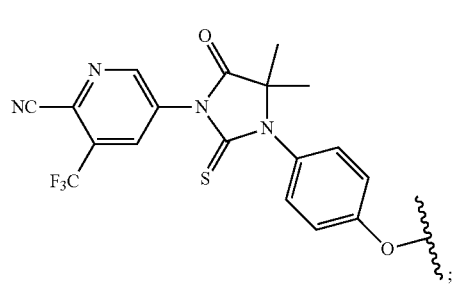
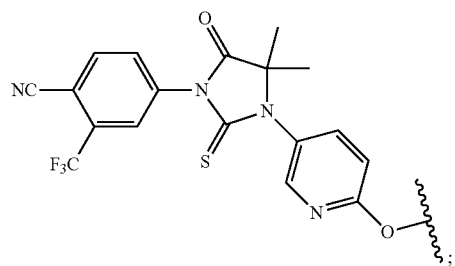
-continued
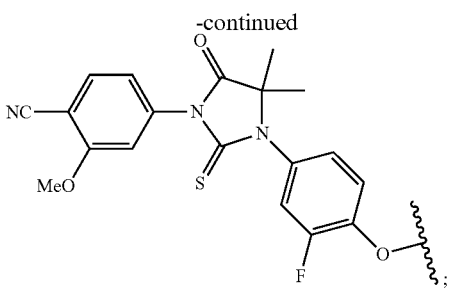
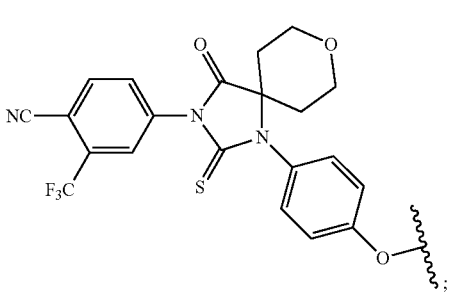
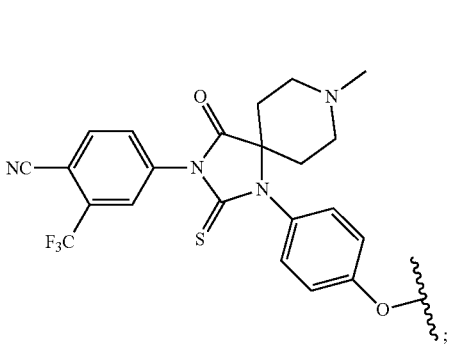
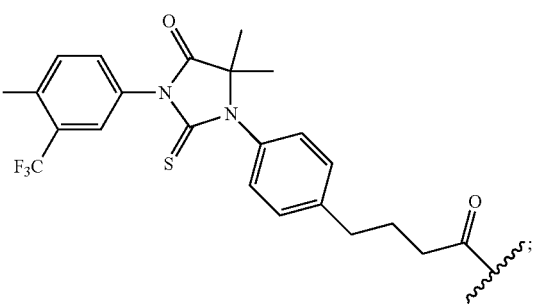
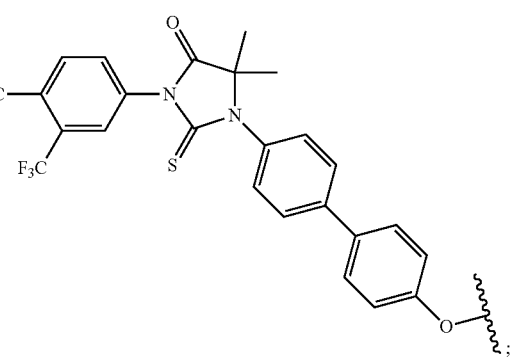

-continued
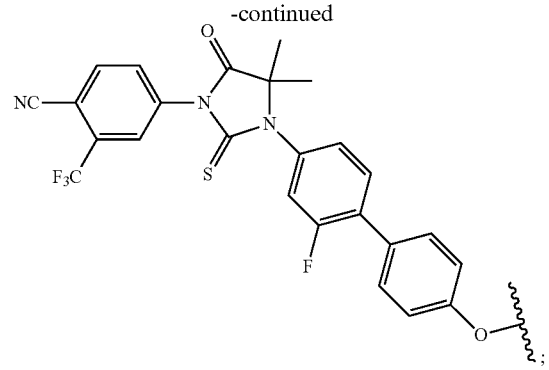
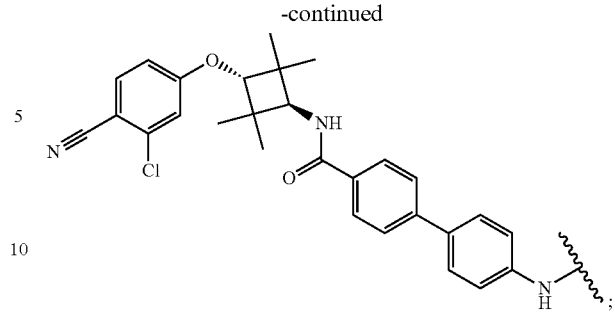
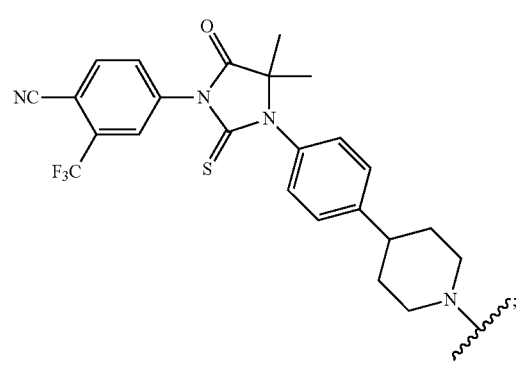
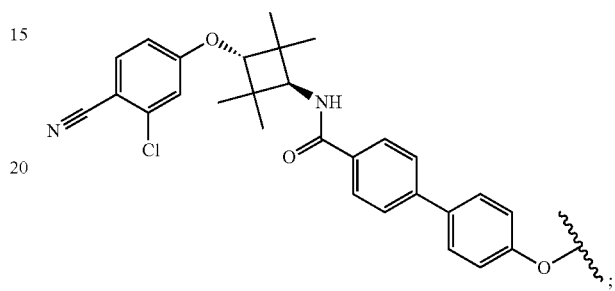
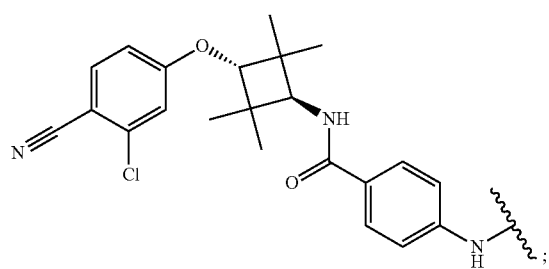
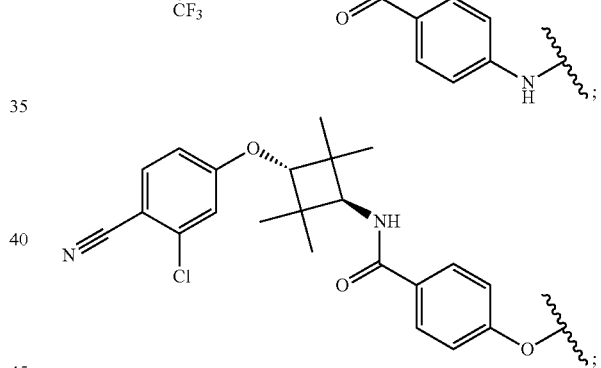
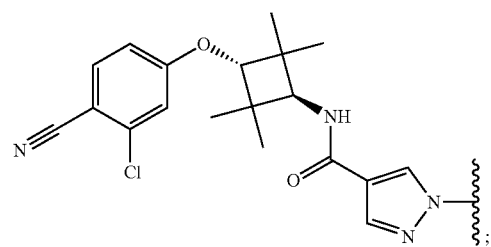
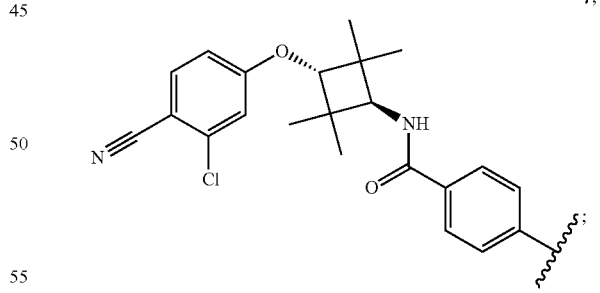
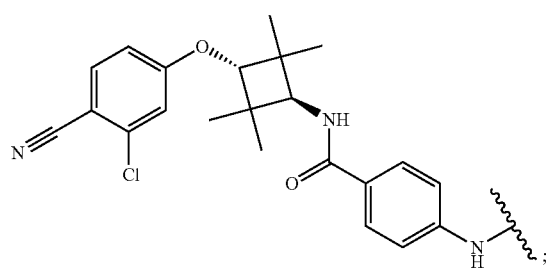
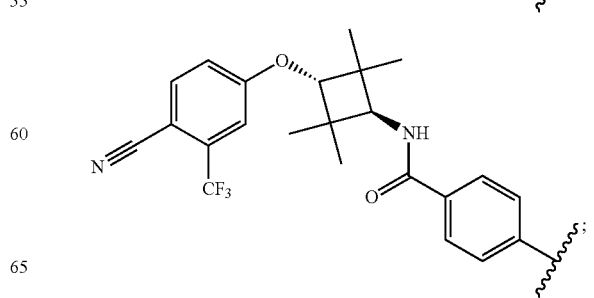

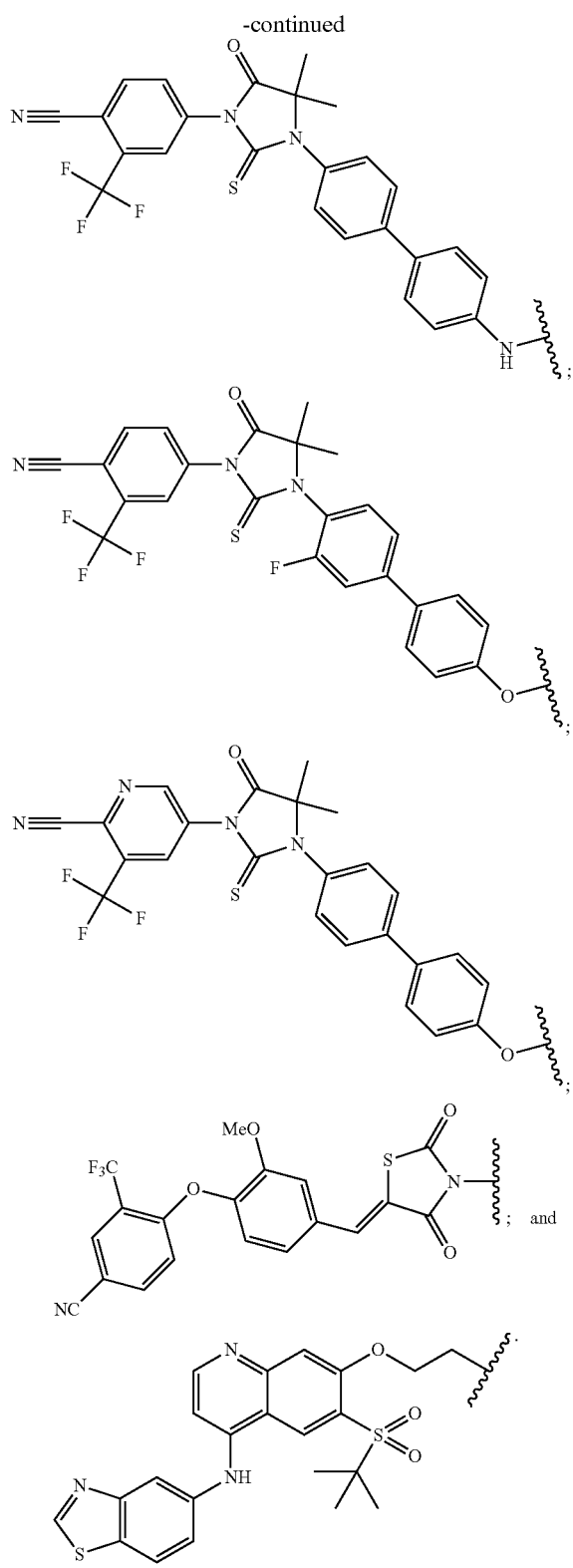

The present invention may be used to treat a number of disease states and/or conditions, including any disease state and/or condition in which proteins are dysregulated and where a patient would benefit from the degradation of proteins [e.g., estrogen related receptor alpha (ERRα), or RIPK2].

In another aspect, the present invention relates to pharmaceutical compositions comprising an effective amount of a compound as set forth hereinabove, in combination with a pharmaceutically acceptable carrier, additive or excipient, and optionally an additional bioactive agent.

In yet another aspect, the present invention relates to a method for treating a disease state by degrading a protein [e.g., estrogen related receptor alpha (ERRα), or RIPK2] or polypeptide through which a disease state or condition is modulated, comprising administering to the patient or subject an effective amount of at least one compound as described hereinabove, optionally in combination with an additional bioactive agent. The method according to the present invention may be used to treat a large number of disease states or conditions including cancer, by virtue of the administration of effective amounts of at least one compound described herein.

Pharmaceutical compositions comprising combinations of an effective amount of at least one bifunctional compound according to the present invention, and one or more of the compounds otherwise described herein, all in effective amounts, in combination with a pharmaceutically effective amount of a carrier, additive or excipient, represents a further aspect of the present invention.

The present invention includes, where applicable, the compositions comprising the pharmaceutically acceptable salts, in particular, acid or base addition salts of compounds of the present invention. The acids used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present invention. The chemical bases used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium, sodium) and alkaline earth metal cations (e.g., calcium, zinc, magnesium), ammonium or water-soluble amine addition salts such as N-methylglucamine (meglumine), and lower alkanol-ammonium and other base salts of pharmaceutically acceptable organic amines, among others.

The compounds of the present invention may, in accordance with the invention, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, subcutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form depends upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention thus is also directed to pharmaceutical compositions comprising an effective amount of compound according to the present invention, optionally in combination with a pharmaceutically acceptable carrier, additive or excipient. Compounds according to the present invention may be administered in immediate release, intermediate release or sustained or controlled release forms. Sustained or controlled release forms are in certain embodiments administered orally, but also in suppository and transdermal or other topical forms. Intramuscular injections in liposomal form may also be used to control or sustain the release of compound at an injection site.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques. In certain embodiments, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically acceptable transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain exemplary aspects of the invention, the compounds may be coated onto a stent to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, in certain embodiments, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. In certain embodiments, the compositions should be formulated to contain between about 0.05 milligram to about 750 milligrams or more, more in certain embodiments about 1 milligram to about 600 milligrams, and even more in certain embodiments about 10 milligrams to about 500 milligrams of active ingredient, alone or in combination with at least one other compound according to the present invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the present invention can be treated by administering to the patient (subject) an effective amount of the compound according to the present invention including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. An exemplary dose of the active compound for all of the herein-mentioned conditions is in the range from about 10 ng/kg to 300 mg/kg, in certain embodiments 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, in certain embodiments 5 to 500 mg of active ingredient per unit dosage form. An oral dosage of about 25-250 mg is often convenient.

The active ingredient is in certain embodiments administered to achieve peak plasma concentrations of the active compound of about 0.00001-30 mM, in certain embodiments about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain exemplary aspects of the invention, one or more compounds according to the present invention are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, exemplary carriers are physiological saline or phosphate buffered saline (PBS).

In certain embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

Examples

The invention is now described with reference to the following Examples. These Examples are provided for the purpose of illustration only, and the invention is not limited to these Examples, but rather encompasses all variations that are evident as a result of the teachings provided herein.

Abbreviations

DCM: dichloromethane. DIPEA: N,N-diisopropylethylamine. DMF: N,N-dimethylformamide. HATU: 2-(7-aza-1H-benzotriazole-1-yl)-1,1,3,3-tetramethyluronium hexafluorophosphate. HPLC: high-performance liquid chromatography. LCMS: liquid chromatography-mass spectrometry. Min: minutes. RT: retention time. tBu: tert-butoxide. TFA: trifluoroacetic acid. THF: tetrahydrofuran.
Methods
Competition Binding Assay with VHL Ligand.

In order to generate a probe matrix of the active and inactive VHL ligand, an amine-functionalized derivative of the VHL ligand was immobilized on NHS-activated Sepharose 4 Fast Flow beads (Amersham Biosciences) at a ligand density of 0.5 mM. Derivatized beads were incubated overnight at room temperature in darkness on an end-over-end shaker and unreacted NHS groups were blocked by incubation with aminoethanol at room temperature on the end-over-end shaker, overnight. Beads were washed with 10 ml of DMSO and were stored in isopropanol at −20 OC. Prior to use, beads were washed three times with 5-10 volumes of DP buffer (50 mM Tris-HCl, 0.8% (v/v) Igepal-CA630, 5% (v/v) glycerol, 150 mM NaCl, 1.5 mM MgCl2, 25 mM NaF, 1 mM sodium vanadate, 1 mM dithiothreitol, Complete EDTA-free protease inhibitor tablet (Roche), pH 7.5), collected by centrifugation for 1 min at 311 g in a Heraeus centrifuge and finally re-suspended in DP buffer to prepare a 5% beads slurry.

Affinity profiling assays were carried out as follows. MCF-7 lysate was diluted with DP buffer to a protein concentration of 5 mg ml$^{-1}$ and cleared by centrifugation at 145,000 g. Aliquots of cell extracts (1 ml) were incubated with test compounds (5 µM active VHL ligand, inactive VHL ligand or vehicle) for 45 min, then 35 ml derivatized Sepharose beads were added per sample and incubated on an end-over-end shaker for 1 h at 4° C. Beads were transferred to disposable columns (MoBiTec), washed with DP buffer containing 0.2% Igepal CA-630 and eluted with 50 ml 2×SDS sample buffer. Proteins were alkylated with 200 mg/ml iodoacetamide for 30 min, partially separated on 4-12% NuPAGE (Invitrogen), and stained with colloidal Coomassie before trypsin digestion and mass spectrometric analysis.

Cell Culture.

Human MDA-MB-231 and MCF7 cells (purchased authenticated ATCC cell lines) were cultured in complete growth medium (Dulbecco's modified Eagle's medium (DMEM)/F12 supplemented with 10% FBS; Life Technologies) and grown at 37° C. with 5% $CO_2$. THP-1 cells (ATCC) were cultured in RPMI 1640+10% FBS and were grown at 37° C. with 5% $CO_2$. For cellular degradation of ERRα, MCF7 cells were seeded in a 24-well plate at 70% confluency, allowed to attach overnight, and incubated with the indicated compounds. For cellular degradation of RIPK2, 5×10⁶ cells were incubated with the indicated compounds. When indicated, a 1-hour pretreatment with 1 μM epoxomicin was performed before the addition of compound. When indicated for washout studies, after PROTAC treatment, cells were washed repeatedly with PBS and incubated with complete medium for the indicated time before harvesting. The THP1 cell line has been authenticated using the Promega GenePrint10 kit to generate a STR Profile for comparison to the expected profile reported by ATCC. Cells were also routinely tested and negative for mycoplasma. Cell lines were routinely tested for mycoplasma contamination at Clongen (Gaithersburg, Md.).

Antibodies.

Anti-estrogen-related receptor alpha antibodies were purchased from Millipore (EPR46Y, 1:1,000 dilution) or Cell Signaling Technology (E1G1J, 1:1,000 dilution). Anti-RIPK2 (D10B11, 1:500 dilution), anti-GAPDH antibodies (D16H11, 1:2,500 dilution), anti-mouse IgG-HRP, and anti-rabbit IgG-HRP were purchased from Cell Signaling Technology and used at 1:10,000 dilution. Anti-actin antibody was purchased from Abcam (ab6276, 1:2,000). Anti-Tubulin antibody was purchased from Sigma Aldrich (T9026, 1:5,000 dilution).

Immunoblotting.

Total protein concentrations of tissue homogenates and cell lysates were determined by Pierce BCA kit (Thermo Fisher). Homogenates or lysates were separated on 4-12% NuPAGE gels (Life Technologies) and transferred onto PVDF membranes (iBlot; Life Technologies). Membranes were blocked with 5% non-fat milk in TBST (0.1% Tween-20 in Tris-Buffered Saline) before overnight incubation with indicated antibodies. After incubation with the appropriate horseradish peroxidase-conjugated secondary antibodies, the bands were visualized by enhanced chemiluminescence (Pierce West Femto ECL). The intensity of the bands was quantified with Bio-Rad Quantity One software. When the IRDye secondary antibodies were used, the infrared signal was detected using an Odyssey scanner (Li-COR Biosciences) and the densitometry was performed using the Odyssey 2.1 Analyser software. The IRDye secondary antibodies anti-mouse (926-32212) and anti-mouse (926-68072) were purchased from Li-COR Biosciences and used at a 1:5,000 dilution. Statistical analysis of tissue densitometry levels were performed with GraphPad Prism software using the indicated statistical test.

Animals.

Mice were housed in pathogen-free animal facilities at NELS (New Haven, Conn.). All experiments were conducted under an approved protocol. Female CD-1 mice were obtained from Taconic Laboratories and implanted subcutaneously with 5×10⁶ MDA-MB-231 cells in Matrigel (Corning Life Science). After several weeks, mice bearing >100 mm³ tumors were randomized into two unblended groups with five mice in each group. One group served as a control for dosing vehicle, while the other group was given four administrations of PROTAC_ERRα (100 mg/kg, intraperitoneal, every eight hours). Mice were sacrificed five hours after final dose. Blood was collected, processed to plasma, and flash frozen. Tissues were harvested and flash frozen for further analysis. In vivo ERRα degradation using PROTAC_ERRα was reproduced two additional times using the same number of animals, dosing scheme and regimen. Sample size was estimated based on the variation in tissue ERRα levels seen from exploratory work before study initiation.

Tissue Homogenization.

Frozen kidney, heart, liver, and MDA-MB-231 tumors were thawed on ice, chopped into pieces, and placed into microfuge tubes with homogenization buffer (25 mM HEPES, 50 mM NaCl, 1% NP-40, 0.1% SDS, pH 7.4; 10 ml per mg tissue). Tissues were disrupted with a Qiagen TissueLyser bead miller (5 mm stainless steel bead; 2 min, 25 Hz), and homogenates were clarified (15,000 g, 10 min, 4° C.) and transferred to new tubes.

LC/MS for PROTAC Concentration Determination.

The concentration of PROTAC_ERRα was determined from snap-frozen plasma or tissue samples. The concentration of PROTAC_ERRα was quantified by use of a standard curve.

In Vitro Ubiquitination.

Ubiquitination reactions were performed in three stages. In the first stage, RIPK2 (final 500 nM) was incubated for 10 min at room temperature with [$^{32}$P]g-ATP in kinase buffer (25 mM Tris pH 7.5, 50 mM KCl, 2 mM Mg(CH$_3$CO$_2$)$_2$, 2 mM MnCl$_2$, 2 mM DTT) to radiolabel RIPK2 through auto-phosphorylation. In the second stage, ubiquitination buffer (25 mM Tris pH 7.5, 5 mM MgCl$_2$, 100 mM NaCl, 2 mM ATP, 0.1 mg/ml BSA, and 2 mM DTT) was added to complete auto-phosphorylation, and then VHL (final 250 nM) and indicated PROTACs (various concentrations) were added to the mixture to allow ternary complex formation. In parallel, UbE1 (final 25 nM), Ubc4 (final 250 nM), and ubiquitin (final 116 μM) were mixed in ubiquitination buffer to allow charging of the E2 enzyme with activated ubiquitin. In stage three of the reaction, the RIPK2-PROTAC-VHL and UbE1-Ubc4~Ub mixtures were combined, and incubated at room temperature for various times before being quenched with Sample Buffer containing 5% b-mercaptoethanol. Ubiquitinated RIPK2 was then separated by 4-15% SDS-PAGE and imaged using a PhosphoImager Screen overnight.

Calculation of RIPK2:

PROTAC stoichiometry. After PhosphoImager analysis, the gels were silver-stained, allowing visualization of the unmodified RIPK2 band. This band, along with the upper portion of each lane, was excised and radioactivity was quantified using PerkinElmer TriCarb 2700TR Liquid Scintillation Analyzer with a $^{32}$P efficiency of 73%. By using the specific activity on the day of analysis, this radioactivity was converted to moles of $^{32}$P. According to a mass spectrometric analysis, autophosphorylated RIPK2 protein has five phosphorylated tryptic peptides observed after the kinase reaction, which are absent in untreated protein. Using this information, moles of $^{32}$P were converted to moles of RIPK2, which can directly be compared to the moles of PROTAC used in each reaction.

Cell Treatment for Expression Proteomics Experiment.

THP-1 cells were seeded at a concentration of 3×10⁶ cells per well in 12 well plates in 1.5 ml growth medium (RPMI1640+10% heat-inactivated FBS). 500 μl of a 4× compound solution prepared in growth medium (DMSO, RIPK2-binding ligand, active or inactive RIPK2-PROTAC) were added and the cells were treated for the indicated periods (6, 18 or 24 h) at 37° C., 5% CO$_2$. For harvesting, the cells were collected into 2 ml tubes on ice, centrifuged and washed twice in cold PBS (Life Technologies). After the last washing step the supernatant was removed and the pellets were snap-frozen in liquid N$_2$ and stored at −80 OC until SDS lysis. MCF-7 cells were plated 1 day before the experiment at a concentration of 1×10⁶ cells per well in 6 well plates in growth medium (MEM+10% FBS+1% NEAA+sodium pyruvate) to let them recover and adhere. Medium was replaced with 1.5 ml fresh growth medium, and 500 μl of a 4× compound solution prepared in growth medium (DMSO, active or inactive ERRα-PROTAC) was added and the cells were treated for the indicated time points (4, 8 or 24 h) at 37° C., 5% $CO_2$. After treatment medium was removed and the cells were scraped in 1 ml ice cold PBS and collected into 1.5 ml tubes. Cells were washed with PBS and the supernatant was removed completely before cells were lysed in 2% SDS for 3 min at 95° C. in a thermomixer (Thermo Fisher Scientific), followed by digestion of DNA with Benzonase at 37° C. for 1.5 h. Lysate was cleared by centrifugation and protein concentration in the supernatant was determined by BCA assay. Proteins were reduced by DTT and alkylated with iodacetamide, separated on 4-12% NuPAGE (Invitrogen) gels and stained with colloidal Coomassie41 before trypsin digestion and mass spectrometric analysis.

Ternary Complex Formation.

THP-1 cells were harvested and lysed in lysis buffer (50 mM Tris-HCl, 5% Glycerol, 1.5 mM $MgCl_2$, 150 mM NaCl, 1 mM $Na_3VO_4$, 0.008% NP40 (Igepal), with Complete EDTA-free protease inhibitor cocktail). Mouse anti-VHL antibody (IgG1k, BD Biosciences) was immobilized at 0.125 μg antibody per μl agarose beads (AminoLink Plus, Thermo Fisher Scientific), and separately, mouse IgG1k at 0.125 μg antibody per μl agarose beads was immobilized as control antibody. PROTAC_RIPK2, PROTAC_RIPK2_epi and RIPK2-binding ligand were prepared in DMSO at 200 times the final assay concentration. THP-1 lysate was diluted to 5 mg/ml total protein concentration with IP buffer (50 mM Tris-HCl, 5% Glycerol, 1.5 mM $MgCl_2$, 150 mM NaCl, 1 mM $Na_3VO_4$, 0.008% NP40 (Igepal), Complete EDTA-free protease inhibitor cocktail tablet), and 10 mg total protein was incubated with 300 nM, 30 nM and 3 nM of PROTACs or 30 nM RIPK2-binding ligand or DMSO at 4° C. for 2 h. AminoLinked agarose beads were washed and equilibrated in IP buffer, and incubated with lysate compound mixture at 4° C. for 2 h. The beads were settled and supernatant was removed. The beads were washed twice with 30 times bed volume of IP buffer and once with 30 times bed volume of IP buffer without detergent. Bound protein was eluted from the agarose beads by 2$\xi$ Nupage buffer (Life Technologies) heated at 95° C. for 10 min. The eluate was separated from the agarose beads, and heated at 95° C. for 5 min after addition of DTT (final DTT concentration 50 mM in the sample). The eluate was subjected to Immunoblotting and LC-MS analysis.

Kinobeads Assays.

Competition binding assays were performed by using a modified bead matrix. Briefly, 1 ml (5 mg protein) cell extract was pre-incubated with test compound or vehicle for 45 min at 4° C. followed by incubation with Kinobeads (Cellzome; 35 ml beads per sample) for 1 h at 4° C. The nonbound fraction was removed by washing the beads with DP buffer (50 mM Tris-HCl, 0.8% (v/v) Igepal-CA630, 5% (v/v) glycerol, 150 mM NaCl, 1.5 mM $MgCl_2$, 25 mM NaF, 1 mM sodium vanadate, 1 mM dithiothreitol, Complete EDTA-free protease inhibitor tablet (Roche), pH 7.5). Proteins retained were eluted with 50 ml 2×SDS sample buffer. Proteins were alkylated with 200 mg/ml iodoacetamide for 30 min, partially separated on 4-12% NuPAGE (Invitrogen), and stained with colloidal Coomassie. PROTAC_RIPK2, PROTAC_RIPK2_epi and the RIPK2-binding ligand were tested at 3, 0.75, 0.18, 0.046, 0.012, 0.0029, 0.00073, 0.00018, and 0.000046 mM.

Sample Preparation for MS.

Gel lanes were cut into three slices covering the entire separation range (~2 cm) and subjected to in-gel digestion. Peptide samples were labeled with 10-plex TMT (TMT10, Thermo Fisher Scientific, Waltham, Mass.) reagents, enabling relative quantification of a broad range of 10 conditions in a single experiment. The labeling reaction was performed in 40 mM triethylammoniumbicarbonate, pH 8.53, at 22° C. and quenched with glycine. Labeled peptide extracts were combined to a single sample per experiment, and subjected to additional fractionation on an Ultimate3000 (Dionex, Sunnyvale, Calif.) by using reverse-phase chromatography at pH 12 [1 mm Xbridge column (Waters, Milford, Mass.)].

LC-MS/MS Analysis.

Samples were dried in vacuo and resuspended in 0.05% trifluoroacetic acid in water. Of the sample, 50% was injected into an Ultimate3000 nanoRLSC (Dionex, Sunnyvale, Calif.) coupled to a Q Exactive (Thermo Fisher Scientific). Peptides were trapped on a 5 mm×300 μm C18 column (Pepmap100, 5 μm, 300 Å, Thermo Fisher Scientific) in water with 0.05% TFA at 60° C. Separation was performed on custom 50 cm×100 mM (ID) reverse-phase columns (Reprosil) at 55° C. Gradient elution was performed from 2% acetonitrile to 40% acetonitrile in 0.1% formic acid and 3.5% DMSO over 2 h. Samples were online injected into Q-Exactive plus mass spectrometers operating with a data-dependent top 10 method. MS spectra were acquired by using 70.000 resolution and an ion target of $3\times10^6$. Higher energy collisional dissociation (HCD) scans were performed with 35% NCE at 35.000 resolution (at m/z 200), and the ion target settings was set to $2\times10^5$ so as to avoid coalescence. The instruments were operated with Tune 2.3 and Xcalibur 3.0.63.

Peptide and Protein Identification.

Mascot 2.4 (Matrix Science, Boston, Mass.) was used for protein identification by using a 10 p.p.m. mass tolerance for peptide precursors and 20 mD (HCD) mass tolerance for fragment ions. Carbamidomethylation of cysteine residues and TMT modification of lysine residues were set as fixed modifications and methionine oxidation, and N-terminal acetylation of proteins and TMT modification of peptide N termini were set as variable modifications. The search database consisted of a customized version of the International Protein Index protein sequence database combined with a decoy version of this database created by using a script supplied by Matrix Science. Unless stated otherwise protein identification was accepted as follows: (i) For single-spectrum to sequence assignments, this assignment was required to be the best match and a minimum Mascot score of 31 and a score difference of 10× the next best assignment. Based on these criteria, the decoy search results indicated <1% false discovery rate (FDR). (ii) For multiple spectrum to sequence assignments and using the same parameters, the decoy search results indicate <0.1% FDR.

Peptide and Protein Quantification.

Reporter ion intensities were read from raw data and multiplied with ion accumulation times (the unit is milliseconds) so as to yield a measure proportional to the number of ions; this measure is referred to as ion area. Spectra matching to peptides were filtered according to the following criteria: mascot ion score>15, signal-to-background of the precursor ion>4, and signal-to-interference>0.5. Fold changes were corrected for isotope purity as described and adjusted for interference caused by co-eluting nearly isobaric peaks as estimated by the signal-to-interference measure. Protein quantification was derived from individual spectra matching to distinct peptides by using a sum-based bootstrap algorithm; 95% confidence intervals were calculated for all protein fold changes that were quantified with more than three spectra. Protein fold changes were only reported for proteins with at least 2 quantified unique peptide matches. Dose-response curves were fitted using R (http://www dot r-project dot org/) and the drc package (http://www dot bioassay dot dk). All measured halfmaximum inhibitory concentration ($IC_{50}$) values were corrected for the influence of the immobilized ligand on the binding equilibrium using the Cheng-Prusoff relationship. Average relative $log_2$ fold changes for proteins in the ternary complex formation experiment were calculated for proteins quantified with 32 quantified unique peptide matches in both replicates. Relative protein abundances were generated based on MS1 abundances. XIC peaks were matched to the identified peptides. The apex of the XIC peak was required to be within 30 s from the time of the MS/MS event performed on the peptide precursor. The raw abundances of the XIC peaks of the peptides with identical sequences were summed (i.e., same sequence, but different charge states and/or different modifications), and the resulting single entity was referred to as a sequence. For each protein the 3 sequences with the highest raw XIC peak abundance from a given sample were selected and log 10-transformed. These values were then summed, and the mean was calculated. If less than 3 sequences were identified for a given protein, the mean was calculated on the 2 or 1 log 10-transformed MS1 values of the sequences.

Statistical Analysis.

Quantified proteins were divided into bins. The bins are constructed according to the number of quantified spectrum sequence matches. Each bin consists of at least 300 proteins. Once each bin has been completed, the remaining number of proteins is counted; if this number is below 300, the remaining proteins are added to the last completed bin. The statistical significance of differences in protein fold change was calculated using a z-test with a robust estimation of the standard deviation (using the 15.87, 50 and 84.13 percentiles) and calculating the P values for all measurements for a specific bin. Subsequently, an adjustment for multiple hypothesis testing was performed on the full data set by using Benjamini-Hochberg (BH) correction. Additionally proteins were filtered if the absolute log 2 fold change difference between the 2 replicate vehicle controls was >0.38. Finally, proteins were counted as regulated when they had P<0.05 and showed a change in expression in both replicates of 50% in the same direction.

LCMS Method:

The analysis was conducted on an Acquity UPLC BEH C18 column (50 mm×2.1 mm internal diameter 1.7 μm packing diameter) at 40° C. The solvents employed were: A=0.1% v/v solution of formic acid in water; B=0.1% v/v solution of formic acid in acetonitrile. The gradient employed was as follows:

| Time (minutes) | Flow Rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

The following illustrates the mobile phases and gradients used when compounds underwent purification by mass-directed autopreparative HPLC.

Mass-Directed Autopreparative HPLC (Formic Acid Modifier)

The HPLC analysis was conducted on a Sunfire C18 column (150 mm×30 mm internal diameter, 5 μm packing diameter) at ambient temperature. The solvents employed were A=0.1% v/v solution of formic acid in water; B=0.1% v/v solution of formic acid in acetonitrile.

Mass-Directed Autopreparative HPLC (Trifluoroacetic Acid Modifier)

The HPLC analysis was conducted on a Sunfire C18 column (150 mm×30 mm internal diameter, 5 μm packing diameter) at ambient temperature. The solvents employed were: A=0.1% v/v solution of trifluoroacetic acid in water; B=0.1% v/v solution of trifluoroacetic acid in acetonitrile.

Mass-Directed Autopreparative HPLC (Ammonium Bicarbonate Modifier)

The HPLC analysis was conducted on an XBridge C18 column (150 mm×30 mm internal diameter, 5 μm packing diameter) at ambient temperature. The solvents employed were: A=10 mM ammonium bicarbonate in water adjusted to pH 10 with ammonia solution; B=acetonitrile.

For each of the mass-directed autopreparative purifications, irrespective of the modifier used, the gradient employed was dependent upon the retention time of the particular compound undergoing purification as recorded in the analytical LCMS, and was as follows:

For compounds with an analytical LCMS retention time below 0.6 minutes the following gradient was used:

| Time (minutes) | Flow Rate (mL/min) | % A | % B |
|---|---|---|---|
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

For compounds with an analytical LCMS retention time between 0.6 and 0.9 minutes the following gradient was used:

| Time (minutes) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

For compounds with an analytical LCMS retention time between 0.9 and 1.2 minutes the following gradient was used:

| Time (minutes) | Flow Rate (mL/min) | % A | % B |
|---|---|---|---|
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

For compounds with an analytical LCMS retention time between 1.2 and 1.4 minutes the following gradient was used:

| Time (minutes) | Flow Rate (mL/min) | % A | % B |
|---|---|---|---|
| 0 | 40 | 50 | 50 |
| 1 | 40 | 50 | 50 |
| 10 | 40 | 1 | 99 |
| 11 | 40 | 1 | 99 |
| 15 | 40 | 1 | 99 |

For compounds with an analytical LCMS retention time greater than 1.4 minutes (LCMS method A) or greater than 3.6 minutes (LCMS method B) the following gradient was used:

| Time (minutes) | Flow Rate (mL/min) | % A | % B |
|---|---|---|---|
| 0 | 40 | 20 | 80 |
| 1 | 40 | 20 | 80 |
| 10 | 40 | 1 | 99 |
| 11 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionization.

General Methods of Chemical Synthesis

The following eight (8) general chemical synthetic methods (Methods A-F and Solid Phase Synthesis A-B, described hereinbelow) are provided for synthesizing compounds according to the present invention that are set forth in Table 2 Affinity Table above. Each method is presented with reference to a specific compound, the synthetic details of which are presented hereinabove. All of the compounds numbered may be synthesized using the methods which are set forth hereinbelow. In certain instances, more synthetic details are provided for certain exemplary embodiments in order to present that information such that it may serve as a template for synthesizing a number of other compounds as otherwise disclosed herein.

Synthesis of ULMs

Synthesis of 2S,4R)-1-((S)-2-amino-3,3-dimethylbutanoyl)-4-hydroxy-N-(4-(4-methylthiazol-5-yl)benzyl)pyrrolidine-2-carboxamide, hydrochloride

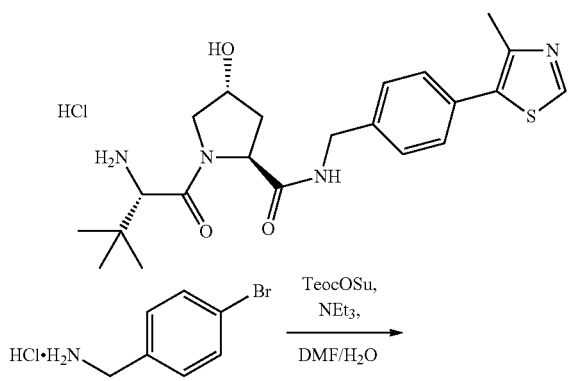

2-(trimethylsilyl)ethyl 4-bromobenzylcarbamate

4-Bromobenzylamine hydrochloride (354 mg, 1.59 mmol, 1 eq) was dissolved in DMF (6.4 mL) and water (2.1 mL) and stirred at room temperature. Triethylamine (0.33 mL, 2.39 mmol, 1.5 eq) and TeocOSu (454 mg, 1.75 mmol, 1.1 eq) were then added. After 12 hours, the mixture was diluted with EtOAc, washed with 1M HCl, saturated sodium bicarbonate, water and brine. The organic layer was then dried over sodium sulfate, filtered, and concentrated under reduced pressure. Purification by column chromatography (10 to 20% EtOAc/hexanes) gave a colorless oil (0.4158 g, 1.26 mmol, 79%). $^1$H NMR (500 MHz, CDCl$_3$) δ 7.48-7.43 (m, 2H), 7.17 (d, J=8.1 Hz, 2H), 4.94 (s, 1H), 4.31 (d, J=6.0 Hz, 2H), 4.23-4.15 (m, 2H), 1.04-0.93 (m, 2H), 0.04 (s, 9H). $^{13}$C NMR (126 MHz, CDCl$_3$) δ 156.91, 137.95, 131.88, 129.32, 121.43, 63.53, 44.53, 17.92, −1.32. MS (ESI) 354.1 (M+H).

2-(trimethylsilyl)ethyl 4-(4-methylthiazol-5-yl)benzylcarbamate 2-(Trimethylsilyl)ethyl 4-bromobenzylcarbamate (132 mg, 0.4 mmol, 1 eq), 4-methylthiazole-5-carboxylic acid (114.5 mg, 0.8 mmol, 2 eq), tetrabutylammonium chloride hydrate (118 mg, 0.4 mmol, 1 eq), cesium carbonate (196 mg, 0.6 mmol, 1.5 eq) and Pd(P(tBu)$_3$)$_2$ (40.8 mg, 0.08 mmol, 0.2 eq) were dissolved in DMF (4 mL). The reaction was heated to 170° C. in a microwave reactor for 16 minutes. The mixture was then cooled to room temperature, diluted with EtOAc and washed thrice with brine, once with saturated sodium bicarbonate, water, and then brine. The organic layer was dried over sodium sulfate, filtered and concentrated under reduced pressure. Purification by column chromatography (10 to 35% EtOAc/hexanes) gave a colorless oil (61.7 mg, 0.177 mmol, 44%). $^1$H NMR (400 MHz, CDCl$_3$) δ 8.67 (s, 1H), 7.43-7.37 (m, 2H), 7.34 (d, J=8.1 Hz, 2H), 5.09 (s, 1H), 4.39 (d, J=6.0 Hz, 2H), 4.28-4.02 (m, 2H), 2.52 (s, 3H), 1.10-0.90 (m, 2H), 0.14--0.09 (m, 9H). $^{13}$C NMR (101 MHz, CDCl$_3$) δ 156.98, 150.42, 148.66, 138.76, 131.67, 131.18, 129.66, 127.89, 63.46, 44.71, 17.90, 16.18, −1.34. MS (ESI) 349.0 (M+H).

(4-(4-methylthiazol-5-yl)phenyl)methanamine

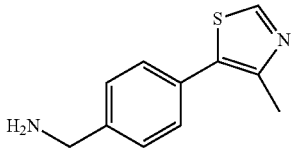

2-(trimethylsilyl)ethyl 4-(4-methylthiazol-5-yl)benzylcarbamate (51.8 mg, 0.149 mmol, 1 eq) was dissolved in acetonitrile (6 mL) at room temperature. A one molar solution of tetrabutylammonium fluoride in THF (0.45 mL, 0.45 mmol, 3 eq) was added and the solution was stirred for 24 hours. The mixture was concentrated under reduced pressure. Purification by column chromatography (0.5 to 4% 0.5N NH$_3$ (MeOH)/DCM) gave a light yellow oil (27.2 mg, 0.133 mmol, 89%). $^1$H NMR (500 MHz, MeOD) δ 8.87 (s, 1H), 7.44 (s, 4H), 3.85 (s, 2H), 2.47 (s, 3H). $^{13}$C NMR (126 MHz, MeOD) δ 152.77, 149.07, 143.63, 133.42, 131.46, 130.49, 129.05, 46.23, 15.79. MS (ESI) 205.0 (M+H).

Alternate Route:

4-bromobenzonitrile (5.1 g, 28 mmol, 1 eq), 4-methylthiazole (5.56 g, 56 mmol, 2 eq) potassium acetate (5.5 g, 56 mmol, 2 eq), palladium (II) acetate (63 mg, 0.28 mmol, 1 mol %) were dissolved in dimethylacetamide and stirred under argon (J. Org. Chem. 2009, 74:1179). The mixture was heated to 150° C. and stirred for 19 hours, then diluted with 500 mL EtOAc, and washed 4 times with 300 mL water. The first wash was then back extracted with 300 mL EtOAc, and then washed 4 times with 100 mL water. The combined organic layer was dried over sodium sulfate, filtered and concentrated under vacuum to give a beige solid (5.55 g, 27.7 mmol, 99%) that matched the reported spectral data. The solid was then dissolved in MeOH (280 mL) and cooled to 4° C. Cobalt chloride (9.9 g, 41.6 mmol, 1.5 eq) was added, followed by the slow, portionwise addition of sodium borohydride (5.2 g, 139 mmol, 5 eq), which was accompanied by vigorous bubbling. After 90 minutes, the reaction was quenched by the addition of water and ammonium hydroxide. The mixture was extracted 4 times with chloroform, and purified by column chromatography (10 to 30% 0.5M NH$_3$ (MeOH)/DCM) to give a darker oil (4.12 g, 20.2 mmol, 73%).

(2S,4R)-tert-butyl 2-((4-bromobenzyl)carbamoyl)-4-hydroxypyrrolidine-1-carboxylat

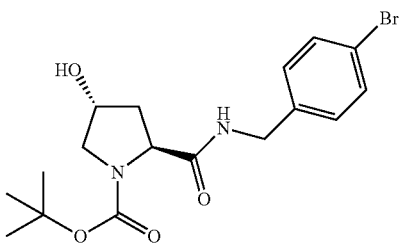 [SMILES: CC(C)(C)OC(=O)N1C[C@H](O)C[C@H]1C(=O)NCc1ccc(Br)cc1]

An ice-cooled mixture of (2S,4R)-1-(tert-butoxycarbonyl)-4-hydroxypyrrolidine-2-carboxylic acid (Aldrich) (7.95 g, 34 mmol) and (4-bromophenyl)methanamine (Fluorochem) (6.4 g, 34 mmol) in DMF (200 mL) was treated with DIPEA (18 mL, 103 mmol) and then with HATU (14.4 g, 38 mmol) and the mixture was stirred at ambient temperature for 30 minutes. The mixture was treated with water (200 mL) and extracted with ethyl acetate (2×200 mL). The combined organic phase was washed with saturated aqueous sodium bicarbonate (2×300 mL), water (100 mL), brine (200 mL), dried over magnesium sulfate and evaporated to dryness. The product was purified by flash chromatography (750 g silica cartridge) using a gradient elution from 0% to 10% methanol in dichloromethane to afford the title compound (12.9 g, 94% yield). LCMS RT=0.87 min, ES+ve m/z 401 [M+H]$^+$.

(2S,4R)-tert-butyl 4-hydroxy-2-((4-(4-methylthiazol-5-yl)benzyl)carbamoyl) pyrrolidine-1-carboxylate

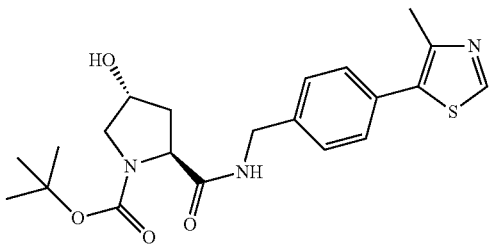 [SMILES: Cc1ncsc1-c1ccc(CNC(=O)[C@@H]2C[C@@H](O)CN2C(=O)OC(C)(C)C)cc1]

Under an atmosphere of nitrogen, a mixture of (2S,4R)-tert-butyl 2-((4-bromobenzyl)carbamoyl)-4-hydroxypyrrolidine-1-carboxylate (12.9 g, 32 mmol), 4-methyl thiazole (Aldrich) (5.9 mL, 65 mmol), palladium(II) acetate (Aldrich) (0.145 g, 0.65 mmol) and potassium acetate (6.34 g, 65 mmol) in N-methyl-2-pyrrolidone (80 mL) was stirred at 120° C. for 18 hours. After cooling to ambient temperature, water (100 ml) was added and the product was extracted with ethyl acetate (4×300 mL). The combined organic phase was washed with brine (5×200 mL), dried over magnesium sulfate and evaporated to dryness. The product was purified by flash chromatography (750 g silica cartridge) using a gradient elution from 0% to 10% methanol in dichloromethane to afford the title compound (8.0 g, 59% yield). LCMS RT=0.75 min, ES+ve m/z 418 [M+H]$^+$.

(2S,4R)-tert-butyl 4-hydroxy-2-((4-(4-methylthiazol-5-yl)benzyl)carbamoyl) pyrrolidine-1-carboxylate

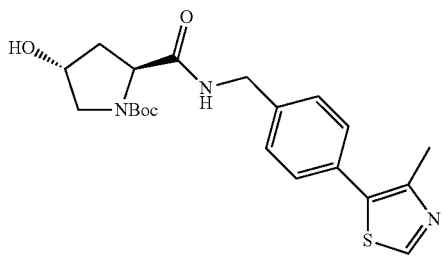 [SMILES: Cc1ncsc1-c1ccc(CNC(=O)[C@@H]2C[C@@H](O)CN2C(=O)OC(C)(C)C)cc1]

(2S,4R)-1-(tert-butoxycarbonyl)-4-hydroxypyrrolidine-2-carboxylic acid (366 mg, 1.58 mmol, 1 equiv.) was dissolved in 15 mL DMF and charged with EDC (380 mg, 2.0 mmol 1.3 equiv), and HOBt (310 mg, 2.0 mmol, 1.5 equiv) after 5 minutes of stirring (4-(4-methyl thiazol-5-yl)phenyl)methanamine (325 mg, 1.58 mmol, 1 equiv) was added. Upon stirring for 15 h the reaction was diluted with 25 mL EtOAc, and washed with 25 mL brine (2×), followed by 25 mL Sat. NaHCO$_3$ (2×). The organic layer was concentrated down to yield 650 mg (98% yield) of the product as a yellow oil. $^1$H NMR (400 MHz, CDCl$_3$) δ 8.67 (s, 1H), 7.43-7.29 (m, 4H), 4.49 (d, J=16.7 Hz, 4H), 3.51 (dd, J=11.0, 4.7 Hz, 2H), 2.61-2.45 (m, 4H), 2.03 (d, J=7.4 Hz, 2H), 1.42 (s, 9H). TLC: (9:1 DCM:MeOH (0.5 N NH$_3$)) R$_f$=0.20; MS (ESI) 417.5 (M+H)$^+$.

(2S,4R)-4-hydroxy-N-(4-(4-methylthiazol-5-yl)benzyl)pyrrolidine-2-carboxamide

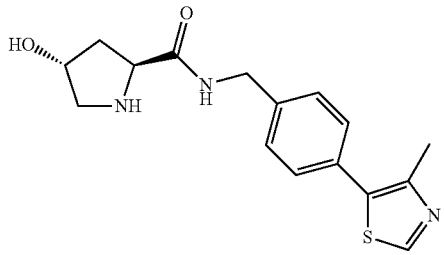 [SMILES: Cc1ncsc1-c1ccc(CNC(=O)[C@@H]2C[C@@H](O)CN2)cc1]

To (2S,4R)-tert-butyl 4-hydroxy-2-((4-(4-methylthiazol-5-yl)benzyl)carbamoyl) pyrrolidine-1-carboxylate (650 mg, 1.40 mmol, 1 equiv) in a round bottom flask was charged 9 mL 4M HCL in dioxanes (36 mmol, 26 equiv). The reaction was left to stir for 1 h upon which time N$_2$ was bubbled through for 1 h and the volatiles were removed by vacuum. The resulting viscous oil was washed dissolved in water and washed with 50 mL EtOAC. The aqueous layer was then basified to pH 12 with 1 M NaOH, and then extracted with 50 mL EtOAC (3×). The organic layer was dried and concentrated down to yield 250 mg (79% yield) of product as a brown viscous oil. $^1$H NMR (501 MHz, CDCl$_3$) δ 8.66 (s, 1H), 8.18 (t, J=6.0, 1H), 7.38 (d, J=8.1, 2H), 7.30 (d, J=8.1, 2H), 4.48-4.37 (m, 3H), 4.08 (t, J=8.4, 1H), 3.02 (d, J=13.3, 1H), 2.79 (dd, J=3.2, 12.3, 1H), 2.51 (s, 3H), 2.33 (dd, J=8.6, 13.9, 1H), 2.03-1.87 (m, 1H); $^{13}$C NMR (126 MHz, CDCl$_3$) δ 174.89, 150.35, 148.46, 138.30, 131.54, 130.95, 129.51, 127.92, 72.90, 59.72, 55.35, 42.53, 39.98, 16.06; TLC: (9:1 DCM:MeOH) R$_f$=0.1; LRMS (ESI) 317.4 (M+H)$^+$.

(2S,4R)-4-hydroxy-N-(4-(4-methylthiazol-5-yl)benzyl)pyrrolidine-2-carboxamide, hydrochloride

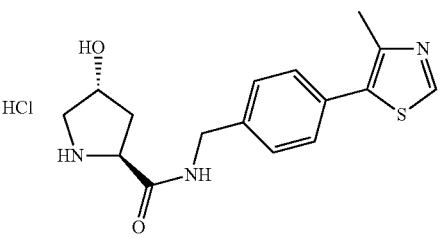 [SMILES: Cl ; Cc1ncsc1-c1ccc(CNC(=O)[C@@H]2C[C@@H](O)CN2)cc1]

A solution of (2S,4R)-tert-butyl 4-hydroxy-2-((4-(4-methylthiazol-5-yl)benzyl) carbamoyl)pyrrolidine-1-carboxylate (8 g, 19 mmol) in a mixture of methanol (30 mL) and dichloromethane (20 mL) was treated with 4M hydrochloric acid in 1,4-dioxane (8 mL, 32 mmol). The mixture was stirred at ambient temperature for 2 hours. The solvent was evaporated to dryness and the residue was triturated in dichloromethane, filtered and dried under vacuum to afford the title compound (6.7 g, 99% yield). LCMS RT=0.51 min, ES+ve m/z 318 [M+H]$^+$.

tert-butyl ((S)-1-((2S,4R)-4-hydroxy-2-((4-(4-methylthiazol-5-yl)benzyl) carbamoyl)pyrrolidin-1-yl)-3-methyl-1-oxobutan-2-yl)carbamate

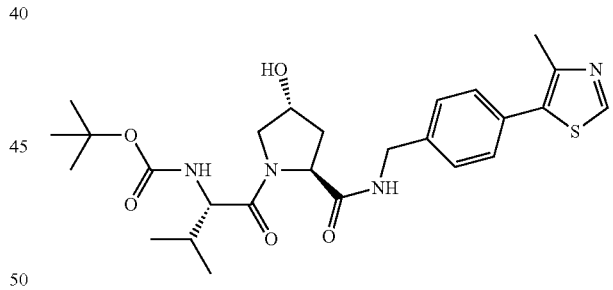

A stirred mixture of (2S,4R)-4-hydroxy-N-(4-(4-methylthiazol-5-yl)benzyl) pyrrolidine-2-carboxamide, hydrochloride (125 mg, 0.35 mmol) and (S)-2-((tert-butoxycarbonyl)amino)-3-methylbutanoic acid (Aldrich) (77 mg, 0.35 mmol) in DMF (0.9 mL) was treated with DIPEA (0.22 mL, 1.3 mmol) and then with HATU (134 mg, 0.35 mmol) and the mixture was stirred at ambient temperature for 1 hour. The product was subjected to purification by mass-directed automated preparative HPLC (formic acid modifier) to afford the title compound (120 mg, 72% yield). LCMS RT=0.87 min, ES+ve m/z 517 [M+H]$^+$.

Using a method analogous to that for tert-butyl-((S)-1-((2S,4R)-4-hydroxy-2-((4-(4-methylthiazol-5-yl)benzyl) carbamoyl)pyrrolidin-1-yl)-3-methyl-1-oxobutan-2-yl)carbamate, the following compounds were prepared:

| Name | Structure | Yield | RT | [M + H]+ |
|---|---|---|---|---|
| tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate | 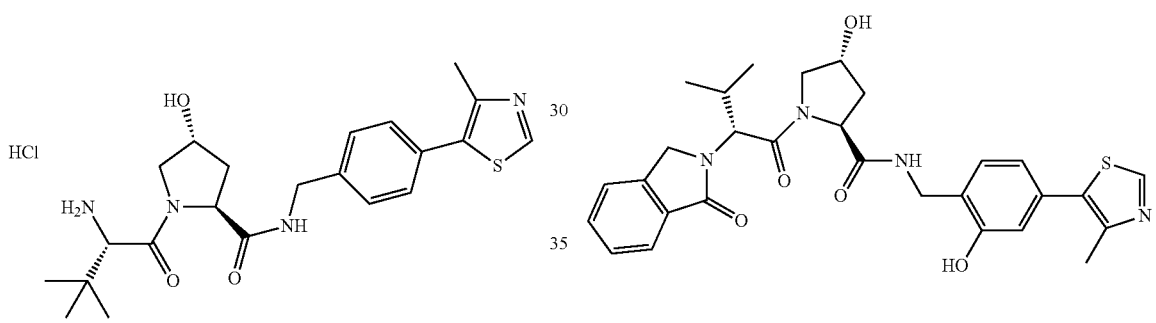 | 85% | 0.94 min | 531 |

(2S,4R)-1-((S)-2-amino-3,3-dimethylbutanoyl)-4-hydroxy-N-(4-(4-methyl thiazol-5-yl)benzyl)pyrrolidine-2-carboxamide hydrochloride A stirred mixture of (2S,4R)-4-hydroxy-N-(4-(4-methylthiazol-5-yl)benzyl) pyrrolidine-2-carboxamide, hydrochloride (70 mg, 0.20 mmol) and (S)-2-((tert-butoxycarbonyl)amino)-3,3-dimethylbutanoic acid (Fluka) (50 mg, 0.22 mmol) in DMF (1 mL) was treated with DIPEA (0.14 mL, 0.79 mmol) and then with HATU (90 mg, 0.24 mmol), and stirred at ambient temperature for 30 minutes. The product was subjected to purification by mass-directed automated preparative HPLC (formic acid modifier) to give the intermediate boc-protected product. The intermediate was then dissolved in a mixture of dichloromethane (0.5 mL) and methanol (0.1 mL) and treated with 4M hydrochloric acid in 1,4-dioxane (0.25 mL, 1.0 mmol). After stirring at ambient temperature for 1 hour, the reaction mixture was evaporated to dryness and the residue triturated to a solid with dichloromethane and dried under vacuum to afford the title compound (76 mg, 82% yield). LCMS RT=0.58 min, ES+ve m/z 431 [M+H]+.

Synthesis of (2S,4R)-4-hydroxy-N-(2-hydroxy-4-(4-methylthiazol-5-yl) benzyl)-1-((R)-3-methyl-2-(1-oxoisoindolin-2-yl)butanoyl)pyrrolidine-2-carboxamide 2-Hydroxy-4-(4-methylthiazol-5-yl)benzonitrile Under an atmosphere of nitrogen, a mixture of 4-bromo-2-hydroxybenzonitrile (Fluorochem) (15 g, 76 mmol), 4-methylthiazole (Aldrich) (14 mL, 152 mmol), potassium acetate (14.9 g, 152 mmol) and palladium(II) acetate (0.34 g, 1.52 mmol) in 1-methyl-2-pyrrolidone (125 mL) was heated at 110° C. for 3 hours. The mixture was then cooled to 50° C., poured into water (300 mL) and extracted with ethyl acetate (3×350 mL). The combined organic fraction was filtered and the filtrate was then washed with brine (3×400 mL), filtered through a hydrophobic frit and evaporated to dryness. The residue was reevaporated from toluene, then from diethyl ether, and then slurried in methanol to precipitate a yellow solid which was filtered off. The filtrate was evaporated to dryness and slurried in ice-cooled methanol to afford a second batch of yellow solid. The combined solid was dried under vacuum to afford the title compound (12 g, 56 mmol, 73% yield). LCMS RT=0.75 min, ES+ve m/z 217 [M+H]+.

2-(Aminomethyl)-5-(4-methylthiazol-5-yl)phenol

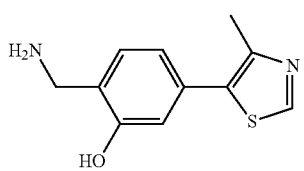

An ice-cooled solution of 2-hydroxy-4-(4-methylthiazol-5-yl)benzonitrile (12 g, 56 mmol) in THF (550 mL) was treated dropwise with lithium aluminium hydride (1M in THF, 140 mL, 140 mmol) over 5 minutes. The resulting mixture was then heated at 50° C. for 30 minutes and additional lithium aluminium hydride (1M in THF, 20 mL, 20 mmol) was added. After a further 30 minutes the mixture was cooled in an ice bath and treated cautiously with water (14 mL), followed by aqueous sodium hydroxide (4M, 42 mL, 168 mmol) and finally water (14 mL). After standing for 3 days, the mixture was filtered and the filtered solid was washed with THF. The combined filtrate was evaporated to dryness and the residue was slurried in dichloromethane:methanol (4:1) with Celite (about 20 g) and filtered. The filtered solid was washed three times with dichloromethane/methanol (4:1) and the combined filtrate was evaporated to dryness. The product was purified by flash chromatography (330 g silica cartridge) using a gradient elution from 0 to 15% methanol in dichloromethane (+1% triethylamine) to afford the title compound (6.2 g, 28 mmol, 51% yield). LCMS RT=0.41 min, ES+ve m/z 221 [M+H]⁺.

(2S,4R)-tert-Butyl 4-hydroxy-2-((2-hydroxy-4-(4-methylthiazol-5-yl)benzyl) carbamoyl)pyrrolidine-1-carboxylate

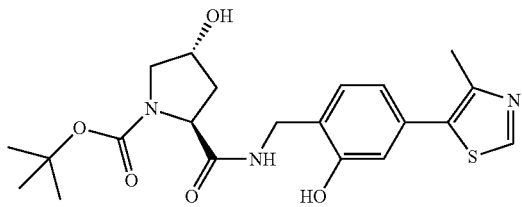 [SMILES: Cc1ncsc1-c1ccc(CNC(=O)[C@@H]2C[C@@H](O)CN2C(=O)OC(C)(C)C)c(O)c1]

An ice-cooled solution of 2-(aminomethyl)-5-(4-methylthiazol-5-yl)phenol (3.05 g, 13.8 mmol) and (2S,4R)-1-(tert-butoxycarbonyl)-4-hydroxypyrrolidine-2-carboxylic acid (2.94 mL, 13.8 mmol) in DMF (35 mL) was treated with DIPEA (7.25 mL, 42 mmol) followed by HATU (5.79 g, 15.2 mmol) and the mixture was stirred at ambient temperature for 1 hour. The mixture was treated with saturated aqueous sodium bicarbonate (50 mL) and extracted with ethyl acetate (3×80 mL). The combined organic phase was washed with brine (60 mL), filtered through a hydrophobic frit and evaporated to dryness. The product was purified by flash chromatography (330 g silica cartridge) using a gradient from 0 to 15% methanol in dichloromethane to afford the title product (4.8 g, 11 mmol, 80% yield). LCMS RT=0.76 min, ES+ve m/z 434 [M+H]⁺.

(2S,4R)-4-Hydroxy-N-(2-hydroxy-4-(4-methylthiazol-5-yl)benzyl)pyrrolidine-2-carboxamide, hydrochloride

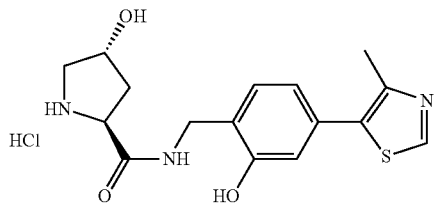 [SMILES: Cl ; Cc1ncsc1-c1ccc(CNC(=O)[C@@H]2C[C@@H](O)CN2)c(O)c1]

A solution of (2S,4R)-tert-butyl 4-hydroxy-2-((2-hydroxy-4-(4-methylthiazol-5-yl)benzyl)carbamoyl)pyrrolidine-1-carboxylate (4.8 g, 11 mmol) in dichloromethane:methanol 20:1 (50 mL) was treated with hydrochloric acid (4M in 1,4-dioxane) (35 mL, 140 mmol) and the mixture was stirred overnight at ambient temperature. The mixture was then evaporated to dryness and the residual solid was suspended in dichloromethane and filtered. The filtered solid was washed with further dichloromethane and dried under vacuum to afford the title compound (4 g, 10.8 mmol, 98% yield). LCMS RT=0.46 min, ES+ve m/z 334 [M+H]⁺.

(S)-2-(1-oxoisoindolin-2-yl)propanoic acid

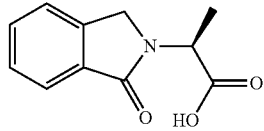

A mixture of phthalaldehyde (Aldrich) (4 g, 30 mmol) and (S)-2-aminopropanoic acid (Aldrich) (2.39 g, 27 mmol) in acetonitrile (150 mL) was heated at reflux for 5 hr then allowed to cool to ambient temperature and stood overnight. The resulting crystalline precipitate was filtered off, washed with acetonitrile and dried under vacuum to afford the title compound (4.46 g, 22 mmol, 73% yield). LCMS RT=0.59 min, ES+ve m/z 206 [M+H]⁺.

Using a method analogous to that for (S)-2-(1-oxoisoindolin-2-yl)propanoic acid, the following compounds were prepared:

| Name | Structure | Yield | RT | M + H]+ |
|---|---|---|---|---|
| (S)-3-methyl-2-(1-oxoisoindolin-2-yl)butanoic acid | 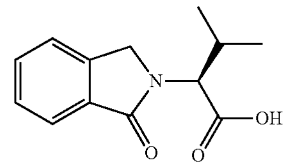 [SMILES: CC(C)[C@@H](C(=O)O)N1Cc2ccccc2C1=O] | 59% | 0.74 min | 234 |

(2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide

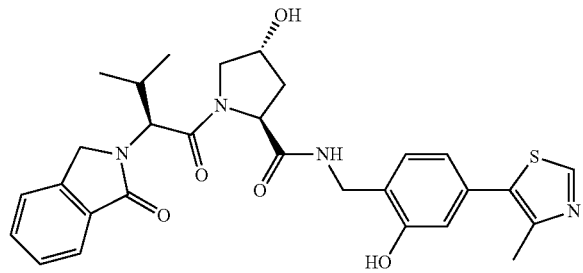 [SMILES: Cc1ncsc1-c1ccc(CNC(=O)[C@@H]2C[C@@H](O)CN2C(=O)[C@H](C(C)C)N2Cc3ccccc3C2=O)c(O)c1]

A mixture of (2S,4R)-4-hydroxy-N-(2-hydroxy-4-(4-methylthiazol-5-yl)benzyl) pyrrolidine-2-carboxamide, hydrochloride (125 mg, 0.34 mmol) and (S)-3-methyl-2-(1-oxoisoindolin-2-yl)butanoic acid (83 mg, 0.36 mmol) in DMF (1.6 mL) was treated with DIPEA (0.24 mL, 1.4 mmol) and HATU (140 mg, 0.37 mmol) and the mixture was stirred at ambient temperature for 30 minutes. The product was subjected to purification by mass-directed automated preparative HPLC (formic acid modifier) to afford the title compound (120 mg, 0.22 mmol, 65% yield). LCMS RT=0.81 min, ES+ve m/z 549 [M+H]$^+$.

(2S,4R)-4-hydroxy-N-(2-hydroxy-4-(4-methylthiazol-5-yl)benzyl)-1-((R)-3-methyl-2-(1-oxoisoindolin-2-yl)butanoyl)pyrrolidine-2-carboxamide

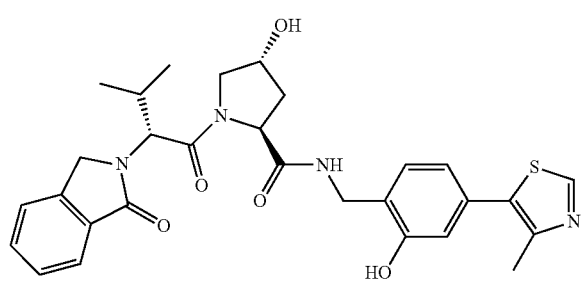 [SMILES: Cc1ncsc1-c1ccc(CNC(=O)[C@@H]2C[C@@H](O)CN2C(=O)[C@@H](C(C)C)N2Cc3ccccc3C2=O)c(O)c1]

A mixture of (2S,4R)-4-hydroxy-N-(2-hydroxy-4-(4-methylthiazol-5-yl)benzyl) pyrrolidine-2-carboxamide, hydrochloride (65 mg, 0.18 mmol) and (R)-3-methyl-2-(1-oxoisoindolin-2-yl)butanoic acid (43 mg, 0.19 mmol) in DMF (1.6 mL) was treated with DIPEA (0.123 mL, 0.70 mmol) and HATU (74 mg, 0.19 mmol) and the mixture was stirred at ambient temperature for 30 minutes. The product was subjected to purification by mass-directed automated preparative HPLC (formic acid modifier) to afford the title compound (64 mg, 0.12 mmol, 66% yield). LCMS RT=0.80 min, ES+ve m/z 549 [M+H]$^+$.

Synthesis of Exemplary Linkers

15-Bromo-1-phenyl-2,5,8,11-tetraoxapentadecane

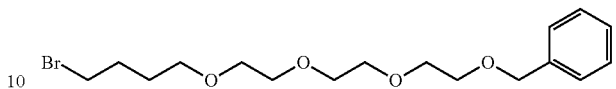

To a suspension of sodium hydride, 60% w/w in mineral oil (0.250 g, 6.24 mmol) in DMF (2 mL) was added a solution of 2-(2-(2-(benzyloxy)ethoxy)ethoxy)ethanol (1 g, 4.16 mmol) (Fluorochem) in DMF (2 mL) at 0° C. After stirring for 25 minutes, 1,4-dibromobutane (Aldrich) (4.04 g, 18.73 mmol) dissolved in DMF (2 mL) was added dropwise to the mixture. The reaction was stirred under an atmosphere of nitrogen for 2.5 hours. A further aliquot of sodium hydride, 60% w/w in mineral oil (0.250 g, 6.24 mmol) was added and the reaction was stirred at 0° C. for 30 minutes. The reaction was warmed to room temperature and stirred for 30 minutes. A final aliquot of sodium hydride, 60% w/w in mineral oil (0.250 g, 6.24 mmol), was added and the reaction stirred at room temperature for 2 hours then left standing over the weekend. The reaction mixture was filtered through celite and the solid washed with DCM. The filtrate was partitioned between DCM (30 mL) and water (30 mL). The organic extract was washed with brine (2×30 mL), dried using a hydrophobic frit and concentrated under reduced pressure. The product was purified by chromatography on silica using a gradient elution from 0% to 100% methyl tert-butyl ether in cyclohexane to afford the title compound (711 mg, 1.89 mmol, 46% yield). LCMS RT=1.16 min, ES+ve m/z 375.2/377.1 [M+H]$^+$.

15-Iodo-1-phenyl-2,5,8,11-tetraoxapentadecane

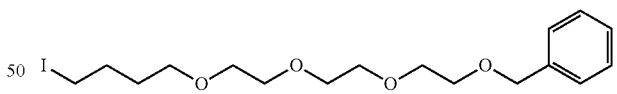

A mixture of 15-bromo-1-phenyl-2,5,8,11-tetraoxapentadecane (711 mg, 1.894 mmol) and sodium iodide (568 mg, 3.79 mmol) in acetone (10 mL) was heated under reflux conditions for 4 hours. The reaction was cooled to room temperature. The mixture was filtered through celite and the solid washed with acetone. The solvent was removed under reduced pressure. The residue was dissolved in ethyl acetate (30 mL) and washed with water (30 mL) and brine (2×30 mL). The organic extract was dried using a hydrophobic frit and concentrated under reduced pressure to afford the title compound (759 mg, 1.797 mmol, 95% yield). LCMS RT=1.23 min, ES+ve m/z 440.0 [M+NH$_4$]$^+$.

Additional Synthetic Methods for Preparing the Compounds of the Invention
Amide Coupling Route
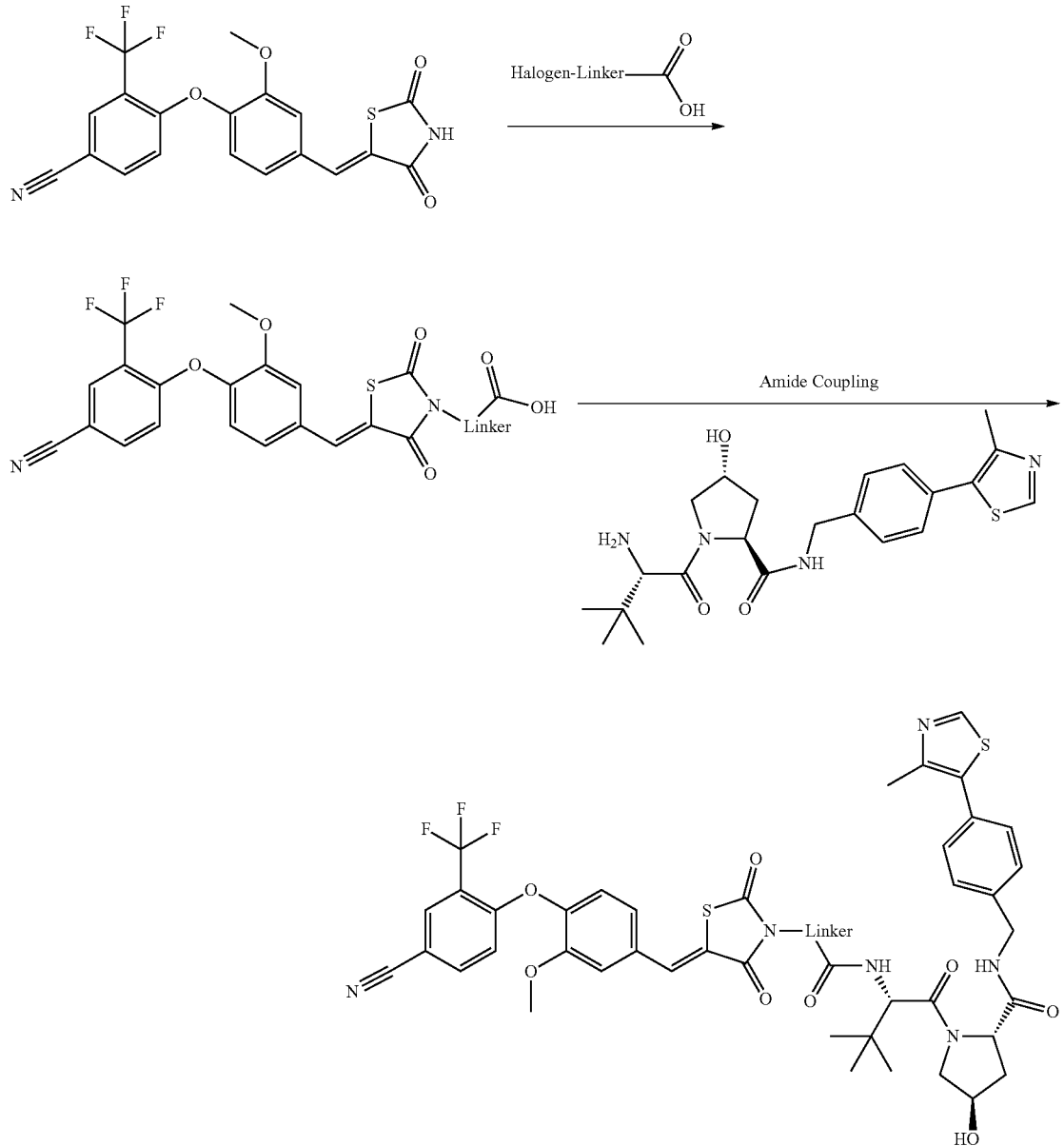
Compounds ARV N000020, ARV N000200, ARV N000201, ARV N000203, ARV N000223, ARV N000224, ARV N000234, ARV N000235, ARV N000236, ARV N000244, ARV N000245, ARV N000246, ARV N000267, ARV N000381, ARV N000382, ARV N000413, ARV N000383, and ARV N000414 can be prepared according to the above Amide Coupling Route.
Mitsonobu Route
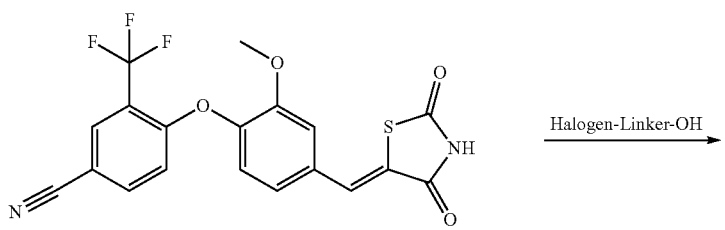

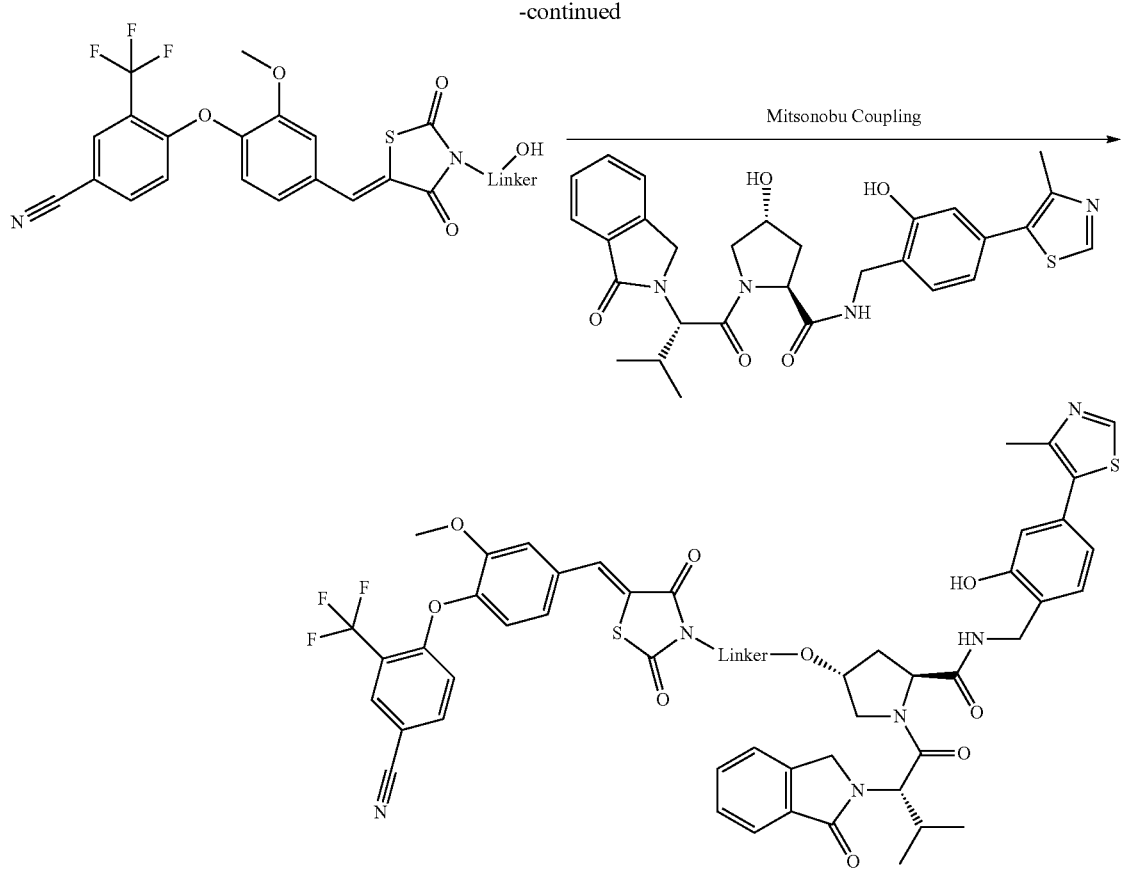

Compounds ARV N000198, ARV N000199, ARV N000219, ARV N000220, ARV N000221, ARV N000222, ARV N000231, ARV N000232, ARV N000233, ARV N000265, and ARV N000266 can be prepared according to the above Amide Coupling Route.

Using the methods as described herein, the following exemplary PROTAC compounds were prepared (see Table below). The exemplary compounds were also assayed for their ability to effectuate the degration of ERRα in either MCF-7 cells or ST-486 cells. Thus, in certain embodiments, the description provides the compounds below, including compositions comprising effective amount of a compound as listed below or a derivative, analog, or a prodrug of the same, in combination with at least one of a pharmaceutically acceptable carrier, another active agent, including a second PROTAC molecule as described herein or a combination thereof. In additional embodiments, the disclosure provides a method of treating a disease or condition in a subject in need thereof, comprising administering a composition comprising an effective amount of a compound listed below, wherein the composition is effective for treating or ameliorating a symptom of the disease or condition.

ERRα Degradation Data for Select Compounds of the Invention

Legend for following table: A=ERRα Degradation Dmax (Estimated) MCF-7 cells; B=ERRα Degradation $DC_{50}$ (Estimated) MCF-7 cells; C=ERRα Degradation Dmax (Estimated) ST-486 cells; D=ERRα Degradation $DC_{50}$ (Estimated) ST-486 cells

| ID | Compound Structure | A | B | C | D |
|---|---|---|---|---|---|
| ARV N000020 | 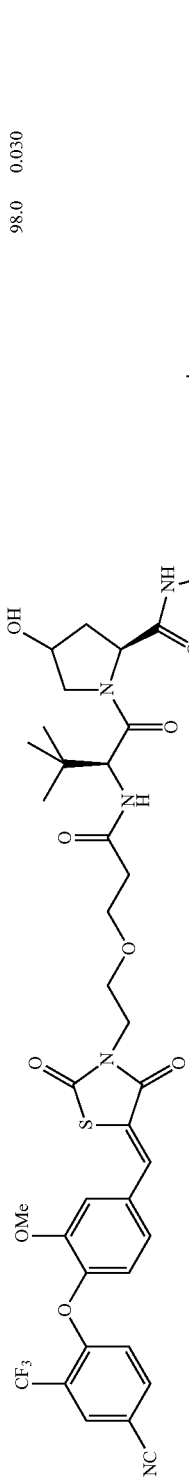 | 98.0 | 0.030 | | |
| ARV N000198 | 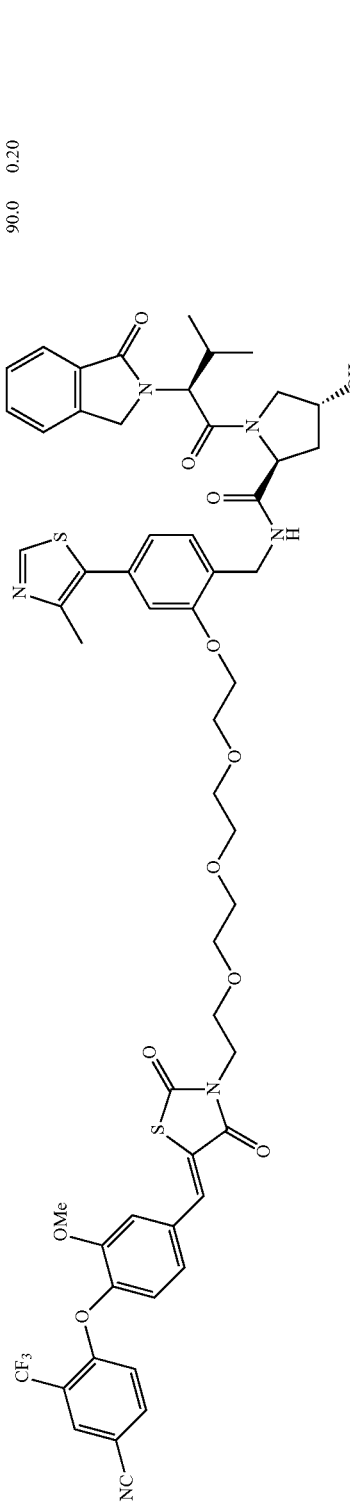 | 90.0 | 0.20 | | |
| ARV N000199 | 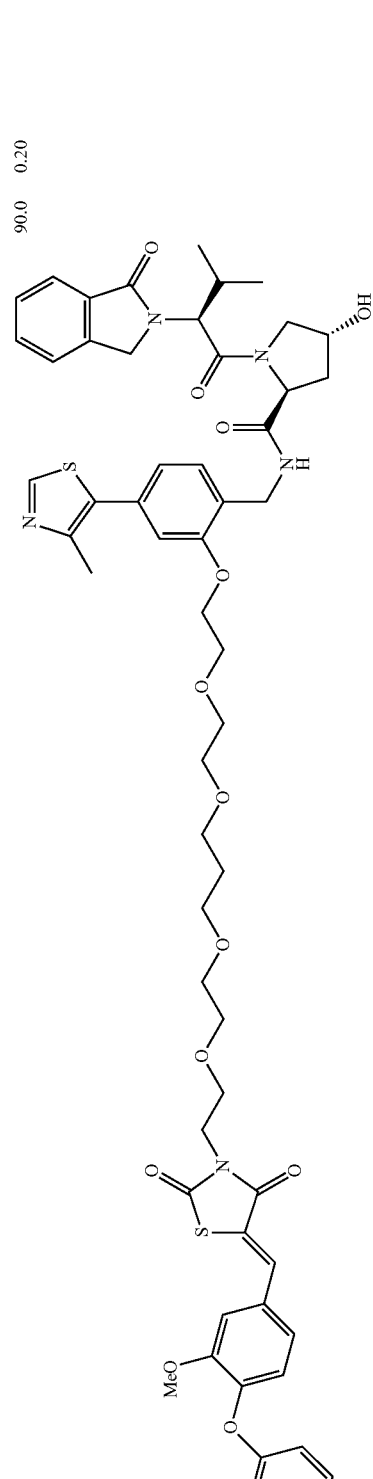 | 90.0 | 0.20 | | |

-continued

| ID | Compound Structure | A | B | C | D |
|---|---|---|---|---|---|
| ARV N000200 | 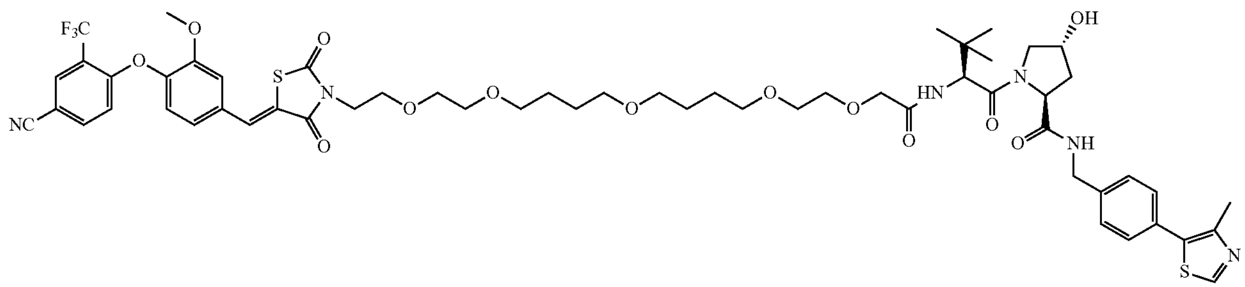 [SMILES: COc1cc(/C=C2\SC(=O)N(CCOCCOCCCCOCCCCOCCOCC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | 80.0 | 2.0 | | |
| ARV N000201 | 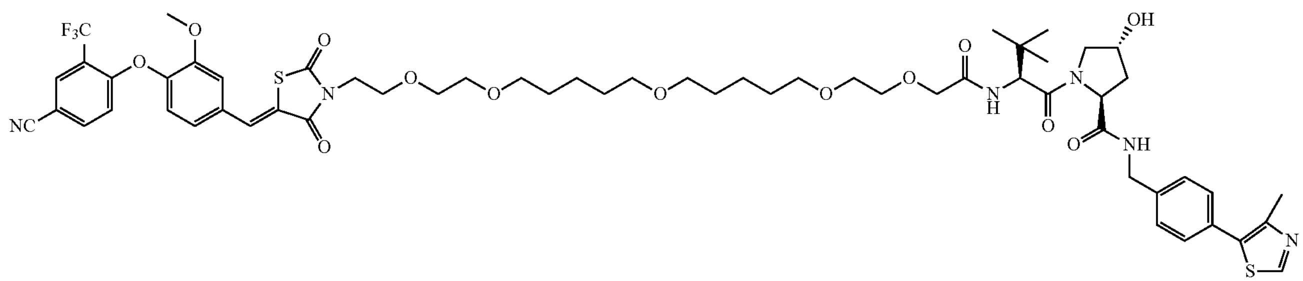 [SMILES: COc1cc(/C=C2\SC(=O)N(CCOCCOCCCCCOCCCCCOCCOCC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | 90.0 | 2.0 | | |
| ARV N000203 | 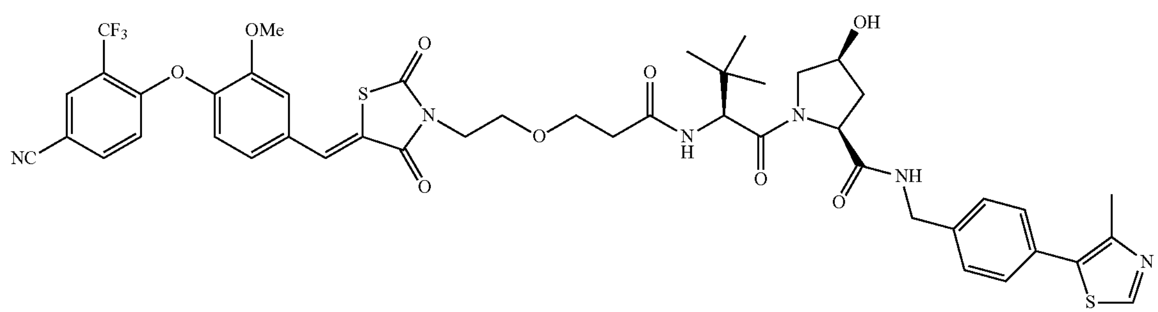 [SMILES: COc1cc(/C=C2\SC(=O)N(CCOCCC(=O)N[C@H](C(=O)N3C[C@@H](O)C[C@H]3C(=O)NCc3ccc(-c4scnc4C)cc3)C(C)(C)C)C2=O)ccc1Oc1ccc(C#N)cc1C(F)(F)F] | 40.0 | 2.0 | | |

-continued
| ID | Compound Structure | A | B | C | D |
|---|---|---|---|---|---|
| ARV N000219 | 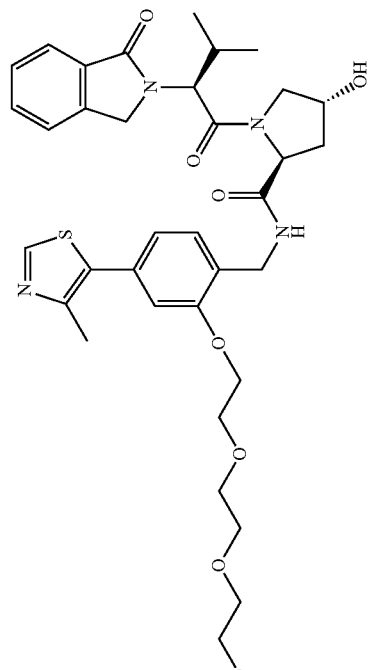 | 98.0 | 0.30 | | |
| ARV N000220 | 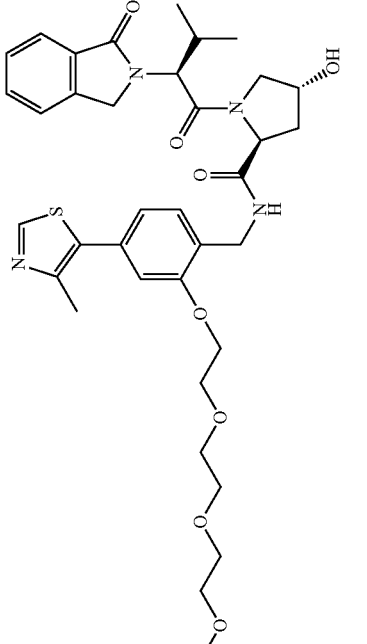 | 85.0 | 0.70 | | |

| ID | Compound Structure | A | B | C | D |
|---|---|---|---|---|---|
| ARV N000221 | 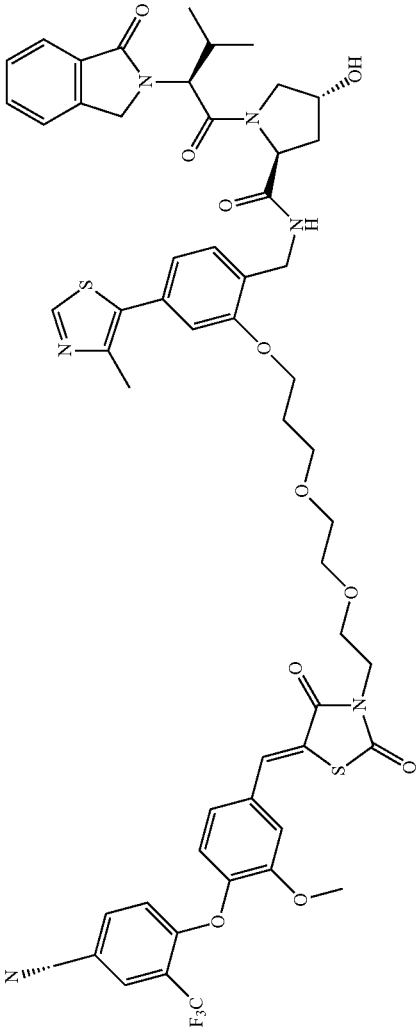 | 90.0 | 0.70 | | |
| ARV N000222 | 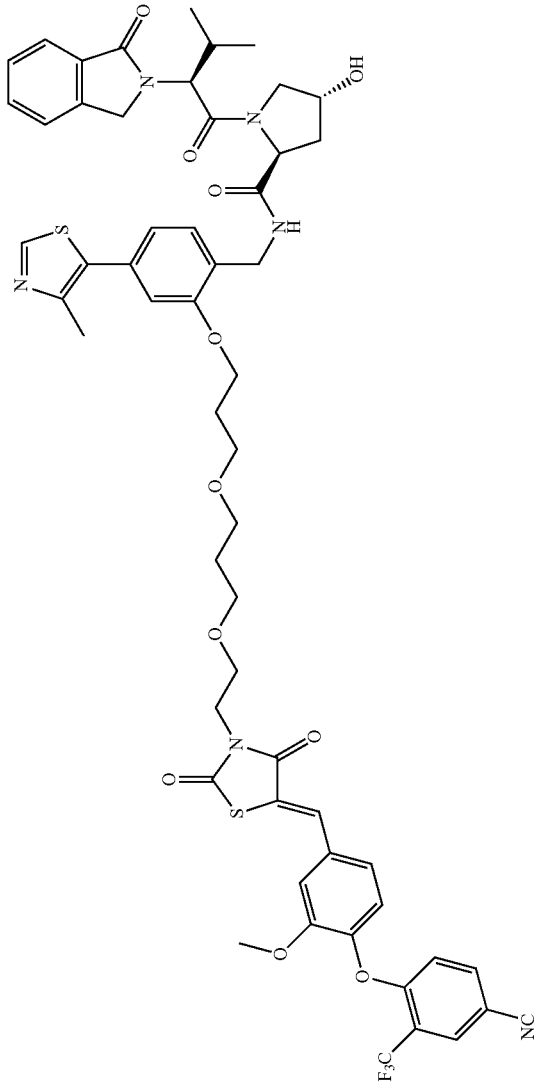 | 90.0 | 0.20 | | |

| ID | Compound Structure | A | B | C | D |
|---|---|---|---|---|---|
| ARV N000223 | 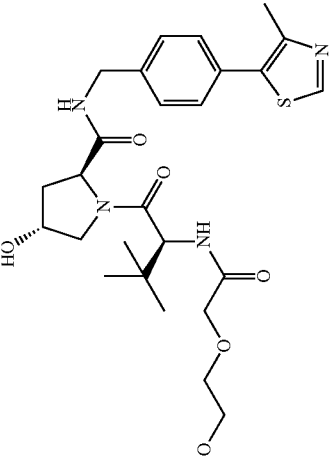 | 80.0 | 0.30 | | |
| ARV N000224 | 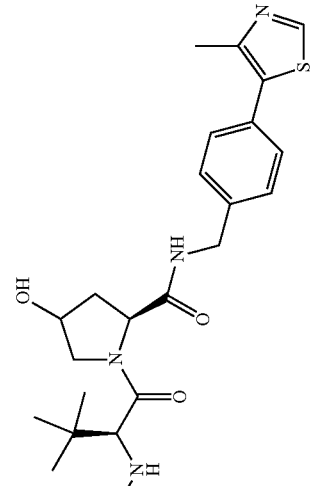 | 90.0 | 0.70 | | |

-continued

| ID | Compound Structure | A | B | C | D |
|---|---|---|---|---|---|
| ARV N000231 | 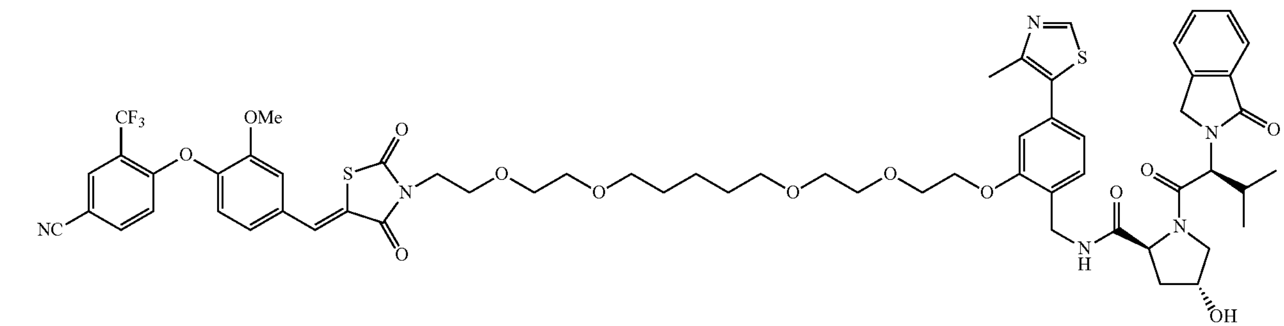 [SMILES: COc1cc(/C=C2\SC(=O)N(CCOCCOCCCCCOCCOCCOc3cc(-c4scnc4C)ccc3CNC(=O)[C@@H]3C[C@@H](O)CN3C(=O)[C@H](C(C)C)N3Cc4ccccc4C3=O)C2=O)ccc1Oc1ccc(C#N)cc1C(F)(F)F] | 98.0 | 0.20 | | |
| ARV N000232 | 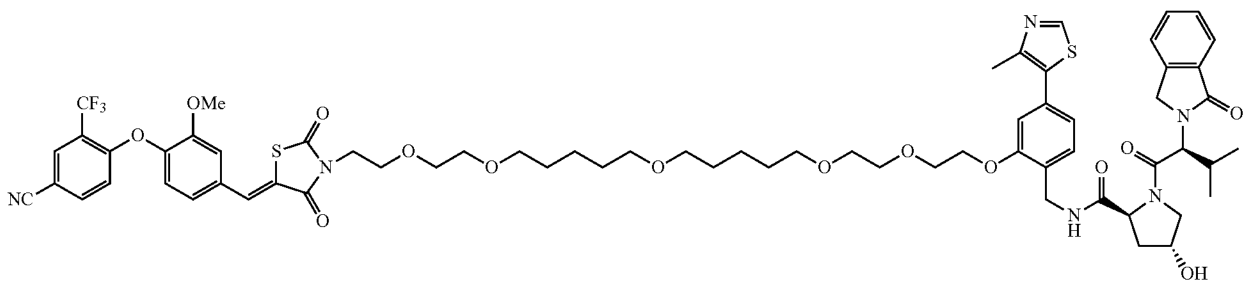 [SMILES: COc1cc(/C=C2\SC(=O)N(CCOCCOCCCCCOCCCCCOCCOCCOc3cc(-c4scnc4C)ccc3CNC(=O)[C@@H]3C[C@@H](O)CN3C(=O)[C@H](C(C)C)N3Cc4ccccc4C3=O)C2=O)ccc1Oc1ccc(C#N)cc1C(F)(F)F] | 60.0 | 2.0 | | |
| ARV N000233 | 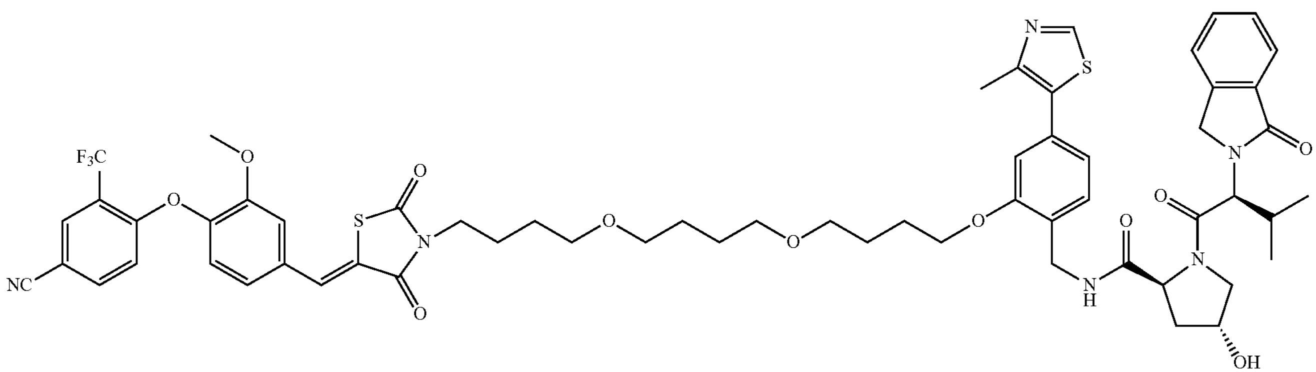 [SMILES: COc1cc(/C=C2\SC(=O)N(CCCCOCCCCOCCCCOc3cc(-c4scnc4C)ccc3CNC(=O)[C@@H]3C[C@@H](O)CN3C(=O)[C@H](C(C)C)N3Cc4ccccc4C3=O)C2=O)ccc1Oc1ccc(C#N)cc1C(F)(F)F] | 60.0 | 0.50 | | |

-continued

| ID | Compound Structure | A | B | C | D |
|---|---|---|---|---|---|
| ARV N000234 | 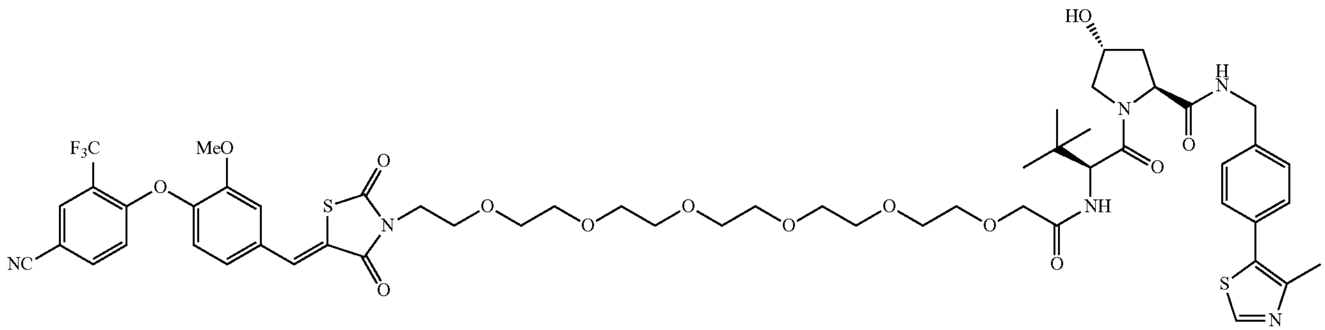 [SMILES: COc1cc(/C=C2\SC(=O)N(CCOCCOCCOCCOCCOCCOCC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | 98.0 | 0.030 | | |
| ARV N000235 | 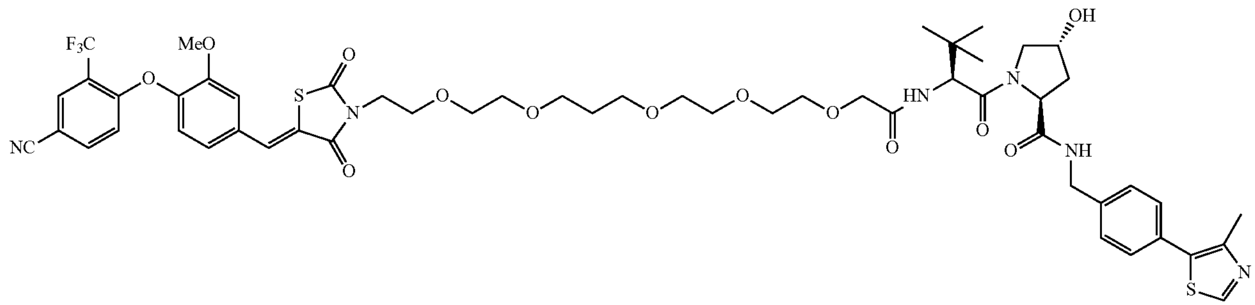 [SMILES: COc1cc(/C=C2\SC(=O)N(CCOCCOCCCOCCOCCOCC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | 95.0 | 0.10 | | |
| ARV N000236 | 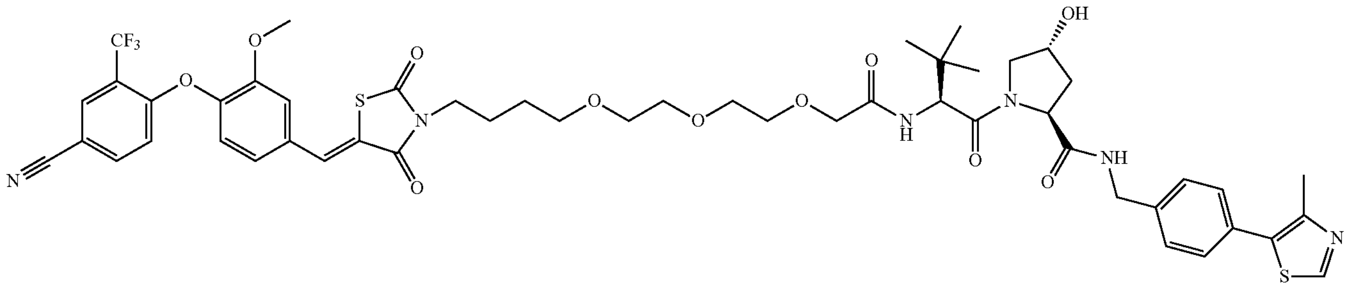 [SMILES: COc1cc(/C=C2\SC(=O)N(CCCCOCCOCCOCC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | 90.0 | 0.70 | | |

-continued

| ID | Compound Structure | A | B | C | D |
|---|---|---|---|---|---|
| ARV N000244 | 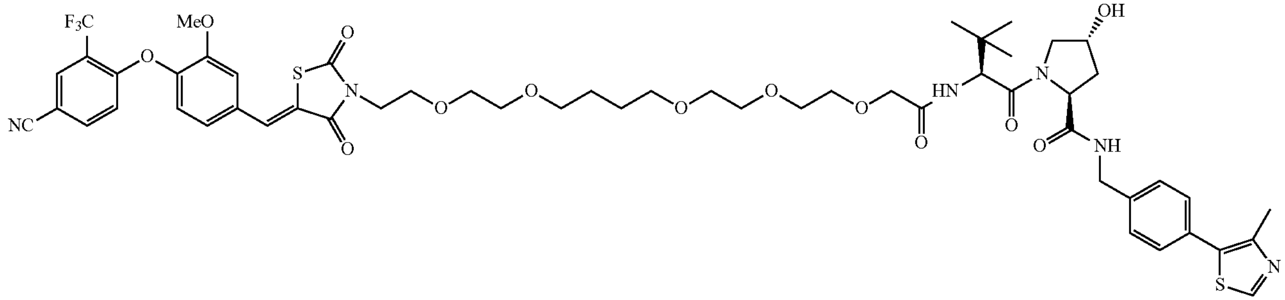 [SMILES: COc1cc(/C=C2\SC(=O)N(CCOCCOCCCCOCCOCCOCC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | | | 80.0 | 0.70 |
| ARV N000245 | 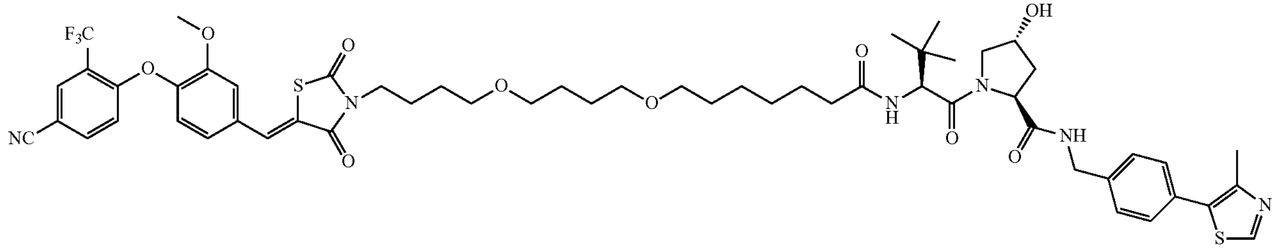 [SMILES: COc1cc(/C=C2\SC(=O)N(CCCCOCCCCOCCCCCCC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | | | 40.0 | 1.0 |
| ARV N000246 | 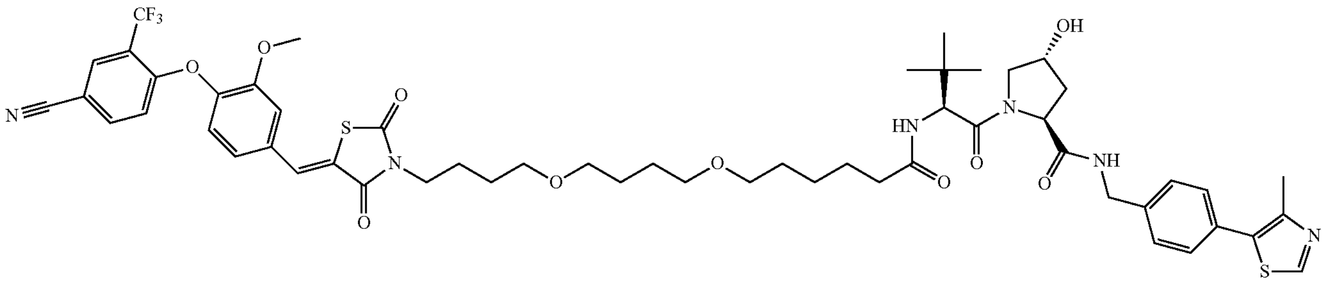 [SMILES: COc1cc(/C=C2\SC(=O)N(CCCCOCCCCOCCCCCC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | | | 90.0 | 0.30 |

-continued

| ID | Compound Structure | A | B | C | D |
|---|---|---|---|---|---|
| ARV N000265 | 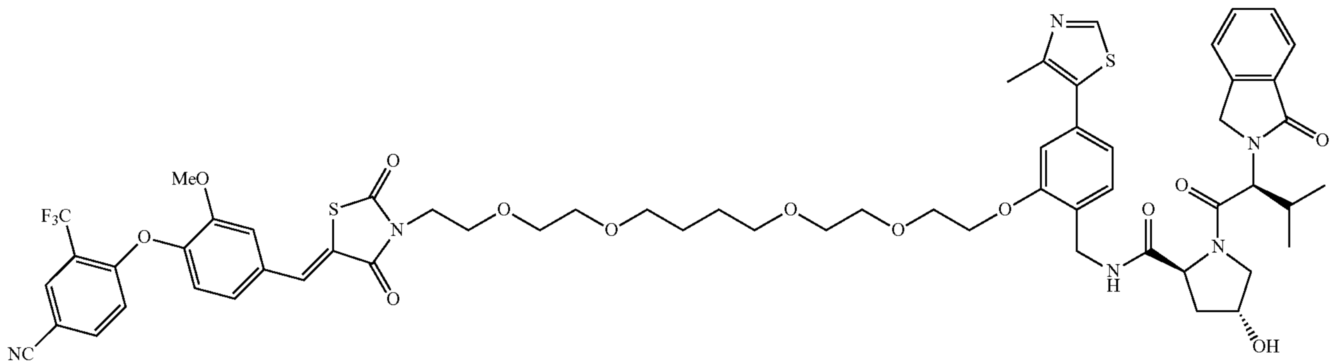 [SMILES: COc1cc(/C=C2\SC(=O)N(CCOCCOCCCCOCCOCCOc3cc(-c4scnc4C)ccc3CNC(=O)[C@@H]3C[C@@H](O)CN3C(=O)[C@H](C(C)C)N3Cc4ccccc4C3=O)C2=O)ccc1Oc1ccc(C#N)cc1C(F)(F)F] | | | 80.0 | 0.20 |
| ARV N000266 | 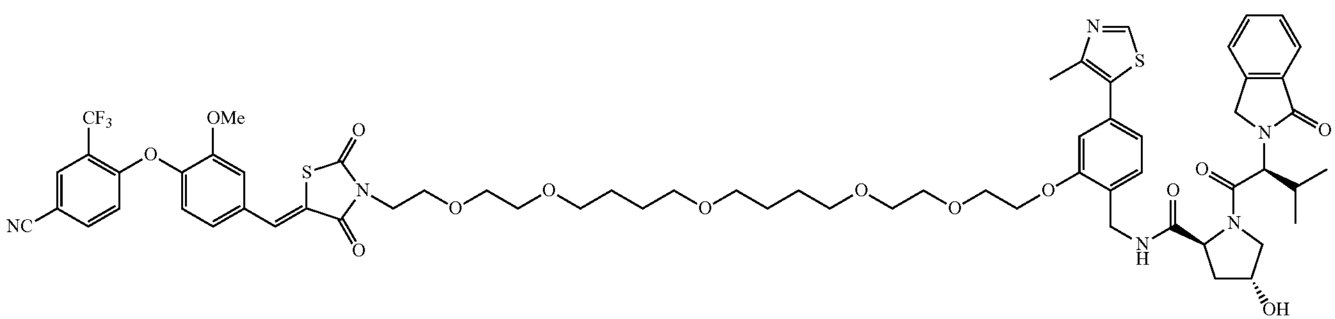 [SMILES: COc1cc(/C=C2\SC(=O)N(CCOCCOCCCCOCCCCOCCOCCOc3cc(-c4scnc4C)ccc3CNC(=O)[C@@H]3C[C@@H](O)CN3C(=O)[C@H](C(C)C)N3Cc4ccccc4C3=O)C2=O)ccc1Oc1ccc(C#N)cc1C(F)(F)F] | | | 50.0 | 0.50 |

| ID | Compound Structure | A | B | C | D |
|---|---|---|---|---|---|
| ARV N000267 | 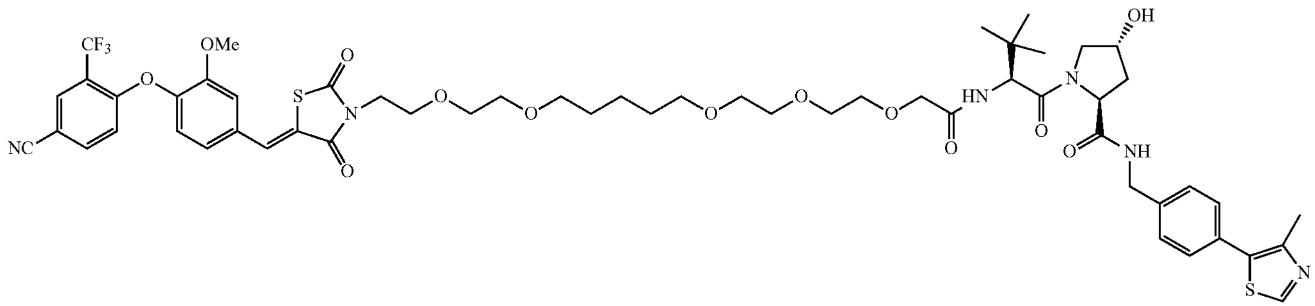 [SMILES: COc1cc(/C=C2\SC(=O)N(CCOCCOCCCCCOCCOCCOCC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | | | 80.0 | 0.50 |
| ARV N000381 | 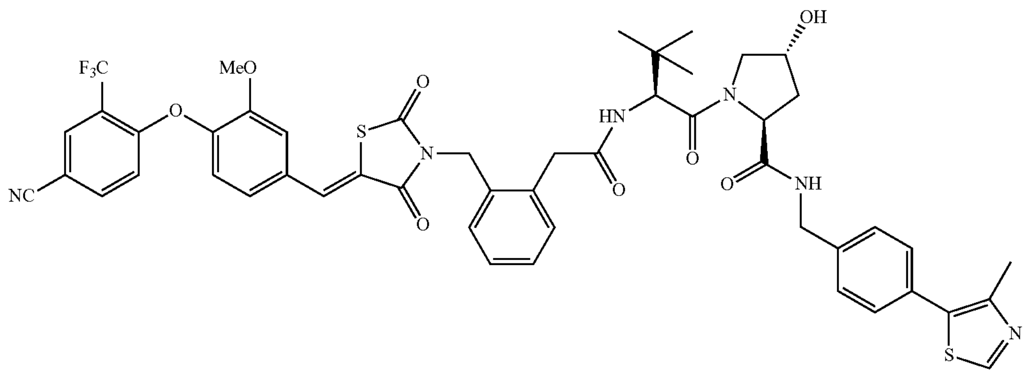 [SMILES: COc1cc(/C=C2\SC(=O)N(Cc3ccccc3CC(=O)N[C@H](C(=O)N3C[C@H](O)C[C@H]3C(=O)NCc3ccc(-c4scnc4C)cc3)C(C)(C)C)C2=O)ccc1Oc1ccc(C#N)cc1C(F)(F)F] | | | 98.0 | 0.030 |

| ID | Compound Structure | A | B | C | D |
|---|---|---|---|---|---|
| ARV N000382 | 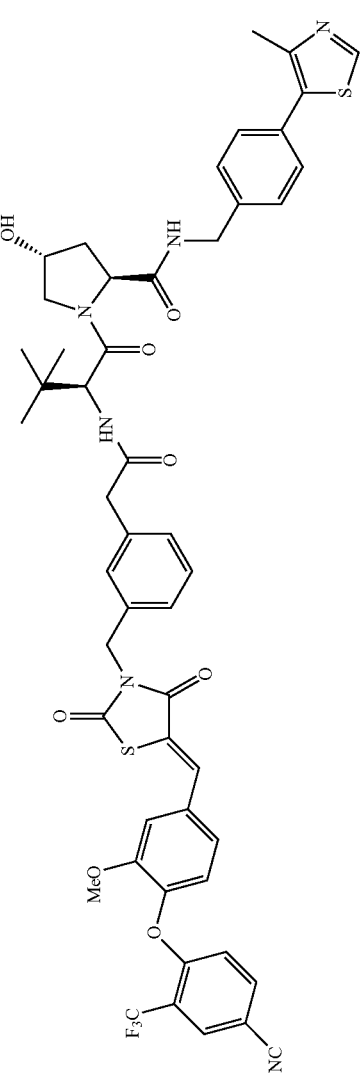 | | | 98.0 | 0.030 |
| ARV N000413 | 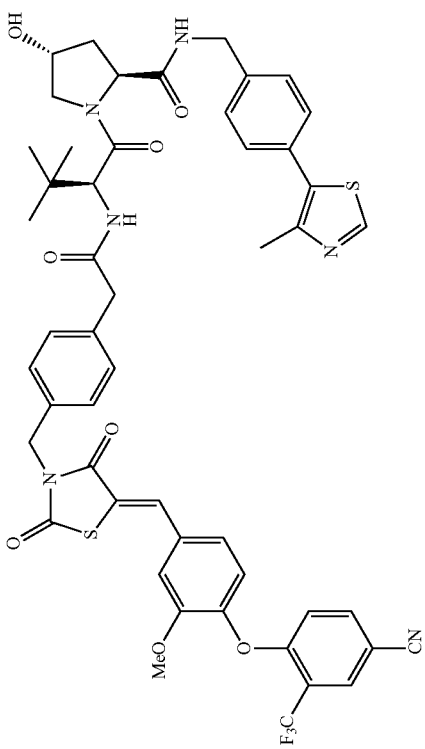 | | | 98.0 | 0.070 |

-continued
| ID | Compound Structure | A | B | C | D |
|---|---|---|---|---|---|
| ARV N000383 | 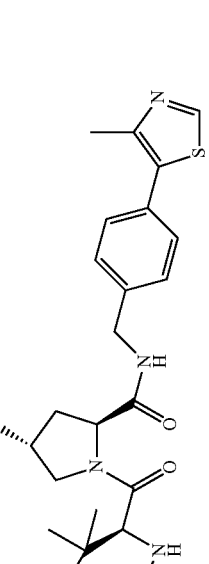 | | | 98.0 | 0.20 |
| ARV N000414 | 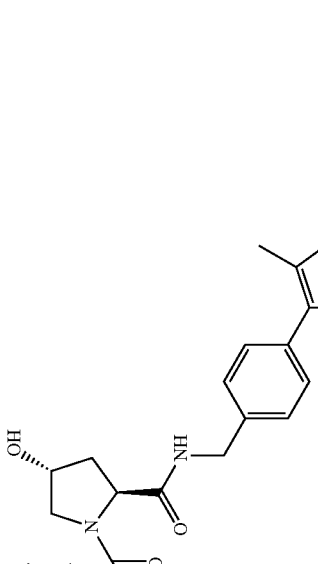 | | | 98.0 | 0.070 |

Figure 1A:
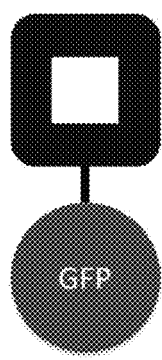
FIG. 1A depicts HALOTAG™ protein, which is known to irreversibly bind to chloroalkanes, linked to GFP.
Figure 1B:
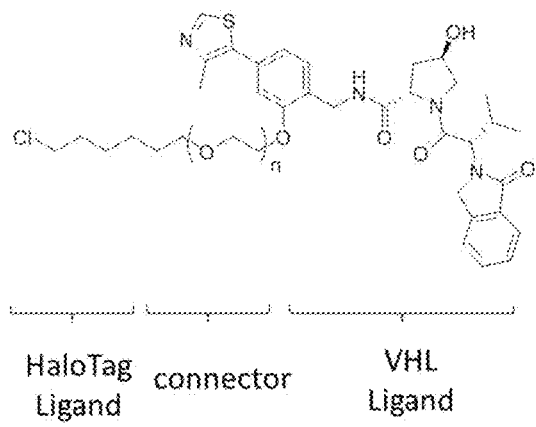
FIG. 1B depicts a ligand comprising a HALOTAG™ ligand, a polyethylene glycol-containing linker, and a VHL ligand, for measuring the timecourse of HALOTAGT protein degradation.
Figure 2:
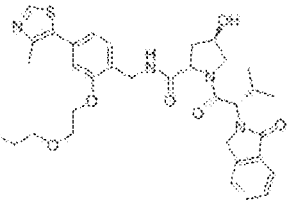
FIG. 2 depicts the stereochemical dependence at the 4-hydroxyl position of the ligand on the degradation of the HALOTAG™ protein. The (S)-isomomer was less effective at affecting HALOTAGT protein degradation than the (R)-isomer.
Figure 2:
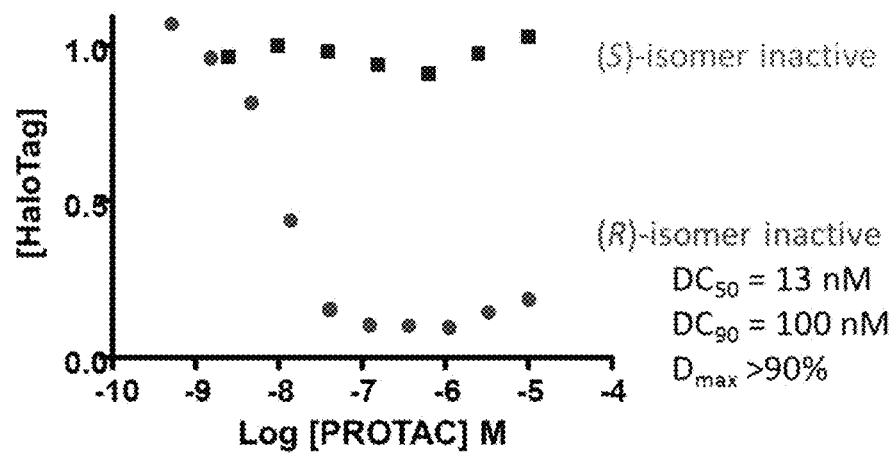
Figure 3A:
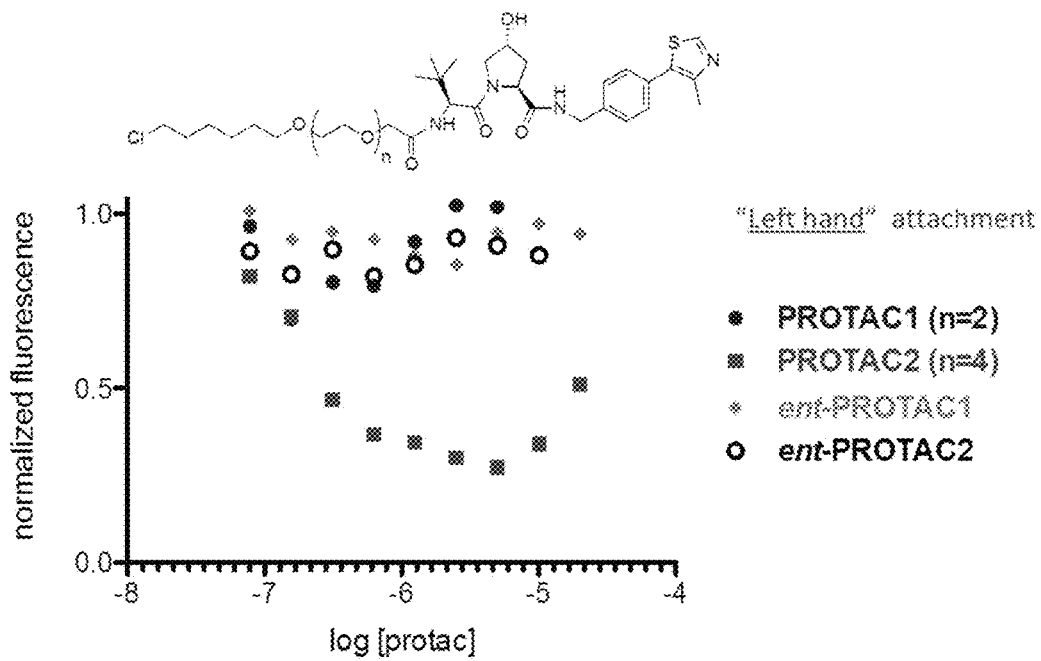
FIGS. 3A-3C depict the effects of linker length and sterochemical arrangements about the ligand on HALOTAGT protein degradation.
Figure 3B:
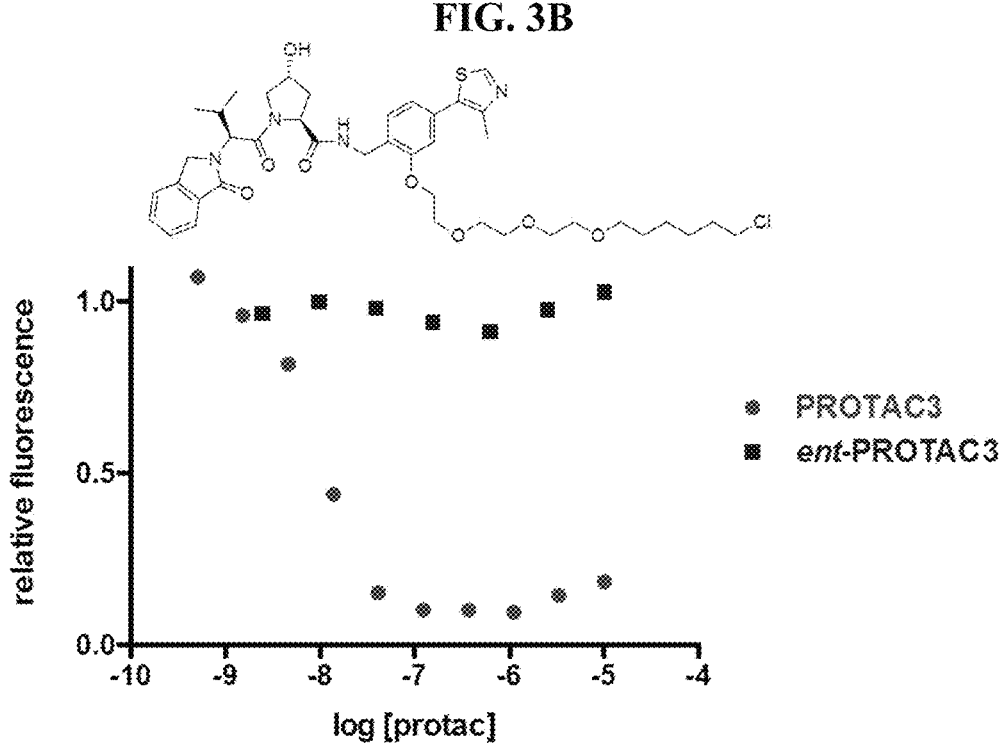
Figure 3C:
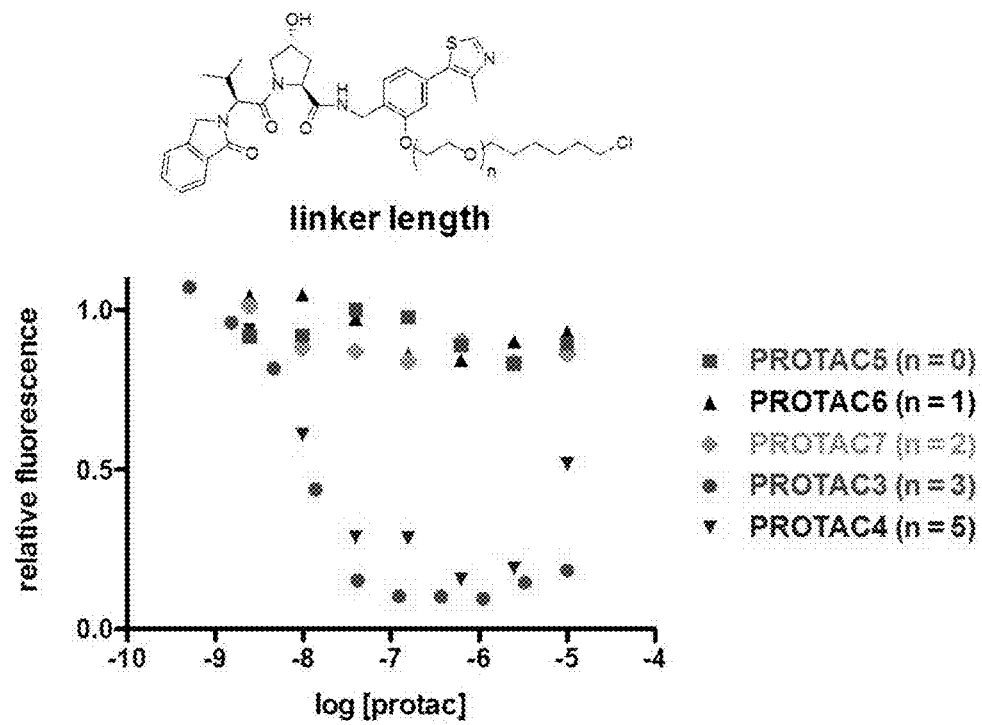
Figure 4:
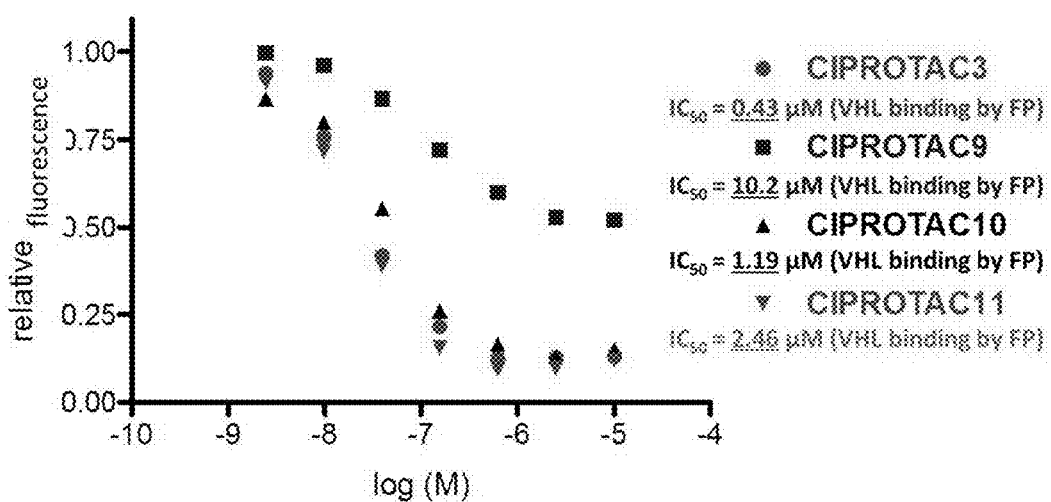
FIG. 4 depict the effect of VHL binding affinities (via Fluorescence Polarization (FP)) and the ligand concentration on the degradation of the HALOTAG™-GFP protein.

The PROTAC compounds of the instant invention are effective in affecting HALOTAG™ degradation, as illustrated in FIGS. 1A-1B, 2, 3A-3C and 4. FIG. 2 illustrates the stereospecificity of the HALOTAG™ degradation as the (R)-enantiomer potently and efficaciously affected degradation while the (S)-enantiomer was inactive. FIGS. 3A-3C and 4 demonstrate the effect of linker composition on HALOTAG™ degradation.

Figure 5:
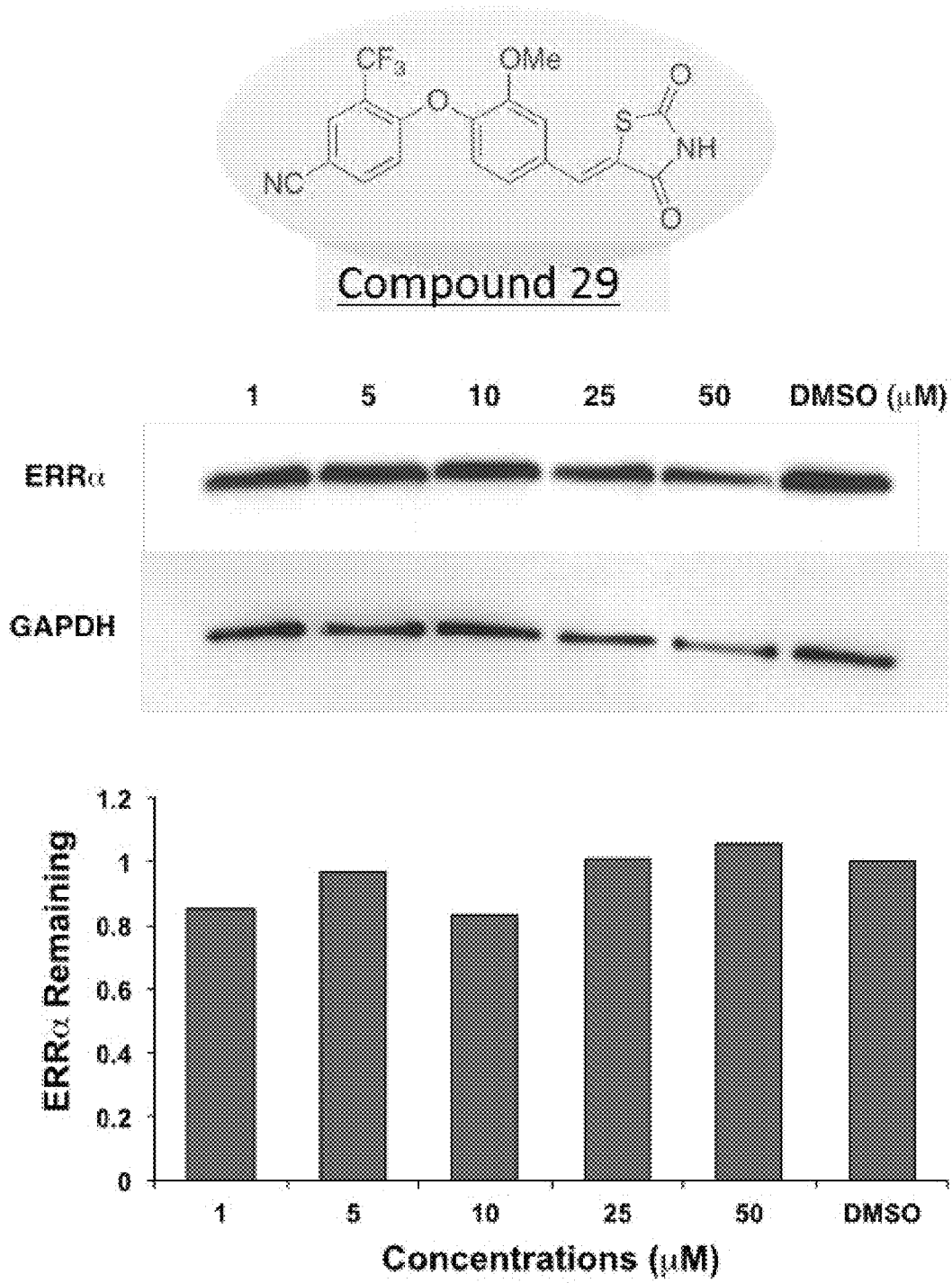

FIGS. 5-6 illustrate the ERRα inhibition activity of PROTAC compounds based on Compound 29, while FIG. 7 illustrates the effectiveness of PROTAC compounds in inhibiting RIPK2.

FIG. 8A depicts the proposed model of PROTAC-induced degradation. Von Hippel-Lindau protein (VHL, gray) is an E3 ubiquitin ligase that, under normoxic conditions, functions with a cullin RING ligase (green and yellow, shown attached to VHL) to degrade HIF1α. PROTACs recruit VHL to target proteins to induce their ubiquitination and subsequent proteasome-mediated downregulation.

FIG. 8B depicts the structure of PROTAC_ERRα with the ERRα ligand shown in orange (left box) and the modular VHL ligand in blue (right box), with asterisks indicating stereocenter(s) whose inversion (in PROTAC_ERRα_epi) abolishes VHL binding.

FIG. 8C depicts the structure of PROTAC_RIPK2 with the RIPK2 ligand shown in green (left box) and the modular VHL ligand in blue (right box), as in FIG. 8B.

FIGS. 9A-9E illustrate the downregulation by PROTACs of the protein levels of their respective targets.

FIG. 9A depicts the ability of PROTACs to downregulate ERRα protein levels.

MCF7 cells were treated with either PROTAC_ERRα or PROTAC_ERRα_epi as indicated for 8 h before harvesting. Where indicated, cells were pretreated with 1 mM of the proteasome inhibitor epoxomicin for 1 h before the treatment. Target protein levels were subsequently detected by western blot analysis. Protein levels were normalized to tubulin and DMSO control. Unless otherwise noted, all results in this work are representative of at least three independent experiments.

FIG. 9B depicts the ability of PROTACs to downregulate RIPK2. The experiments show an amelioration of efficacy at higher concentrations ('hook effect') consistent with a ternary complex-mediated mechanism. THP-1 cells were treated with the indicated amounts of RIPK2_PROTAC for 16 h and then analyzed by western blotting.

FIG. 9C illustrates the finding that degradation by PROTACs is dependent on the proteasome and the presence of the linkage between both targeting ligands. THP-1 cells were treated with the indicated compounds (1 µM for epoxomicin, 30 nM for all others) for 16 h and analyzed by western blotting.

FIG. 9D depicts the ability of PROTACs to downregulate RIPK2 by PROTAC_RIPK2. THP-1 cells were treated with 30 nM PROTAC_RIPK2 for the indicated times and then analyzed by western blotting.

FIG. 9E illustrates the finding that the ability of PROTACs to downregulate proteins is reversible. After a 4-h pretreatment with 30 nM PROTAC_RIPK2, the medium was replaced on THP-1 cells with fresh medium lacking PROTAC and the cells were washed thoroughly to remove residual PROTAC. After the indicated times, the cells were analyzed by western blotting. In FIGS. 9B and 9D, * indicates a nonspecific band observed on western blots.

FIGS. 10A-10F illustrate the finding that PROTACs induce the catalytic ubiquitination of their target protein in a reconstituted E1-E2-VHL assay.

FIG. 10A depicts the selectivity of the VHL ligand for VHL and associated proteins. The VHL ligand or inactive epimer was tethered to Sepharose beads and used to precipitate associated proteins. This was followed by washing of beads, elution of bound proteins and proteomic analysis of over 7,000 proteins.

FIG. 10B illustrates the binding selectivity of the VHL ligand to the VHL complex. Active (top three graphs) or inactive (bottom three graphs) VHL ligands were immobilized onto Sepharose beads and added to MCF7 cell lysates pretreated with active (experiments 1 and 4, counting from left to right) or inactive (experiments 2 and 5) free VHL ligand or vehicle (experiments 3 and 6). Immobilized active VHL ligand selectively precipitated members of the VHL E3-dependent ligase complex (see experiments 3 and 6). This effect was abrogated by prior treatment with free active VHL ligand (compare experiments 1 and 3) but not with inactive, epimeric VHL ligand (se experiments 2 and 3). The only other protein significantly precipitated was lactotransferrin, which was associated and competed with free ligand when using both active and inactive VHL ligands.

FIG. 10C illustrates the co-immunoprecipitation of VHL and RIPK2 by PROTAC_RIPK2. Cell lysates were immunoprecipitated with either IgG control (lanes 9, 10) or an anti VHL antibody (lanes 1-8) in the presence or absence of PROTAC_RIPK2 (lanes 1-3) or PROTAC_RIPK2_epi (lanes 4-6). The expression levels of over 7,000 proteins were quantified and normalized to the VHL precipitate without PROTAC present (lane 7).

FIG. 10D demonstrates that PROTAC_RIPK2 mediates direct RIPK2 ubiquitination in vitro. RIPK2 was labeled by autophosphorylation and then incubated with the indicated concentrations of PROTAC and the reconstituted ubiquitination cascade. Samples were quenched 15 min after initiation of the reaction, and imaged by PAGE and autoradiography. RIPK2-Ubn is indicated.

FIG. 10E illustrates the increase in the ubiquitination rate with increasing PROTAC concentration. Reactions were performed as in FIG. 10D with 50, 100 or 200 nM PROTAC_RIPK2 or PROTAC_RIPK2_epi, quenched at the indicated times and then analyzed by PAGE.

FIG. 10F demonstrates the ability of PROTACs to induce super-stoichiometric ubiquitination of RIPK2. Bands corresponding to 'Modified RIPK2' (RIPK2 that had received any number of ubiquitins) were excised, and the number of moles of RIPK2 from two parallel experiments was determined. Abundance of modified RIPK2 (in pmol) is plotted against time for the three different reactions employing the indicated amounts of PROTAC_RIPK2.

FIGS. 11A-11D illustrate that PROTACs are highly specific for their respective targets.

FIG. 11A depicts the selectivity of PROTAC_RIPK2 for RIPK2 degradation. THP-1 cells were treated for 18 h with 30 nM PROTAC_RIPK2 in biological duplicate and protein levels quantified. Data was plotted as fold change (log 2) of replicate 1 versus replicate 2. The red diagonal line represents proteins whose changes in protein levels were reproducible between the two experiments. A total of 7,640 proteins were quantified.

FIG. 11B illustrates the quantified levels of RIPK2 and MAPKAPK3 in THP-1 cells treated with either PROTAC_RIPK2 or PROTAC_RIPK2_epi. THP-1 cells were treated for the indicated times with 30 nM of either PROTAC_RIPK2 or PROTAC_RIPK2_epi as in FIG. 11A.

FIG. 11C depicts the quantified protein levels from MCF-7 cells treated for 24 h with 500 nM PROTAC_ERRα. Data was plotted as fold change ($\log_2$) of replicate 1 versus replicate 2. The red diagonal line represents proteins whose changes in protein levels were reproducible between the two experiments. A total of 7,576 proteins were quantified.

FIG. 11D demonstrates the quantified levels of ERRα and BCR from MCF-7 cells treated for the indicated times with 500 nM PROTAC_ERRα, as in FIG. 11C.

FIGS. 12A-12B illustrate the efficacy of PROTAC_ERRα in mice.

FIG. 12A depicts the efficacy data for mice (n=5) injected with either vehicle or 100 mg/kg PROTAC_ERRα (3× day, intraperitoneally). At ~5 h after the last injection, the mice were killed, and their tissues and tumors were collected and analyzed for ERRα expression by western blotting. Levels of ERRα were normalized to GAPDH levels and plotted, and are shown as mean±s.e.m. **P<=0.005, *P<0.05 by two-tailed, unpaired Student's t-test.

FIG. 12B depicts the analysis of tissues and plasma from FIG. 12A for levels of PROTAC_ERRα by LC/MS. The dashed line represents the $DC_{50}$ of PROTAC_ERRα when the in vitro degradation experiment was performed in 50% mouse serum. Each data point represents the levels of PROTAC_ERRα from a single mouse and tissue. Data are plotted and shown as mean±s.e.m.

FIG. 13 illustrated that exemplary PROTAC_RIPK2 is not toxic to cells.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of chemical structure:

ULM-L-PTM, wherein:
the ULM is a small molecule ubiquitin ligase binding moiety that comprises a group substituted with a hydroxyl group or a functional group that can be metabolized in a subject to a hydroxyl group and that is represented by the chemical structure:

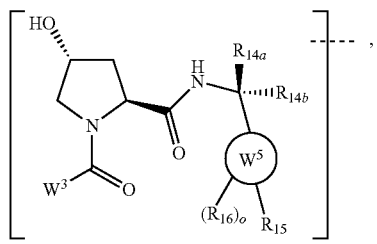

wherein:
$W^3$ is selected from the group consisting of optionally substituted aryl, optionally substituted heteroaryl, and

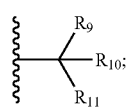

$R_9$ and $R_{10}$ are each independently selected from the group consisting of hydrogen, optionally substituted alkyl, optionally substituted cycloalkyl, optionally substituted hydroxyalkyl, optionally substituted heteroaryl, and haloalkyl; or $R_9$, $R_{10}$ and the carbon atom to which they are attached form an optionally substituted cycloalkyl;

$R_{11}$ is selected from the group consisting of optionally substituted heterocyclic, optionally substituted alkoxy, optionally substituted heteroaryl, optionally substituted aryl,

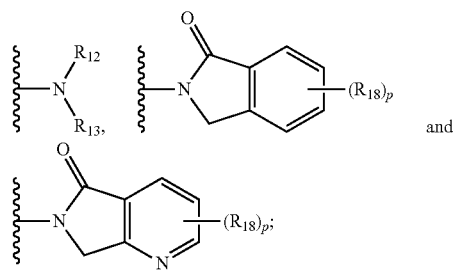

$R_{12}$ is selected from the group consisting of H and optionally substituted alkyl;

$R_{13}$ is selected from the group consisting of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, and optionally substituted aralkyl;

$R_{14a}$ and $R_{14b}$ are each independently selected from the group consisting of H, haloalkyl, and optionally substituted alkyl;

$W^5$ is selected from the group consisting of phenyl and a 5-10 membered heteroaryl;

$R_{15}$ is selected from the group consisting of: H; halogen; CN; OH; $NO_2$; $NR_{14a}R_{14b}$; $OR_{14a}$; $C(=O)NR_{14a}R_{14b}$; $NR_{14a}C(=O)R_{14b}$; $S(=O)_2NR_{14a}R_{14b}$; $NR_{14a}S(=O)_2R_{14b}$; optionally substituted alkyl; optionally substituted haloalkyl; optionally substituted haloalkoxy; optionally substituted aryl; optionally substituted heteroaryl; optionally substituted cycloalkyl; and optionally substituted cycloheteroalkyl;

each $R_{16}$ is independently selected from the group consisting of halogen, optionally substituted alkyl, optionally substituted haloalkyl, hydroxy, and optionally substituted haloalkoxy;

o is 0, 1, 2, 3, or 4;

each $R_{18}$ is independently selected from the group consisting of halogen, optionally substituted alkoxy, cyano, optionally substituted alkyl, haloalkyl, haloalkoxy and a chemical linker; and p is 0, 1, 2, 3, or 4;

the L is a bond or a chemical linker that is chemically linked to the ULM and the PTM; and the PTM is capable of binding to Estrogen Related Receptor alpha (ERRα) and is selected from the group consisting of

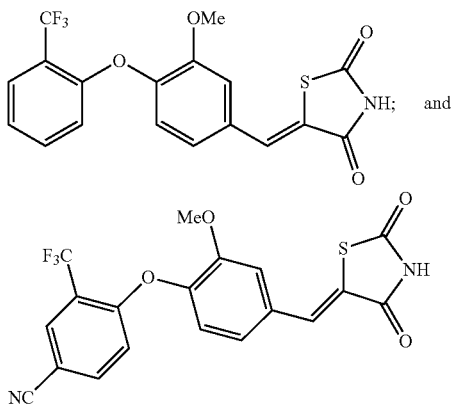

wherein, upon binding of the EERα to the compound, the ERRα is ubiquitinated by a ubiquitin ligase; or a pharmaceutically acceptable salt, enantiomer, stereoisomer, solvate, polymorph, or prodrug thereof.

2. The compound of claim 1, wherein:

L is -$A_1$ . . . $A_q$-;

$A_1$ to $A_q$ are each independently selected from the group consisting of a bond, $CR^{L1}R^{L2}$, O, S, S=O, S(=O)$_2$, $NR^{L3}$, S(=O)$_2NR^{L3}$, S(=O)$NR^{L3}$, C(=O)$NR^{L3}$, $NR^{L3}C(=O)NR^{L4}$, $NR^{L3}S(=O)_2NR^{L4}$, C(=O), $CR^{L1}$=$CR^{L2}$, C≡C, $SiR^{L1}R^{L2}$, P(=O)$R^{L1}$, P(=O)OR$^{L1}$, $NR^{L3}C(=N-CN)NR^{L4}$, $NR^{L3}C(=N-CN)$, $NR^{L3}C(=C-NO_2)NR^{L4}$, $C_{3-11}$ cycloalkyl optionally substituted with 0-6 substituents selected from the group consisting of $R^{L1}$ and $R^{L2}$, $C_{3-11}$ heterocyclyl optionally substituted with 0-6 substituents selected from the group consisting of $R^{L1}$ and $R^{L2}$, aryl optionally substituted with 0-6 substituents selected from the group consisting of $R^{L1}$ and $R^{L2}$, and heteroaryl optionally substituted with 0-6 substituents selected from the group consisting of $R^{L1}$ and $R^{L2}$, wherein:

$R^{L1}$ and $R^{L2}$ each independently can be linked to other A groups to form a cycloalkyl or heterocyclyl moiety that can be further optionally substituted with 0-4 $R^{L5}$ groups;

$R^{L1}$, $R^{L2}$, $R^{L3}$, $R^{L4}$, and $R^{L5}$ are each independently selected from the group consisting of H, $C_{1-8}$ alkyl, O($C_{1-8}$ alkyl), S($C_{1-8}$ alkyl), NH($C_{1-8}$ alkyl), N($C_{1-8}$ alkyl)$_2$, $C_{3-11}$ cycloalkyl, aryl, heteroaryl, $C_{3-11}$ heterocyclyl, O($C_{1-8}$ cycloalkyl), S($C_{1-8}$ cycloalkyl), NH($C_{1-8}$ cycloalkyl), N($C_{1-8}$ cycloalkyl)$_2$, N($C_{1-8}$ cycloalkyl)($C_{1-8}$ alkyl), OH, NH$_2$, SH, SO$_2$($C_{1-8}$ alkyl), P(=O)(O$C_{1-8}$ alkyl)($C_{1-8}$ alkyl), P(=O)(O$C_{1-8}$ alkyl)$_2$, C≡C—($C_{1-8}$ alkyl), C≡CH, CH=CH($C_{1-8}$ alkyl), C($C_{1-8}$ alkyl)=CH($C_{1-8}$ alkyl), C($C_{1-8}$ alkyl)=C($C_{1-8}$ alkyl)$_2$, Si(OH)$_3$, Si($C_{1-8}$ alkyl)$_3$, Si(OH)($C_{1-8}$ alkyl)$_2$, C(=O)($C_{1-8}$ alkyl), CO$_2$H, halogen, CN, CF$_3$, CHF$_2$, CH$_2$F, NO$_2$, SF$_5$, SO$_2$NH($C_{1-8}$ alkyl), SO$_2$N($C_{1-8}$ alkyl)$_2$, S(=O)NH($C_{1-8}$ alkyl), S(=O)N($C_{1-8}$alkyl)$_2$, C(=O)NH($C_{1-8}$ alkyl), C(=O)N($C_{1-8}$ alkyl)$_2$, N($C_{1-8}$ alkyl)C(=O)NH($C_{1-8}$ alkyl), N($C_{1-8}$ alkyl)C(=O)N($C_{1-8}$ alkyl)$_2$, NHC(=O)NH($C_{1-8}$ alkyl), NHC(=O)N($C_{1-8}$ alkyl)$_2$, NHC(=O)NH$_2$, N($C_{1-8}$ alkyl)SO$_2$NH($C_{1-8}$ alkyl), N($C_{1-8}$ alkyl)SO$_2$N($C_{1-8}$ alkyl)$_2$, NHSO$_2$NH($C_{1-8}$ alkyl), NHSO$_2$N($C_{1-8}$ alkyl)$_2$, and NHSO$_2$NH$_2$; and q is an integer greater than or equal to 1.

3. The compound of claim 1, wherein the ULM is represented by the chemical structure:

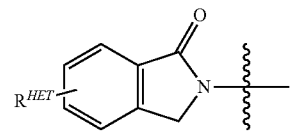

wherein $R^{1'}$ is —OH;

$R^{2'}$ is —NH—CH$_2$-Aryl-HET;

$R^{3'}$ is selected from the group consisting of optionally substituted alkyl, —(CH)$R^{CR3'}$—NH—C(=O)—$R^{3P1}$, and —(CH)$R^{CR3'}$—$R^{3P2}$;

$R^{CR3'}$ is optionally substituted $C_1$-$C_4$ alkyl;

$R^{3P1}$ is selected from the group consisting of optionally substituted $C_1$-$C_6$ alkyl, optionally substituted oxetane, —(CH$_2$)$_n$OCH$_3$ wherein n is 1 or 2, optionally substituted phenyl, and morpholino linked to the carbonyl at the 2- or 3-position;

$R^{3P2}$ is selected from the group consisting of

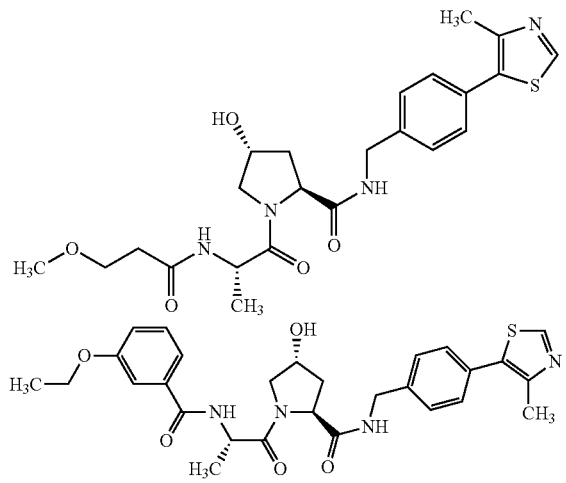

and optionally substituted aryl;

HET is selected from the group consisting of optionally substituted thiazole, oxazole, isoxazole, and isothiazole;

$R^{HET}$ is selected from the group consisting of H, halogen, CN, optionally substituted $C_1$-$C_6$ alkyl, optionally substituted $C_1$-$C_6$ alkoxy, and optionally substituted aryl; and the ULM group is covalently bonded to a linker group to which is attached a PTM group, or a pharmaceutically acceptable salt, stereoisomer, solvate or polymorph thereof.

4. The compound of claim 3, wherein the ULM is selected from the group consisting of:

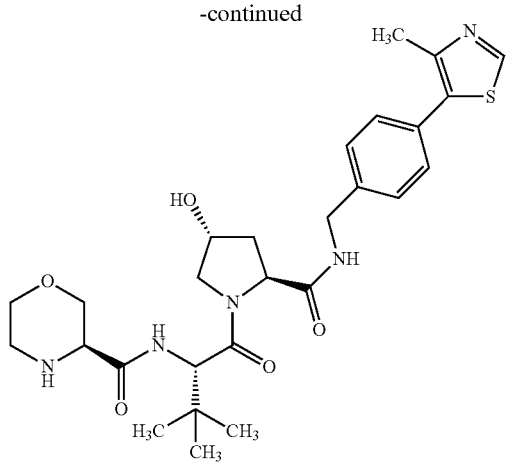
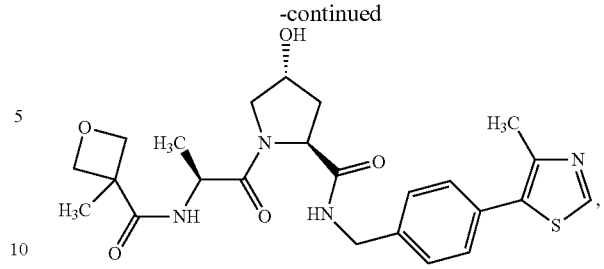
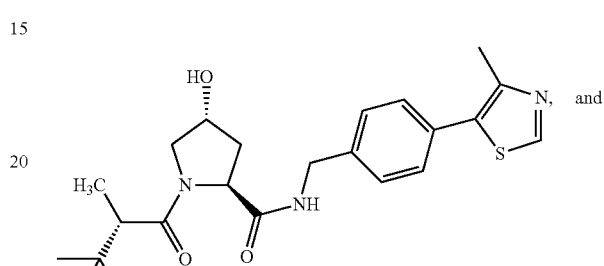
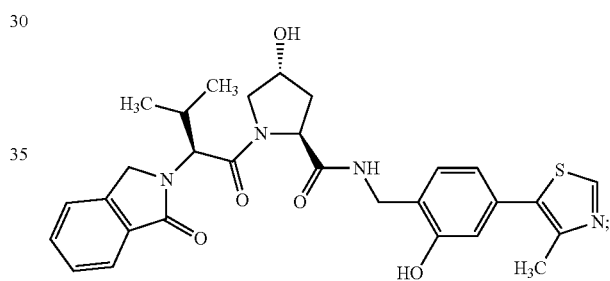
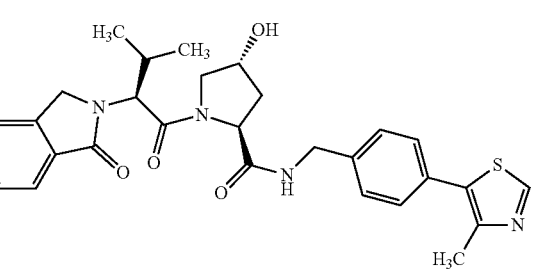

wherein the ULM group is covalently bonded to the L group to which is attached the PTM group, or a pharmaceutically acceptable salt, stereoisomer, solvate, polymorph or prodrug thereof.

5. The compound of claim 2, wherein the L is a polyethyleneglycol optionally substituted with aryl or phenyl, having from 1 to 100 ethylene glycol units.

6. The compound of claim 5, wherein the L is a polyethyleneglycol group that is optionally substituted with aryl or phenyl, having from 1 to 10 ethylene glycol units.

7. The compound of claim 3, wherein the compound is selected from the group consisting of:

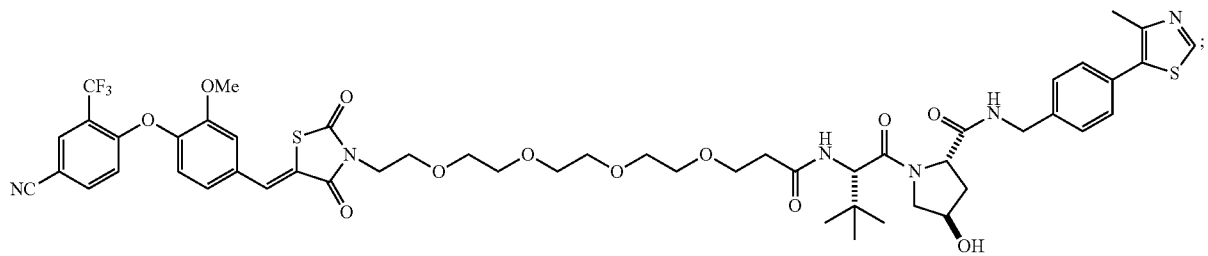

-continued
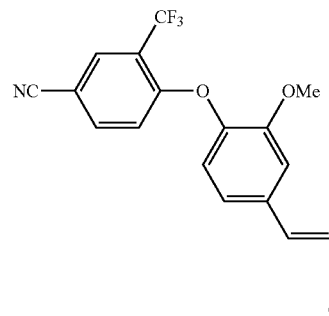
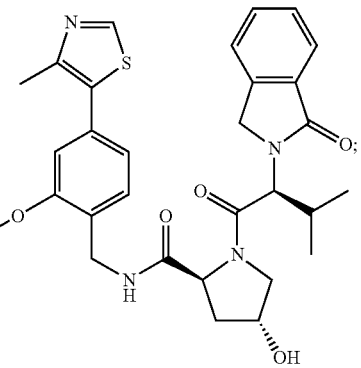
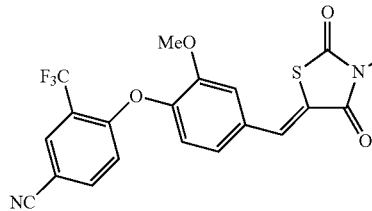
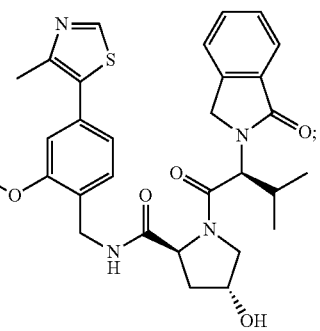
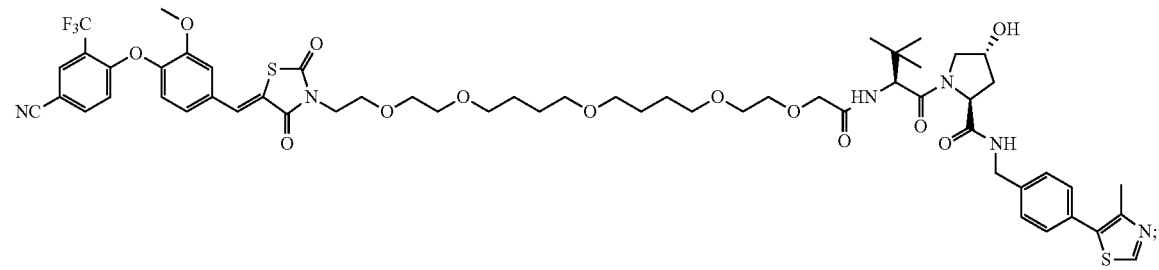
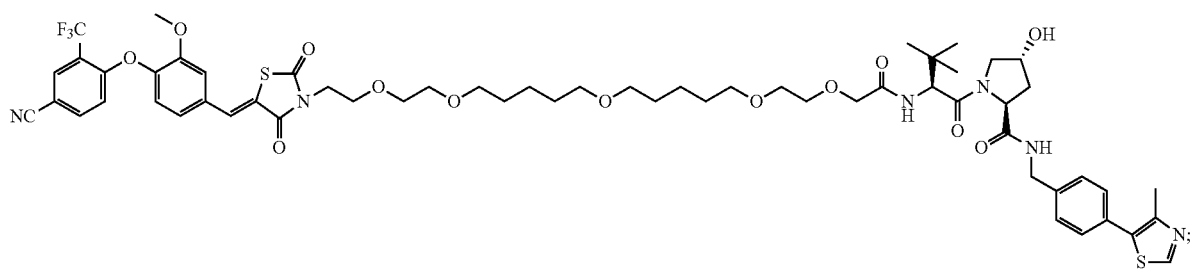
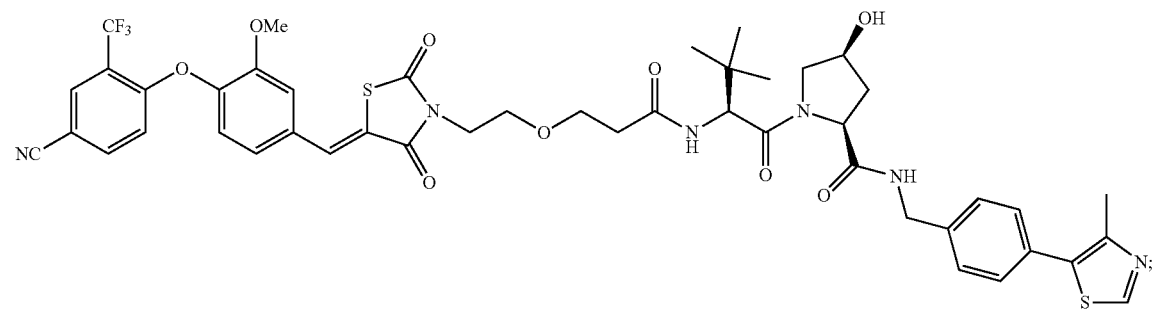

129
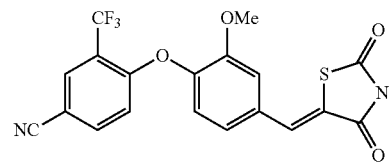
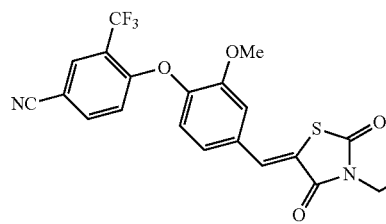
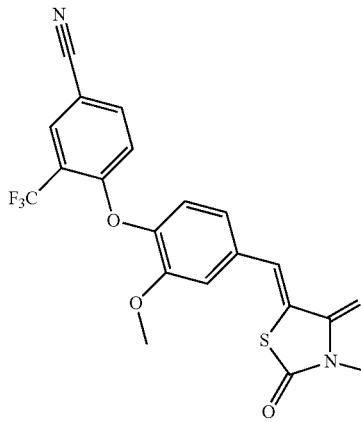
130
-continued
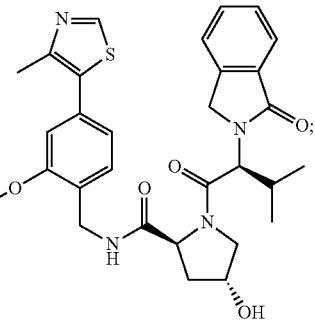
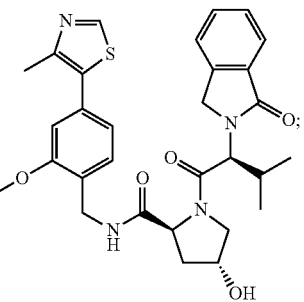
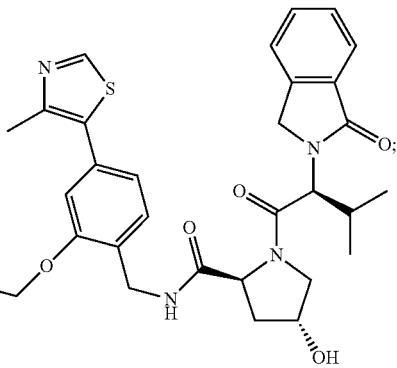
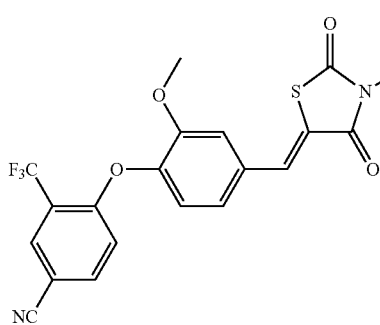
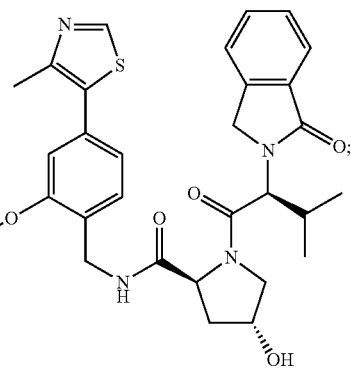

131
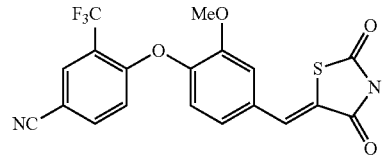
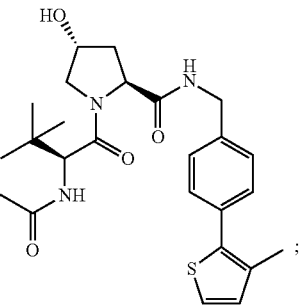
;
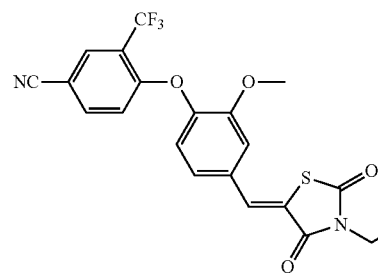
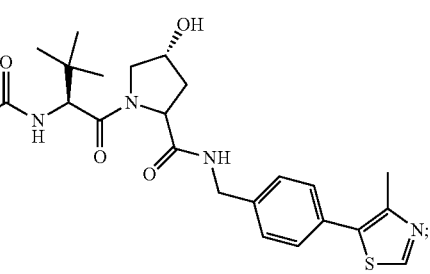
;
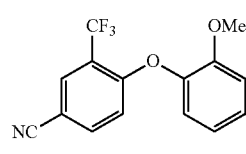
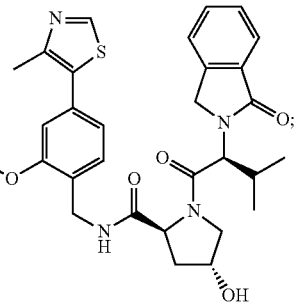
;
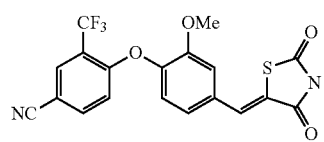
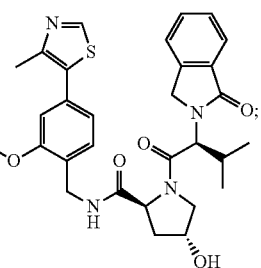
;
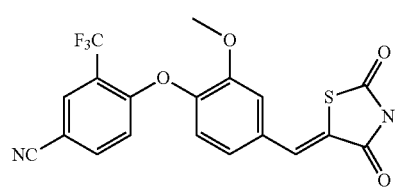
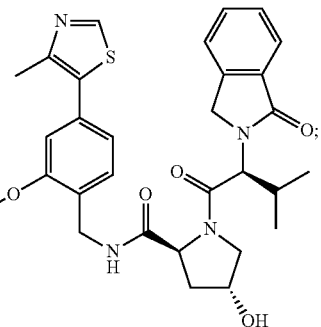
;
132
-continued -continued
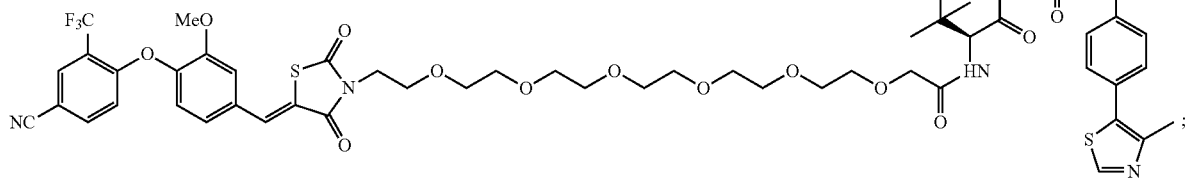
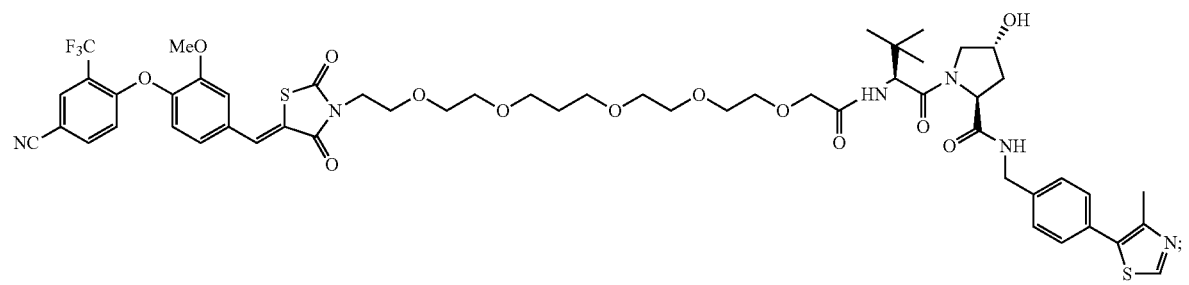
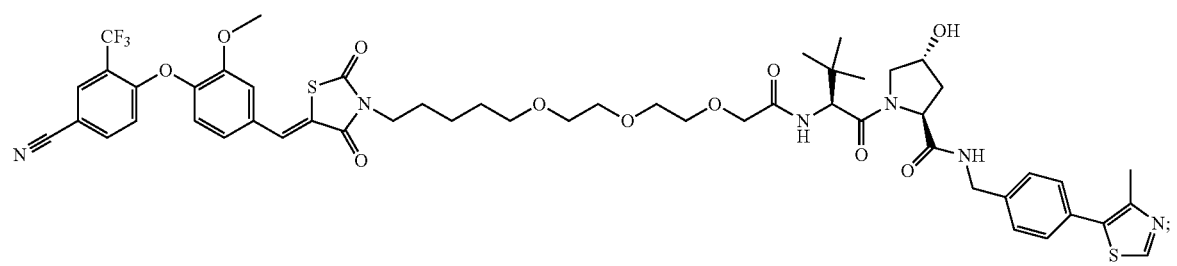
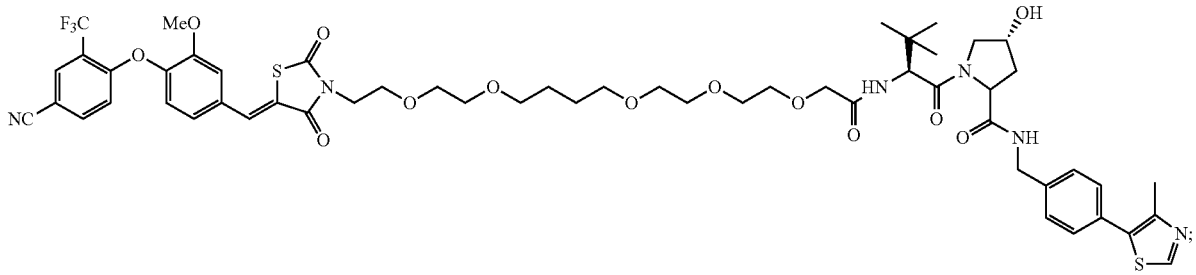
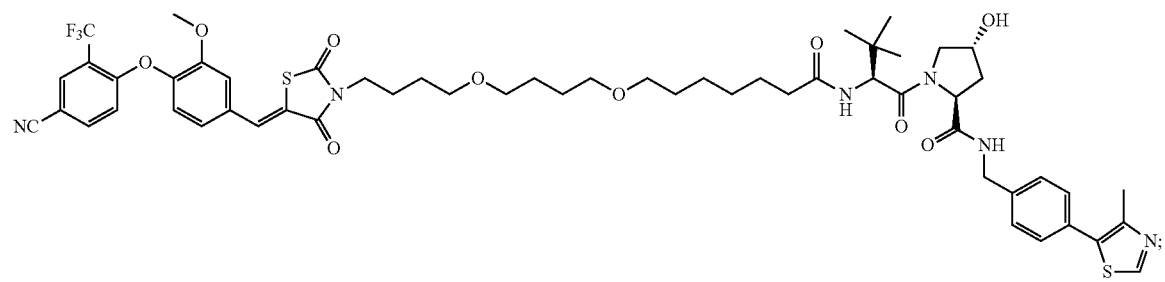
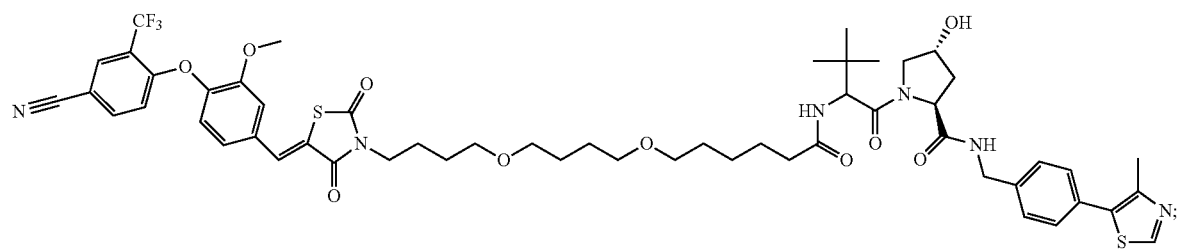

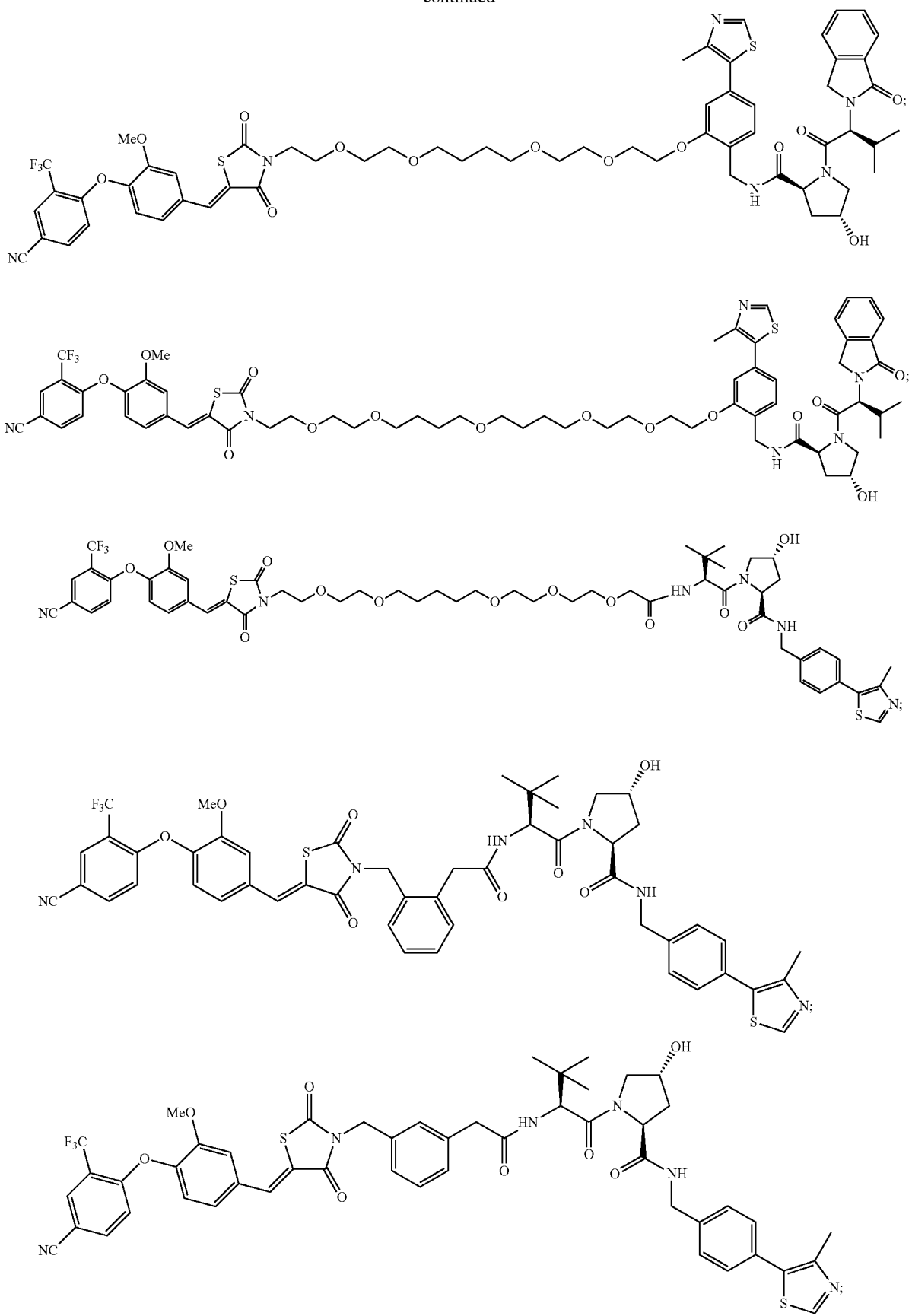

-continued

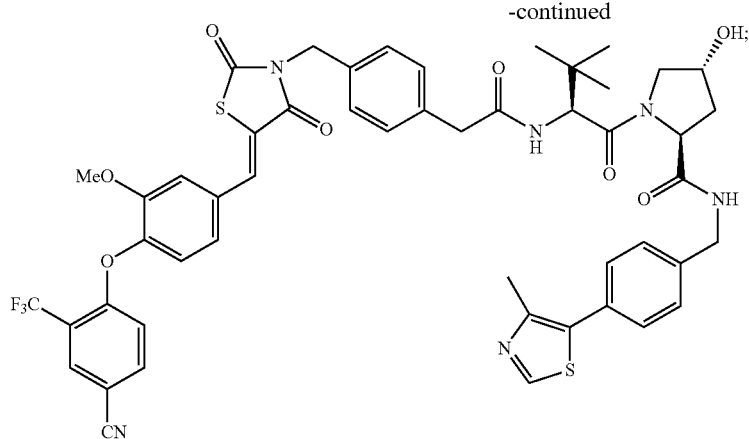

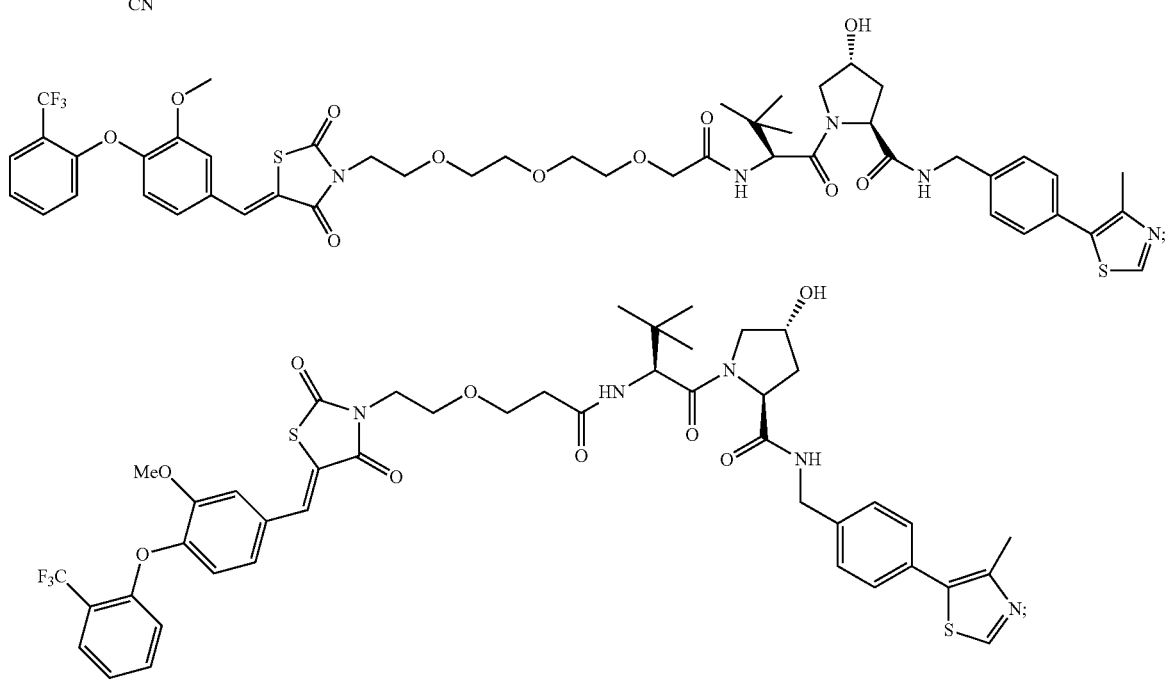

or a pharmaceutically acceptable salt, enantiomer, diastereoisomer, solvate, polymorph or prodrug thereof.

8. A pharmaceutical composition comprising the compound of claim 1, further comprising a pharmaceutically acceptable carrier, additive or excipient, and optionally further comprising an additional bioactive agent.

9. The composition of claim 8, wherein the additional bioactive agent is an anticancer agent.

\* \* \* \* \*